United States Patent
Virgili-Bernado et al.

(10) Patent No.: US 10,562,908 B2
(45) Date of Patent: Feb. 18, 2020

(54) ORTHO SUBSTITUTED PHENYLPYRAZOLO- AND PHENYLPYRROLO-PYRIDAZINE DERIVATIVES HAVING MULTIMODAL ACTIVITY AGAINST PAIN

(71) Applicant: ESTEVE PHARMACEUTICALS, S.A., Barcelona (ES)

(72) Inventors: Marina Virgili-Bernado, Barcelona (ES); Monica Alonso-Xalma, Barcelona (ES); Carmen Almansa-Rosales, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/464,736

(22) PCT Filed: Nov. 30, 2017

(86) PCT No.: PCT/EP2017/080944
§ 371 (c)(1),
(2) Date: May 29, 2019

(87) PCT Pub. No.: WO2018/100045
PCT Pub. Date: Jun. 7, 2018

(65) Prior Publication Data
US 2019/0284195 A1    Sep. 19, 2019

(30) Foreign Application Priority Data

Nov. 30, 2016 (EP) .................................... 16382577

(51) Int. Cl.
*C07D 487/04* (2006.01)
(52) U.S. Cl.
CPC .................................. *C07D 487/04* (2013.01)
(58) Field of Classification Search
CPC ..................................................... C07D 487/04
USPC ..................................................... 514/210.21
See application file for complete search history.

(56) References Cited

FOREIGN PATENT DOCUMENTS

WO    WO2004/006836        1/2004
WO    WO-2004006836 A2 *   1/2004    ........... A61K 31/045

OTHER PUBLICATIONS

International Search Report for PCT/EP2017/080944 dated Feb. 27, 2018.
Myatt, James W., "Pyrazolopyridazine alpha-2-delta-1 ligands for the treatment of neuropathic pain", Bioorganic & Medicinal Chemistry Letters, 20, 2010, pp. 4683-4688.

* cited by examiner

*Primary Examiner* — Kahsay Habte
(74) *Attorney, Agent, or Firm* — Hueschen and Sage

(57) ABSTRACT

The present invention relates to ortho substituted phenylpyrazolo- and pyrrolo-pyridazine derivatives having dual pharmacological activity towards both the α2δ subunit, in particular the α2δ-1 subunit, of the voltage-gated calcium channel and the μ-opioid receptor, to processes of preparation of such compounds, to pharmaceutical compositions comprising them, and to their use in therapy, in particular for the treatment of pain.

17 Claims, No Drawings

ORTHO SUBSTITUTED PHENYLPYRAZOLO- AND PHENYLPYRROLO-PYRIDAZINE DERIVATIVES HAVING MULTIMODAL ACTIVITY AGAINST PAIN

FIELD OF THE INVENTION

The present invention relates to compounds having dual pharmacological activity towards both the $\alpha_2\delta$ subunit of the voltage-gated calcium channel, and the μ-opioid receptor (MOR or mu-opioid receptor) and more particularly to ortho substituted phenylpyrazolo- and pyrrolo-pyridazine derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved (Turk, D. C., Wilson, H. D., Cahana, A.; 2011; *Lancet*; 377; 2226-2235). Pain affects a big portion of the population with an estimated prevalence of 20% and its incidence, particularly in the case of chronic pain, is increasing due to the population ageing. Additionally, pain is clearly related to comorbidities, such as depression, anxiety and insomnia, which leads to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al., Pharmacol Rev. 2015 67:821-70). The VGCC are assembled through interactions of different subunits, namely $\alpha_1$ ($Ca_v\alpha_1$), β ($Ca_v\beta$) $\alpha_2\delta$ ($Ca_v\alpha_2\delta$) and γ ($Ca_v\gamma$). The $\alpha_1$ subunits are the key porous forming units of the channel complex, being responsible for the $Ca^{2+}$ conduction and generation of $Ca^{2+}$ influx. The $\alpha_2\delta$, β, and γ subunits are auxiliary, although very important for the regulation of the channel, since they increase the expression of the $\alpha_1$ subunits in the plasma membrane as well as modulate their function, resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N-($Ca_v2.2$), P/Q-($Ca_v2.1$), and R-($Ca_v2.3$) types, depending on the channel forming $Ca_v\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo, Neurotherapeutics. 2009 6:679-92; Zamponi et al., 2015 supra; Neumaier et al., Prog Neurobiol. 2015 129:1-36.). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain. (Perret and Luo, 2009, supra; Vink and Alewood, Br J Pharmacol. 2012 167:970-89.).

The $Ca_v1$ and $Ca_v2$ subfamilies contain an auxiliary $\alpha_2\delta$ subunit, which is the therapeutic target of the gabapentinoid drugs of value in certain epilepsies and chronic neuropathic pain. To date, there are four known $\alpha_2\delta$ subunits, each encoded by a unique gene and all possessing splice variants. Each $\alpha_2\delta$ protein is encoded by a single messenger RNA and is post-translationally cleaved and then linked by disulfide bonds. Four genes encoding $\alpha_2\delta$ subunits have now been cloned. $\alpha_2\delta$-1 was initially cloned from skeletal muscle and shows a fairly ubiquitous distribution. The $\alpha_2\delta$-2 and $\alpha_2\delta$-3 subunits were subsequently cloned from brain. The most recently identified subunit, $\alpha_2\delta$-4, is largely non-neuronal. The human $\alpha_2\delta$-4 protein sequence shares 30, 32 and 61% identity with the human $\alpha_2\delta$-1, $\alpha_2\delta$-2 and $\alpha_2\delta$-3 subunits, respectively. The gene structure of all $\alpha_2\delta$ subunits is similar. All $\alpha_2\delta$ subunits show several splice variants (Davies et al., Trends Pharmacol Sci. 2007 28:220-8; Dolphin A C, Nat Rev Neurosci. 2012 13:542-55, Biochim Biophys Acta. 2013 1828:1541-9.).

The $Ca_v\alpha_2\delta$-1 subunit may play an important role in neuropathic pain development (Perret and Luo, 2009, supra; Vink and Alewood, 2012, supra). Biochemical data have indicated a significant $Ca_v\alpha_2\delta$-1, but not $Ca_v\alpha_2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha_2\delta$-1 subunit to the central presynaptic terminals diminishes tactile allodynia in nerve injured animals, suggesting that elevated DRG $Ca_v\alpha_2\delta$-1 subunit contributes to neuropathic allodynia.

The $Ca_v\alpha_2\delta$-1 subunit (and the $Ca_v\alpha_2\delta$-2, but not $Ca_v\alpha_2\delta$-3 and $Ca_v\alpha_2\delta$-4, subunits) is the binding site for gabapentin which has anti-allodynic/hyperalgesic properties in patients and animal models. Because injury-induced $Ca_v\alpha_2\delta$-1 expression correlates with neuropathic pain development and maintenance, and various calcium channels are known to contribute to spinal synaptic neurotransmission and DRG neuron excitability, injury-induced $Ca_v\alpha_2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha_2\delta$-1 subunit can block nerve injury-induced $Ca_v\alpha_2\delta$-1 upregulation and prevent the onset of allodynia and reserve established allodynia.

As mentioned above, the $\alpha_2\delta$ subunits of VGCC form the binding site for gabapentin and pregabalin, which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha_2\delta$ subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009, supra; Vink and Alewood, 2012, supra, Zamponi et al., 2015, supra).

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies*. Eur J Pain 9, 113-6 (2005)]. Moreover, prolonged treatment with morphine may result in tolerance to its analgesic effects, most likely due to treatment-induced MOR down-regulation, interalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al., Nat Biotechnol 2009; 27: 659-666.).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al., Lancet Neurol. 2013 November; 12(11):1084-95.). In fact, positive synergistic interaction for several compounds, including analgesics, has been described (Schröder et al., J Pharmacol Exp Ther. 2011; 337:312-20. Erratum in: J Pharmacol Exp Ther. 2012; 342:232; Zhang et al., Cell Death Dis. 2014; 5:e1138; Gilron et al., 2013, supra).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, Nat Chem Biol. 2008; 4:682-90.).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008, supra).

Thus, the present application, relates to the advantages of having dual activity, for μ-receptor and the $\alpha_2\delta$-1 subunit of voltage-gated calcium channels, in the same molecule to treat chronic pain.

In this way, the present invention relates to compounds having a complementary dual mechanism of action (μ-receptor agonist and blocker of the $\alpha_2\delta$ subunit, in particular the $\alpha_2\delta$-1 subunit, of voltage-gated calcium channels) which implies a better profile of tolerability than the strong opioids (morphine, oxycodone, fentanyl etc) and/or better efficacy and tolerability than gabapentinoids (pregabalin and gabapentin).

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies (Mao, J., Gold, M. S., Backonja, M.; 2011; J. Pain; 12; 157-166).

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

The authors of the present invention, have found a series of compounds that show dual pharmacological activity towards both the $\alpha_2\delta$ subunit, in particular the $\alpha_2\delta$-1 subunit, of the voltage-gated calcium channel, and the μ-opioid receptor (MOR or mu-opioid receptor) resulting in an innovative, effective and alternative solution for the treatment of pain.

In view of the existing results of the currently available therapies and clinical practices, the present invention offers a solution by combining in a single compound binding to two different targets relevant for the treatment of pain. This was mainly achieved by providing the compounds according to the invention that bind both to the μ-opioid receptor and to the $\alpha_2\delta$ subunit, in particular the $\alpha_2\delta$-1 subunit, of the voltage-gated calcium channel.

SUMMARY OF THE INVENTION

In this invention a family of structurally distinct ortho substituted phenylpyrazolo- and pyrrolo-pyridazine derivatives, encompassed by formula (I), which have a dual pharmacological activity towards both the $\alpha_2\delta$ subunit, in particular the $\alpha_2\delta$-1 subunit, of the voltage-gated calcium channel, and the μ-opioid receptor was identified, thus solving the above problem of identifying alternative or improved pain treatments by offering such dual compounds.

The main object of the invention is directed to a compound having a dual activity binding to the $\alpha_2\delta$ subunit, in particular the $\alpha_2\delta$-1 subunit, of the voltage-gated calcium channel and the μ-opioid receptor, for use in the treatment of pain.

As this invention is aimed at providing a compound or a chemically related series of compounds which act as dual ligands of the $\alpha_2\delta$ subunit, in particular the $\alpha_2\delta$-1 subunit, of the voltage-gated calcium channel and the μ-opioid receptor, it is a very preferred embodiment if the compound has a binding expressed as $K_i$ responding to the following scales:

$K_i(\mu)$ is preferably <1000 nM, more preferably <500 nM, even more preferably <100 nM.

$K_i(\alpha_2\delta$-1) is preferably <10000 nM, more preferably <5000 nM, even more preferably <500 nM or even more preferably <100 nM.

The invention is directed in a main aspect to a compound of general Formula (I),

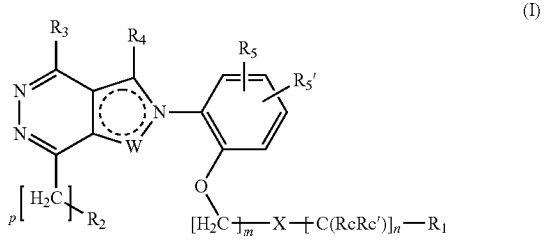

wherein $R_1$, $R_2$, $R_3$, $R_4$, $R_5$, $R_{5'}$, $R_c$, $R_{c'}$, X, W, m and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct ortho substituted phenylpyrazolo- and pyrrolo-pyridazine derivatives which have a dual pharmacological activity towards both the $\alpha_2\delta$ subunit, in particular the $\alpha_2\delta$-1 subunit, of the voltage-gated calcium channel and the μ-opioid receptor.

The invention is directed to compounds having a dual activity binding to the $\alpha_2\delta$ subunit, in particular the $\alpha_2\delta$-1 subunit, of the voltage-gated calcium channel and the μ-opioid receptor for use in the treatment of pain.

As this invention is aimed at providing a compound or a chemically related series of compounds which act as dual ligands of the $\alpha_2\delta$ subunit, in particular the $\alpha_2\delta$-1 subunit, of the voltage-gated calcium channel and the μ-opioid receptor it is a preferred embodiment if the compound has a binding expressed as $K_i$ responding to the following scales:

$K_i(\mu)$ is preferably <1000 nM, more preferably <500 nM, even more preferably <100 nM.

$K_i(\alpha_2\delta$-1) is preferably <10000 nM, more preferably <5000 nM, even more preferably <500 nM The applicant has surprisingly found that the problem of providing a new effective and alternative for treating pain and pain related disorders can be solved by using a multimodal balanced analgesic approach combining two different synergistic activities in a single drug (i.e., dual ligands which are bifunctional and bind to μ-opioid receptor and to $\alpha_2\delta$ subunit, in particular the $\alpha_2\delta$-1 subunit, of the voltage-gated calcium channel), thereby enhancing through the $\alpha_2\delta$ blockade without increasing the undesirable side effects. This supports the therapeutic value of a dual agent, whereby the $\alpha_2\delta$ binding component acts as an intrinsic adjuvant of the MOR binding component.

A dual compound that possess binding to both the μ-opioid receptor and to the $\alpha_2\delta$ subunit of the voltage-gated calcium channel shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: blockade of the $\alpha_2\delta$ subunit, in particular the $\alpha_2\delta$-1 subunit, of the voltage-gated calcium channel and μ-opioid receptor agonism It has to be noted, though, that functionalities "antagonism" and "agonism" are also sub-divided in their effect into subfunctionalities like partial agonism or inverse agonism. Accordingly, the functionalities of the compound should be considered within a relatively broad bandwidth.

An antagonist blocks or dampens agonist-mediated responses. Known subfunctionalities are neutral antagonists or inverse agonists.

An agonist increases the activity of the receptor above its basal level. Known subfunctionalities are full agonists, or partial agonists.

In addition, the two mechanisms complement each other since MOR agonists are only marginally effective in the treatment of neuropathic pain, while the blockers of the $\alpha_2\delta$ subunit, in particular the $\alpha_2\delta$-1 subunit, of voltage-gated calcium channels show outstanding effects in preclinical neuropathic pain models. Thus, the $\alpha_2\delta$ component, in particular the $\alpha_2\delta$-1 component, adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bomot A, Bauer U, Brown A, Firth M, Hellawell C, Engkvist O. Systematic Exploration of Dual-Acting Modulators from a Combined Medicinal Chemistry and Biology Perspective. J. Med. Chem, 56, 1197-1210 (2013)].

In its broader aspect, the present invention is directed to compounds of general Formula (I):

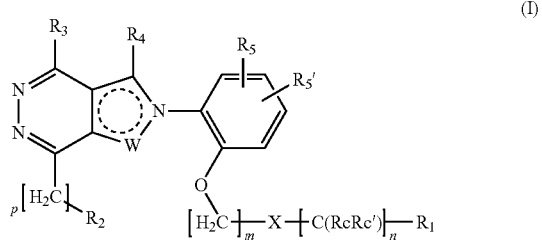

(I)

wherein
m is 0, 1, 2, 3 or 4;
n is 0, 1, 2, 3 or 4;
p is 0, 1, 2, 3 or 4;
W is nitrogen or —C($R_{4'}$)—;
X is selected from a bond, substituted or unsubstituted aryl or —$CR_xR_{x'}$—;
  $R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
  $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from —$NR_6R_{6'}$ and substituted or unsubstituted N-containing-heterocyclyl;
  wherein $R_6$ and $R_{6'}$ are independently selected from hydrogen, substituted or unsubstituted $C_{1-6}$alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
$R_2$ is selected from hydrogen, —$NR_7R_{7'}$, —CN, —$CHR_7R_{7'}$ and substituted or unsubstituted heterocyclyl;
  wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

$R_3$ is selected from hydrogen, substituted or unsubstituted $C_{1-6}$alkyl, substituted or unsubstituted $C_{2-6}$ alkenyl and substituted or unsubstituted $C_{2-6}$ alkynyl;
$R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_{4'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —$OR_8$, —$NO_2$, —$NR_8R_{8'}$, —$NR_8C(O)R_{8'}$, —$NR_8S(O)_2R_{8'}$, —$S(O)_2NR_8R_{8'}$, —$NR_8C(O)NR_8R_{8''}$, —$SR_8$, —$S(O)R_8$, $S(O)_2R_8$, —CN, haloalkyl, haloalkoxy, —$C(O)OR_8$, —$C(O)NR_8R_{8'}$, —$OCH_2CH_2OR_8$, —$NR_8S(O)_2NR_8R_{8''}$ and $C(CH_3)_2OR_8$
  wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;
$R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
alternatively, $R_c$ and $R_{c'}$ may form with the carbon atom to which they are attached, a substituted or unsubstituted cycloalkyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a particular embodiment the following proviso applies: —$[CH_2]_m$—X—$[C(R_cR_{c'})]_n$—$R_1$ is attached to the oxygen atom through a carbon atom.

In a further embodiment the compound according to the invention of general Formula (I) is a compound of general Formula (I')

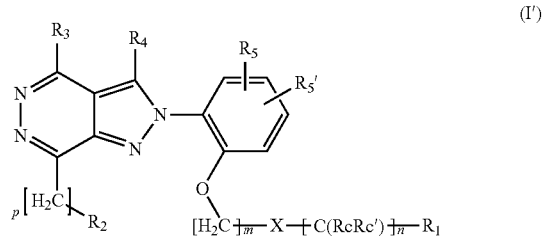

(I')

wherein $R_1$, $R_2$, $R_3$, $R_4$, $R_5$, $R_{5'}$, $R_c$, $R_{c'}$, X, m, n and p are as defined below in the detailed description, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (I²'),

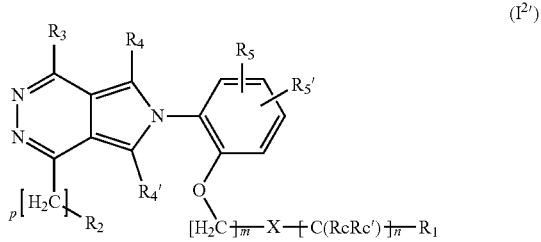

(I²')

wherein R₁, R₂, R₃, R₄, R₅, R₅', R_c, R_c', X, m, n and p are as defined below in the detailed description,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (I')

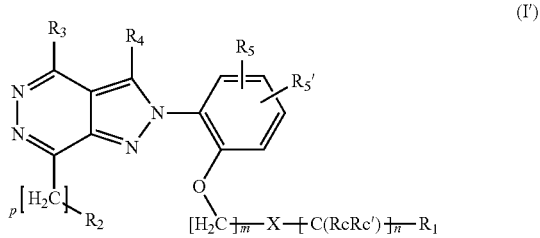

(I')

wherein
m is 0, 1, 2, 3 or 4;
n is 0, 1, 2, 3 or 4;
p is 0, 1, 2, 3 or 4;
X is selected from a bond, substituted or unsubstituted aryl or —CR$_x$R$_{x'}$—;
  R$_x$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
  R$_{x'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R₁ is selected from —NR₆R₆' and substituted or unsubstituted N-containing-heterocyclyl;
  wherein R₆ and R₆' are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
R₂ is selected from hydrogen, —NR₇R₇', —CN, —CHR₇R₇' and substituted or unsubstituted heterocyclyl;
  wherein R₇ and R₇' are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
R₃ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R₄ is selected from hydrogen, substituted or unsubstituted C$_{1-6}$ alkyl, substituted or unsubstituted C$_{2-6}$ alkenyl and substituted or unsubstituted C$_{2-6}$ alkynyl;
R₅ and R₅' are independently selected from hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —OR₈, —NO₂, —NR₈R₈', —NR₈C(O)R₈', —NR₈S(O)₂R₈', —S(O)₂NR₈R₈', —NR₈C(O)NR₈'R₈'', —SR₈, —S(O)R₈, S(O)₂R₈, —CN, haloalkyl, haloalkoxy, —C(O)OR₈, —C(O)NR₈R₈', —OCH₂CH₂OR₈, —NR₈S(O)₂NR₈'R₈'' and C(CH₃)₂OR₈
  wherein R₈, R₈' and R₈'' are independently selected from hydrogen, unsubstituted C$_{1-6}$ alkyl, unsubstituted C$_{2-6}$ alkenyl, and unsubstituted C$_{2-6}$ alkynyl;
R_c and R_c' are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
alternatively, R_c and R_c' may form with the carbon atom to which they are attached, a substituted or unsubstituted cycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound of general Formula (I²')

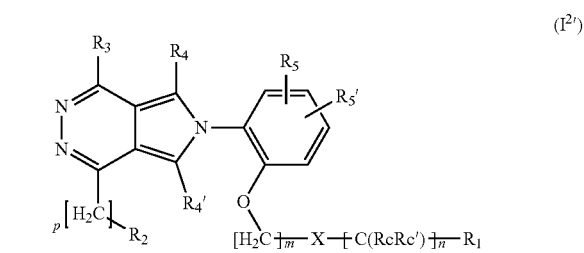

(I²')

wherein m is 0, 1, 2, 3 or 4;

n is 0, 1, 2, 3 or 4;

p is 0, 1, 2, 3 or 4;

X is selected from a bond, substituted or unsubstituted aryl or —$CR_xR_{x'}$—;

$R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_1$ is selected from —$NR_6R_{6'}$ and substituted or unsubstituted N-containing-heterocyclyl;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

$R_2$ is selected from hydrogen, —$NR_7R_{7'}$, —CN, —$CHR_7R_{7'}$ and substituted or unsubstituted heterocyclyl;

wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

$R_3$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_{4'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_5$ and $R_{5'}$ are independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —$OR_8$, —$NO_2$, —$NR_8R_{8'}$, —$NR_8C(O)R_{8'}$, —$NR_8S(O)_2R_{8'}$, —$S(O)_2NR_8R_{8'}$, —$NR_8C(O)NR_8 R_{8''}$, —$SR_8$, —$S(O)R_{8'}$, $S(O)_2R_8$, —CN, haloalkyl, haloalkoxy, —$C(O)OR_8$, —$C(O)NR_8R_{8'}$, —$OCH_2CH_2OR_8$, —$NR_8S(O)_2NR_8R_{8''}$ and $C(CH_3)_2OR_8$ wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

$R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_c$ and $R_{c'}$ may form with the carbon atom to which they are attached, a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

For clarity purposes, the expression "the heterocyclyl in $R_c$—$R_{c'}$" means the heterocyclyl resulting when $R_c$ and $R_{c'}$ form, together with the carbon to which they are attached, a cycle. This heterocyclyl can then be substituted or not.

For clarity purposes, all groups and definitions described in the present description and referring to compounds of general Formula (I), also apply to compounds of general Formula Formulae (I') and ($I^{2'}$), (where applicable), as well as to all the intermediates of synthesis, since compounds of general Formulae Formulae (I') and ($I^{2'}$) are included within the scope of the larger definition of general Formula (I).

For clarity purposes, the general Markush Formula (I)

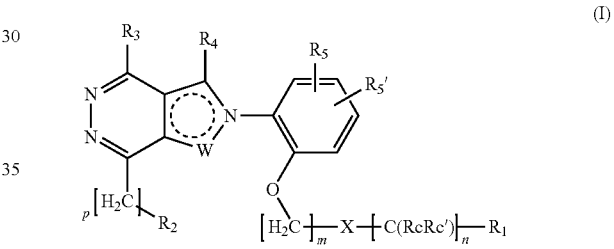

(I)

is equivalent to

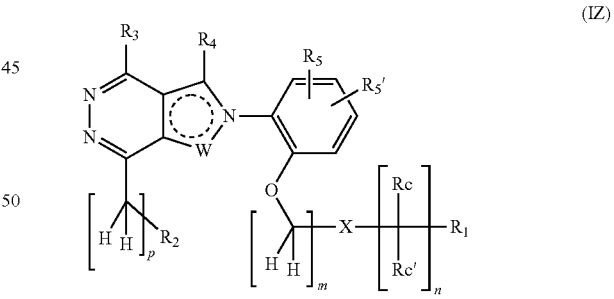

(IZ)

wherein only —$C(R_cR_{c'})$— and —$CH_2$— are included into the brackets, and m, n and p mean the number of times that —$C(R_cR_{c'})$— and —$CH_2$— are repeated, respectively. The same would apply, when applicable, to general Markush Formulae (I') and ($I^{2'}$), as well as to all the intermediates of synthesis.

In addition, and for clarity purposes, it should further be understood that naturally if m is 0, the oxygen and/or X are still present, when applicable, in general Markush Formulae (I), (I') and ($I^{2'}$). In the same way when n is 0, $R_1$ and/or X are still present, when applicable, in general Markush Formulae (I), (I') and ($I^{2'}$). In the same way when p is 0, $R_2$ is still present, when applicable, in general Markush Formulae (I), (I') and (I²') as well as in all the intermediates of synthesis.

For clarity purposes, reference is also made to the following statements below in the definitions of substitutions on alkyl etc. or aryl etc. that "wherein when different radicals $R_1$ to $R_{14''}$ are present simultaneously in Formula (I) they may be identical or different". This statement is reflected in the below general Formula (I³') being derived from and falling into general Formula (I),

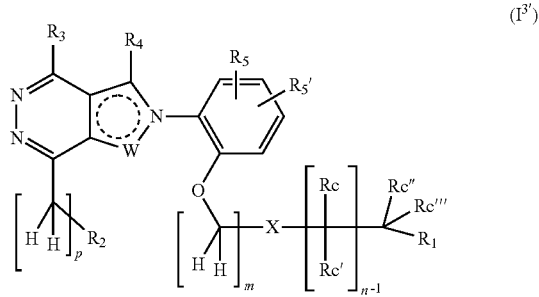

(I³')

wherein $R_1$, $R_2$, $R_3$, $R_4$, $R_5$, $R_c$, $R_{c'}$, X, W, m, n and p are as defined in the description. In addition, $R_{c''}$ and $R_{c'''}$ are added. As said above, this statement is thus reflected in that $R_{c''}$ and $R_{c'''}$ are or could be different from $R_c$ and $R_{c'}$ or not.

The same would be applicable mutatis mutandis for general Formulas like general Formula (I) as well as the other general Formulas (I') to (I²') above, as well as to all the intermediates of synthesis.

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyne, pentyne, hexyne, heptyne, or octyne; or is $C_{2-6}$-alkynyl like ethyne, propyne, butyne, pentyne, or hexyne; or is $C_{2-4}$-alkynyl like ethyne, propyne, butyne, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_kR_{k''}$, —$SR_k$, —$S(O)R_k$, —$S(O)_2R_k$, —$OR_k$, —$C(O)R_k$, —$C(O)OR_k$, —CN, —$C(O)NR_kR_{k'}$, haloalkyl, haloalkoxy, being $R_k$ represented by $R_9$, $R_{11}$, $R_{12}$, or $R_{13}$, (being $R_{k'}$ represented by $R_{9'}$, $R_{11'}$, $R_{12'}$, or $R_{13'}$; being $R_{k''}$ represented by $R_{9''}$, $R_{11''}$, $R_{12''}$, or $R_{13''}$; wherein $R_1$ to $R_{14''}$ and $R_x$ and $R_{x'}$ and $R_c$ and $R_{c'}$ are as defined in the description, and wherein when different radicals $R_1$ to $R_{14''}$ and $R_x$ and $R_{x'}$ and $R_c$ and $R_{c'}$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —$NR_kR_{k'}$, —$OR_k$, —CN, —$SR_k$, haloalkyl, haloalkoxy, being $R_k$ represented by $R_9$, $R_{11}$, $R_{12}$, or $R_{13}$, (being $R_{k'}$ represented by $R_{9'}$, $R_{11'}$, $R_{12'}$, or $R_{13'}$; being $R_{k''}$ represented by $R_{9''}$, $R_{11''}$, $R_{12''}$, or $R_{13''}$; wherein $R_1$ to $R_{14''}$ and $R_x$ and $R_{x'}$ and $R_c$ and $R_{c'}$ are as defined in the description, and wherein when different radicals $R_1$ to $R_{14''}$ and $R_x$ and $R_{x'}$ and $R_c$ and $R_{c'}$ are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH═CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5-or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms selected from the group consisting of nitrogen, oxygen and/or sulfur in the ring; preferably is an aromatic 5 to 18 membered mono or polycyclic heterocyclic ring system of one or two rings of which at least one aromatic ring contains one or more heteroatoms selected from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered mono or polycyclic heterocyclic ring system of one or more rings of which at least one ring —with this (or these) ring(s) then not being aromatic—contains one or more heteroatoms selected from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms selected from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms selected from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms selected from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, tetrahydroisoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—CH$_2$—) groups. Most preferably alkylheterocyclyl is —CH$_2$-pyridine.

In the context of this invention alkylcycloalkyl is understood as meaning an cycloalkyl group being connected to another atom through a C$_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—CH$_2$—) groups. Most preferably alkylcycloalkyl is —CH$_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —R$_k$, —OR$_k$, —CN, —NO$_2$, —NR$_k$R$_{k'}$, —C(O)OR$_k$, NR$_k$C(O)R$_{k'}$, —C(O)NR$_k$R$_{k'}$, —NR$_k$S(O)$_2$R$_{k'}$, =O, —OCH$_2$CH$_2$OH, —NR$_k$C(O)NR$_k$R$_{k''}$, —S(O)$_2$NR$_k$R$_{k'}$, —NR$_k$S(O)$_2$NR$_k$R$_{k''}$, haloalkyl, haloalkoxy, —SR$_k$, —S(O)R$_k$, —S(O)$_2$R$_k$ or C(CH$_3$)OR$_k$; substituted or unsubstituted alkylcycloalkyl, substituted or unsubstituted alkylaryl, substituted or unsubstituted alkyl-heterocyclyl, with R$_k$, R$_{k'}$ and R$_{k''}$ independently being either H or a saturated or unsaturated, linear or branched, substituted or unsubstituted C$_{1-6}$-alkyl; a saturated or unsaturated, linear or branched, substituted or unsubstituted C$_{1-6}$-alkyl; a saturated or unsaturated, linear or branched, substituted or unsubstituted —O—C$_{1-6}$-alkyl (alkoxy); a saturated or unsaturated, linear or branched, substituted or unsubstituted —S—C$_{1-6}$-alkyl; a saturated or unsaturated, linear or branched, substituted or unsubstituted —C(O)—C$_{1-6}$-alkyl-group; a saturated or unsaturated, linear or branched, substituted or unsubstituted —C(O)—O—C$_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being R$_k$ one of R$_{10}$, R$_{11}$, R$_{12}$ or R$_{14}$, (being R$_{k'}$ one of R$_{10'}$, R$_{11'}$, R$_{12'}$ or R$_{14'}$; being R$_{k''}$ one of R$_{10''}$, R$_{11''}$, R$_{12''}$ or R$_{14''}$; wherein R$_1$ to R$_{14'''}$, and R$_x$ and R$_{x'}$ and R$_c$ and R$_{c'}$ are as defined in the description, and wherein when different radicals R$_1$ to R$_{14''}$ and R$_x$ and R$_{x'}$ and R$_c$ and R$_{c'}$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), —R$_k$, —OR$_k$, —CN, —NO$_2$, —NR$_k$R$_{k'''}$, NR$_k$C(O)R$_{k'}$, —NR$_k$S(O)$_2$R$_{k'}$, —S(O)$_2$NR$_k$R$_{k'}$, —NR$_k$C(O)NR$_k$R$_{k''}$, haloalkyl, haloalkoxy, —SR$_k$, —S(O)R$_k$ or S(O)$_2$R$_k$; being R$_k$ one of R$_{10}$, R$_{11}$, R$_{12}$ or R$_{14}$, (being R$_{k'}$ one of R$_{10'}$, R$_{11'}$, R$_{12'}$ or R$_{14'}$; being R$_{k''}$ one of R$_{10''}$, R$_{11''}$, R$_{12''}$ or R$_{14''}$; wherein R$_1$ to R$_{14''}$, and R$_x$ and R$_{x'}$ and R$_c$ and R$_{c'}$ are as defined in the description, and wherein when different radicals R$_1$ to R$_{14''}$ and R$_x$ and R$_{x'}$ and R$_c$ and R$_{c'}$ are present simultaneously in Formula I they may be identical or different.

In connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or with =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH$_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is a N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention. This would especially also apply to the provisos described above so that any mentioning of hydrogen or any "H" in a formula would also cover deuterium or tritium.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I)

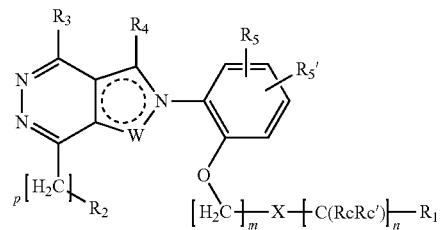

(I)

wherein
m is 0, 1, 2, 3 or 4;
n is 0, 1, 2, 3 or 4;
p is 0, 1, 2, 3 or 4;
W is nitrogen or —C($R_{4'}$)—;
X is selected from a bond, substituted or unsubstituted aryl or —$CR_xR_{x'}$—;
$R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
the alkyl, alkenyl or alkynyl in $R_x$ or $R_{x'}$, if substituted, is substituted with one or more substituent/s selected from —$OR_9$, halogen, —CN, haloalkyl, haloalkoxy and —$NR_9R_{9'}$;
wherein $R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl;
the aryl, heterocyclyl or cycloalkyl, also in alkylaryl, alkylcycloalkyl and alkylheterocyclyl, in $R_x$, if substituted, is substituted with one or more substituent/s selected from halogen, —$R_{10}$, —$OR_{10}$, —$NO_2$, —$NR_{10}R_{10'}$, —$NR_{10}C(O)R_{10'}$, —$NR_{10}S(O)_2R_{10'}$, —$S(O)_2NR_{10}R_{10'}$, —$NR_{10}C(O)NR_{10'}R_{10''}$, —$SR_{10}$, —$S(O)R_{10}$, $S(O)_2R_{10}$, —CN, haloalkyl, haloalkoxy, —$C(O)OR_{10}$, —$C(O)NR_{10}R_{10'}$, —$OCH_2CH_2OR_{10}$, —$NR_{10}S(O)_2NR_{10'}R_{10''}$ and $C(CH_3)_2OR_{10}$;
wherein $R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;
$R_1$ is selected from —$NR_6R_{6'}$ and substituted or unsubstituted N-containing-heterocyclyl;
wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OR_{11}$, —$NR_{11}S(O)_2NR_{11'}R_{11''}$, $C(CH_3)_2OR_{11}$, substituted or unsubstituted alkylaryl, substituted or unsubstituted alkylcycloalkyl and substituted or unsubstituted alkyheterocyclyl;

wherein the alkyl, alkenyl or alkynyl in $R_6$ or $R_{6'}$, if substituted, is substituted with one or more substituent/s selected from —$OR_{11}$, halogen, —CN, haloalkyl, haloalkoxy and —$NR_{11}R_{11'}$;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

$R_2$ is selected from hydrogen, —$NR_7R_{7'}$, —CN, —$CHR_7R_{7'}$ and substituted or unsubstituted heterocyclyl;

wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

wherein said cycloalkyl, aryl or heterocyclyl in $R_2$, $R_7$ or $R_{7'}$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OR_{12}$, —$NR_{12}S(O)_2NR_{12'}R_{12''}$ and $C(CH_3)_2OR_{12}$;

wherein the alkyl, alkenyl or alkynyl in $R_7$ or $R_{7'}$, if substituted, is substituted with one or more substituent/s selected from —$OR_{12}$, halogen, —CN, haloalkyl, haloalkoxy and —$NR_{12}R_{12'}$;

wherein $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;

$R_3$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_{4'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_5$ and $R_{5'}$ are independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —$OR_8$, —$NO_2$, —$NR_8R_{8'}$, —$NR_8C(O)R_{8'}$, —$NR_8S(O)_2R_{8'}$, —$S(O)_2NR_8R_{8'}$, —$NR_8C(O)NR_{8'}R_{8''}$, —$SR_8$, —$S(O)R_8$, $S(O)_2R_8$, —CN, haloalkyl, haloalkoxy, —$C(O)OR_8$, —$C(O)NR_8R_{8'}$, —$OCH_2CH_2OR_8$, —$NR_8S(O)_2NR_{8'}R_{8''}$ and $C(CH_3)_2OR_8$ wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

$R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

alternatively, $R_c$ and $R_{c'}$ may form with the carbon atom to which they are attached, a substituted or unsubstituted cycloalkyl;

the alkyl, alkenyl or alkynyl, other than those defined in $R_x$, $R_{x'}$, $R_6$, $R_{6'}$, $R_7$ or $R_{7'}$, if substituted, is substituted with one or more substituent/s selected from —$OR_{13}$, halogen, —CN, haloalkyl, haloalkoxy and —$NR_{13}R_{13'}$;

wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl, also in alkylaryl, alkylcycloalkyl and alkylheterocyclyl, other than those defined in $R_x$, $R_1$, $R_2$, $R_6$, $R_{6'}$, $R_7$ or $R_{7'}$, if substituted, is substituted with one or more substituent/s selected from halogen, —$R_{14}$, —$OR_{14}$, —$NO_2$, —$NR_{14}R_{14'}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OR_{14}$, —$NR_{14}S(O)_2NR_{14'}R_{14''}$, and $C(CH_3)_2OR_{14}$;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein m is 0, 1, 2, 3 or 4;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein m is 0, 1, 2 or 3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 0, 1, 2, 3 or 4;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
n is 0, 1, 2 or 3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
p is 0, 1, 2, 3 or 4;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
p is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
W is nitrogen or —C($R_{4'}$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is selected from a bond, substituted or unsubstituted aryl or —$CR_xR_{x'}$—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is —C($R_xR_{x'}$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is substituted or unsubstituted aryl
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_x$ is selected from substituted or unsubstituted $C_{1-6}$ alkyl, substituted or unsubstituted aryl, substituted or unsubstituted alkylaryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{x'}$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_{xa}$ independently represents hydrogen, halogen, —$OR_{10}$, —$NR_{10}C(O)R_{10'}$, —CN or —$C(O)NR_{10}R_{10'}$,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from —$NR_6R_{6'}$ and substituted or unsubstituted N-containing-heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from hydrogen, —$NR_7R_{7'}$, —CN, —$CHR_7R_{7'}$ and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_3$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_3$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_4$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{4'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{4'}$ is selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{4'}$ is substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_5$ and $R_{5'}$ are independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —$OR_8$, —$NO_2$, —$NR_8R_{8'}$, —$NR_8C(O)R_{8'}$, —$NR_8S(O)_2R_{8'}$, —$S(O)_2NR_8R_{8'}$, —$NR_8C(O)NR_8R_{8''}$, —$SR_8$, —$S(O)R_{8'}$, $S(O)_2R_8$, —CN, haloalkyl, haloalkoxy, —$C(O)OR_8$, —$C(O)NR_8R_{8'}$, —$OCH_2CH_2OR_8$, —$NR_8S(O)_2NR_8R_{8''}$ and $C(CH_3)_2OR_8$
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_5$ and $R_{5'}$ are independently selected from hydrogen, halogen substituted or unsubstituted heterocyclyl, —$OR_8$, —$NR_8C(O)R_{8'}$, —CN and —$C(O)NR_8R_{8'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_c$ and $R_{c'}$ may form with the carbon atom to which they are attached, a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted alkylaryl, substituted or unsubstituted cycloalkyl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_6$ and $R_{6'}$ are independently selected from hydrogen, substituted or unsubstituted $C_{1-6}$ alkyl, substituted or unsubstituted alkylaryl, substituted or unsubstituted cycloalkyl and substituted or unsubstituted alkylcycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{6a}$ is selected from hydrogen, substituted or unsubstituted $C_{1-6}$ alkyl, substituted or unsubstituted $C_{2-6}$ alkenyl, substituted or unsubstituted $C_{2-6}$ alkynyl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{6a}$ is selected from hydrogen, substituted or unsubstituted $C_{1-6}$ alkyl, and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_7$ and $R_{7'}$ are independently selected from hydrogen, substituted or unsubstituted $C_{1-6}$ alkyl, substituted or unsubstituted aryl and substituted or unsubstituted alkylaryl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_{7a}$ is selected from hydrogen, substituted or unsubstituted alkoxy and substituted or unsubstituted $C_{1-6}$ alkyl.
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_8$, $R_{8'}$ and $R_{8''}$ are independently selected from hydrogen and unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_9$ and $R_{9'}$ are independently selected from unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{10}$, $R_{10'}$ and $R_{10''}$ are independently selected from hydrogen, unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{10}$, $R_{10'}$ and $R_{10''}$ are independently selected from hydrogen and unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{11}$, $R_{11'}$ and $R_{11''}$ are independently selected from hydrogen and unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ and $R_{13'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein X is selected from a bond, substituted or unsubstituted aryl or —$CR_xR_{x'}$—;
  $R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
  $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1, 2, 3 or 4; preferably m is 0, 1, 2 or 3;
and/or
n is 0, 1, 2, 3 or 4; preferably n is 0, 1, 2 or 3;
and/or
p is 0, 1, 2, 3 or 4; preferably p is 0 or 1;
and/or
W is nitrogen or —$C(R_{4'})$—; preferably W is nitrogen or —C(methyl)-;
and/or
X is selected from a bond, substituted or unsubstituted aryl or —$CR_xR_{x'}$—; preferably X is selected from a bond, substituted or unsubstituted phenyl, —CH(methyl)-, —$CH(CH_2$—O-methyl)-, —CH(phenyl)-, —CH(benzyl)-, CH(tetrahydropyrane)-, —CH(pyridine)-, —CH(thiophen)- or —CH(thiazole)-;
and/or
$R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_x$ is selected from substituted or unsubstituted $C_{1-6}$ alkyl, substituted or unsubstituted aryl, substituted or unsubstituted alkylaryl and substituted or unsubstituted heterocyclyl; more preferably $R_x$ is selected from substituted or unsubstituted methyl, substituted or unsubstituted phenyl, substituted or unsubstituted benzyl, substituted or unsubstituted tetrahydropyrane, substituted or unsubstituted pyridine, substituted or unsubstituted thiophen and substituted or unsubstituted thiazole;
and/or
$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{x'}$ is hydrogen;
and/or
$R_{xa}$ independently represents hydrogen, halogen, —$OR_{10}$, —$NR_{10}C(O)R_{10'}$, —CN or —$C(O)NR_{10}R_{10'}$, preferably $R_{xa}$ independently represents hydrogen, fluorine, —OH, —O-ethyl, —NHC(O)-methyl, —$C(O)NH_2$ and —CN;

and/or $R_1$ is selected from —$NR_6R_{6'}$ and substituted or unsubstituted N-containing-heterocyclyl; preferably $R_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, —NH-methyl, —N(methyl)$_2$, —NH-ethyl, —NH-benzyl, —NH$_2$, —NH—CH$_2$-cyclopropyl, —NH-propyl, —NH—CH$_2$CH$_2$O-methyl, —NH-cyclopropyl, —NH-phenethyl, —N(methyl)-benzyl, —NHCH$_2$CH$_2$F and —NHCH$_2$CHF$_2$;

and/or $R_2$ is selected from hydrogen, —$NR_7R_{7'}$, —CN, —CHR$_7$R$_{7'}$ and substituted or unsubstituted heterocyclyl; preferably $R_2$ is selected from hydrogen, substituted or unsubstituted methyl, substituted or unsubstituted isopropyl, substituted or unsubstituted —NH-methyl, substituted or unsubstituted —N(methyl)$_2$, substituted or unsubstituted —N(ethyl)(methyl), substituted or unsubstituted —NH-phenyl, substituted or unsubstituted —NH-benzyl, substituted or unsubstituted —N(methyl)(benzyl), substituted or unsubstituted —N(methyl)(propyl), substituted or unsubstituted morpholine, substituted or unsubstituted oxadiazole, substituted or unsubstituted azetidine, substituted or unsubstituted pyrrolidine and —CN; preferably $R_2$ is selected from hydrogen, methyl, isopropyl, —NH-methyl, —N(methyl)$_2$, —N(ethyl)(methyl), —NH-phenyl, —NH-benzyl, —N(methyl)(benzyl), —N(methyl)(CH$_2$CH$_2$—OH), —N(methyl)(CH$_2$CH$_2$—O-methyl), —N(methyl)(CH$_2$CH$_2$CH$_2$—OH), —N(methyl)(CH$_2$CH$_2$—N(methyl)$_2$), substituted or unsubstituted morpholine, substituted or unsubstituted oxadiazole, substituted or unsubstituted azetidine, substituted or unsubstituted pyrrolidine and —CN;

and/or $R_3$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably $R_3$ is selected from hydrogen and substituted or unsubstituted C$_{1-6}$ alkyl; more preferably $R_3$ is selected from hydrogen and substituted or unsubstituted methyl;

and/or $R_4$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably $R_4$ is selected from hydrogen and substituted or unsubstituted C$_{1-6}$ alkyl; more preferably $R_4$ is selected from hydrogen and substituted or unsubstituted methyl;

and/or $R_{4'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably $R_{4'}$ is substituted or unsubstituted methyl;

and/or $R_5$ and $R_{5'}$ are independently selected from hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —OR$_8$, —NO$_2$, —NR$_8$R$_{8'}$, —NR$_8$C(O)R$_{8'}$, —NR$_8$S(O)$_2$R$_{8'}$, —S(O)$_2$NR$_8$R$_{8'}$, —NR$_8$C(O)NR$_8$R$_{8''}$, —SR$_8$, —S(O)R$_8$, S(O)$_2$R$_8$, —CN, haloalkyl, haloalkoxy, —C(O)OR$_8$, —C(O)NR$_8$R$_{8'}$, —OCH$_2$CH$_2$OR$_8$, —NR$_8$S(O)$_2$NR$_8$R$_{8'}$ and C(CH$_3$)$_2$OR$_8$; preferably $R_5$ and $R_{5'}$ are independently selected from hydrogen, halogen, substituted or unsubstituted heterocyclyl, —OR$_8$, —NR$_8$C(O)R$_{8'}$, —CN and —C(O)NR$_8$R$_{8'}$; more preferably $R_5$ and $R_{5'}$ are independently selected from hydrogen, bromine, substituted or unsubstituted pyrrolidine-2-one, substituted or unsubstituted —NHC(O)-methyl, —OH, substituted or unsubstituted —O-methyl, substituted or unsubstituted —O-ethyl, —CN, —C(O)NH$_2$ and substituted or unsubstituted —C(O)N(CH$_3$)$_2$;

and/or $R_6$ and $R_{6'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_6$ and $R_{6'}$ are independently selected from hydrogen, substituted or unsubstituted C$_{1-6}$ alkyl, substituted or unsubstituted alkylaryl, substituted or unsubstituted cycloalkyl and substituted or unsubstituted alkylcycloalkyl; more preferably $R_6$ and $R_{6'}$ are independently selected from hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl and substituted or unsubstituted —CH$_2$— cyclopropyl;

and/or $R_{6a}$ is selected from hydrogen, substituted or unsubstituted C$_{1-6}$ alkyl, substituted or unsubstituted C$_{2-6}$ alkenyl, substituted or unsubstituted C$_{2-6}$ alkynyl and substituted or unsubstituted alkylaryl; preferably $R_{6a}$ is selected from hydrogen, substituted or unsubstituted C$_{1-6}$ alkyl and substituted or unsubstituted alkylaryl; more preferably $R_{6a}$ is selected from hydrogen, substituted or unsubstituted methyl, substituted or unsubstituted benzyl and substituted or unsubstituted phenethyl;

and/or $R_7$ and $R_{7'}$ are independently selected from hydrogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_7$ and $R_{7'}$ are independently selected from hydrogen, substituted or unsubstituted C$_{1-6}$ alkyl, substituted or unsubstituted aryl and substituted or unsubstituted alkylaryl; more preferably $R_7$ and $R_{7'}$ are independently selected from hydrogen, substituted or unsubstituted methyl, substituted or unsubstituted ethyl, substituted or unsubstituted propyl, substituted or unsubstituted phenyl and substituted or unsubstituted benzyl; more preferably $R_7$ and $R_{7'}$ are independently selected from hydrogen, substituted or unsubstituted methyl, substituted or unsubstituted ethyl, substituted or unsubstituted —CH$_2$CH$_2$OH, substituted or unsubstituted —CH$_2$CH$_2$O-methyl, substituted or unsubstituted —CH$_2$CH$_2$CH$_2$OH, substituted or unsubstituted —CH$_2$CH$_2$N(methyl)$_2$, substituted or unsubstituted phenyl and substituted or unsubstituted benzyl;

and/or $R_{7a}$ is selected from hydrogen, substituted or unsubstituted alkoxy and substituted or unsubstituted C$_{1-6}$ alkyl, preferably $R_{7a}$ is hydrogen, substituted or unsubstituted —O-methyl or substituted or unsubstituted methyl;

and/or $R_8$, $R_{8'}$, and $R_{8''}$, are independently selected from hydrogen, unsubstituted $C_{1-6}$ alkyl, unsubstituted $C_{2-6}$ alkenyl and unsubstituted $C_{2-6}$ alkynyl; preferably $R_8$, $R_{8'}$ and $R_{8''}$, are independently selected from hydrogen and unsubstituted $C_{1-6}$ alkyl; more preferably $R_8$, $R_{8'}$ and $R_{8''}$, are independently selected from hydrogen, unsubstituted methyl and unsubstituted ethyl;

and/or $R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably, $R_c$ and $R_{c'}$ are both hydrogen;

and/or $R_c$ and $R_{c'}$ may form with the carbon atom to which they are attached, a substituted or unsubstituted cycloalkyl;

and/or $R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl; preferably $R_9$ is unsubstituted methyl;

and/or $R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl; preferably $R_{10}$, $R_{10'}$ and $R_{10''}$ are independently selected from hydrogen and unsubstituted $C_{1-6}$ alkyl; more preferably $R_{10}$ and $R_{10'}$ are independently selected from hydrogen, unsubstituted methyl and unsubstituted ethyl;

and/or $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl; preferably $R_{11}$ is unsubstituted methyl;

and/or $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl; preferably $R_{12}$, $R_{12'}$ and $R_{12''}$ are independently selected from hydrogen and unsubstituted $C_{1-6}$ alkyl; more preferably $R_{12}$, $R_{12'}$ and $R_{12''}$ are independently selected from hydrogen and unsubstituted methyl;

and/or $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein m is 0, 1, 2, 3 or 4;

and/or n is 0, 1, 2, 3 or 4;

and/or p is 0, 1, 2, 3 or 4;

and/or

W is nitrogen or —C($R_{4'}$)—;

and/or

X is selected from a bond, substituted or unsubstituted aryl or —$CR_xR_{x'}$—;

wherein the aryl is selected from phenyl, naphthyl, or anthracene; preferably is naphthyl and phenyl; preferably the aryl is phenyl;

and/or $R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

wherein the alkyl is $C_{1-6}$ alkyl like methyl, ethyl, propyl, butyl, pentyl, hexyl, isopropyl, or 2-methylpropyl; more preferably the alkyl is methyl;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-8}$ cycloalkyl like cyclopropyl, cyclobutyl, cyclopentyl or cyclohexyl;

and/or the aryl is selected from phenyl, naphthyl, or anthracene; preferably is naphthyl and phenyl; preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; preferably the heterocyclyl is tetrahydropyrane, pyridine, thiophen or thiazole;

and/or $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl,pentyl, hexyl, isopropyl, or 2-methylpropyl, and/or the $C_{2-6}$-alkenyl is preferably selected from ethylene, propylene, butylene, pentylene, hexylene, isopropylene and isobutylene;

and/or the $C_{2-6}$ alkynyl is preferably selected from ethyne, propyne, butyne, pentyne, hexyne, isopropyne and isobutyne;

and/or $R_1$ is selected from $-NR_6R_6$ and substituted or unsubstituted N-containing-heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; even more preferably the heterocyclyl is pyrrolidine, piperidin, tetrahydroisoquinoline, tetrahydroquinoline, azetidine or morpholine;

and/or $R_2$ is selected from hydrogen, $-NR_7R_{7'}$, $-CN$, $-CHR_7R_{7'}$ and substituted or unsubstituted heterocyclyl;

wherein the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; even more preferably the heterocyclyl is morpholine, oxadiazole, azetidine or pyrrolidine;

and/or $R_3$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_4$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$ alkynyl is preferably selected from ethyne, propyne, butyne, pentyne, hexyne, isopropyne and isobutyne;

and/or $R_{4'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_5$ and $R_{5'}$ are independently selected from hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, $-OR_8$, $-NO_2$, $-NR_8R_{8'}$, $-NR_8C(O)R_{8'}$, $-NR_8S(O)_2R_{8'}$, $-S(O)_2NR_8R_{8'}$, $-NR_8C(O)NR_8R_{8''}$, $-SR_8$, $-S(O)R_8$, $S(O)_2R_8$, $-CN$, haloalkyl, haloalkoxy, $-C(O)OR_8$, $-C(O)NR_8R_{8'}$, $-OCH_2CH_2OR_8$, $-NR_8S(O)_2NR_8R_{8''}$ and $C(CH_3)_2OR_8$;

wherein
the alkyl is $C_{1-6}$ alkyl like methyl, ethyl, propyl, butyl, pentyl, hexyl, isopropyl, or 2-methylpropyl;
and/or
the $C_{1-6}$ alkyl is preferably selected from methyl, ethyl, propyl, butyl,pentyl, hexyl, isopropyl, or 2-methylpropyl;
and/or
the $C_{2-6}$ alkenyl is preferably selected from ethylene, propylene, butylene, pentylene, hexylene, isopropylene and isobutylene;
and/or
the $C_{2-6}$ alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
the aryl is selected from phenyl, naphthyl, or anthracene; preferably is and phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline; even more preferably the heterocyclyl is pyrrolidone;
and/or
$R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl,pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
$R_c$ and $R_{c'}$ may form with the carbon atom to which they are attached, a substituted or unsubstituted cycloalkyl;

wherein
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
$R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
wherein
the alkyl is $C_{1-6}$ alkyl like methyl, ethyl, propyl, butyl, pentyl, hexyl, isopropyl, or 2-methylpropyl; preferably the alkyl is methyl or ethyl;
and/or
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl, ethyl or propyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; even preferably the cycloalkyl is cyclopropyl;
and/or
the aryl is selected from phenyl, naphthyl, or anthracene; preferably is naphthyl and phenyl; more preferably the aryl is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;

and/or $R_{6a}$ is selected from hydrogen, substituted or unsubstituted $C_{1-6}$ alkyl and substituted or unsubstituted alkylaryl;

wherein
the alkyl is $C_{1-6}$ alkyl like methyl, ethyl, propyl, butyl, pentyl, hexyl, isopropyl, or 2-methylpropyl; preferably the alkyl is methyl or ethyl;
and/or
the $C_{1-6}$ alkyl is preferably selected from methyl, ethyl, propyl, butyl,pentyl, hexyl, isopropyl, or 2-methylpropyl; preferably the $C_{1-6}$ alkyl is methyl
and/or
the aryl is selected from phenyl, naphthyl, or anthracene; preferably is naphthyl and phenyl; preferably the aryl is phenyl;
and/or $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

wherein
the alkyl is $C_{1-6}$ alkyl like methyl, ethyl, propyl, butyl, pentyl, hexyl, isopropyl, or 2-methylpropyl; preferably the alkyl is methyl;
and/or
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl, ethyl or propyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
the aryl is selected from phenyl, naphthyl, or anthracene; preferably is naphthyl and phenyl; more preferably the aryl is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;
and/or $R_{7a}$ is selected from hydrogen, substituted or unsubstituted alkoxy and substituted or unsubstituted $C_{1-6}$ alkyl.

Wherein
the alkyl (in alkoxy) is $C_{1-6}$ alkyl like methyl, ethyl, propyl, butyl,pentyl, hexyl, isopropyl, or 2-methylpropyl; preferably the alkyl is methyl;
and/or
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

$R_8$, $R_{8'}$ and $R_{8''}$ are independently selected from hydrogen, unsubstituted $C_{1-6}$ alkyl, unsubstituted $C_{2-6}$ alkenyl and unsubstituted $C_{2-6}$ alkynyl;

wherein
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl or ethyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or $R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl;

wherein
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene, hexylene, isopropylene and isobutylene;
and/or
the $C_{2-6}$ alkynyl is preferably selected from ethyne, propyne, butyne, pentyne, hexyne, isopropyne and isobutyne;
and/or $R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

wherein
the alkyl is $C_{1-6}$ alkyl like methyl, ethyl, propyl, butyl, pentyl, hexyl, isopropyl, or 2-methylpropyl;
and/or
the $C_{1-6}$ alkyl is preferably selected from methyl, ethyl, propyl, butyl,pentyl, hexyl, isopropyl, or 2-methylpropyl, more preferably the $C_{1-6}$ alkyl is methyl or ethyl;
and/or
the $C_{2-6}$-alkenyl is preferably selected from ethylene, propylene, butylene, pentylene, hexylene, isopropylene and isobutylene;
and/or the $C_{2-6}$-alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
the aryl is selected from phenyl, naphthyl, or anthracene; preferably is naphthyl and phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;
and/or
$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
wherein
the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene, hexylene, isopropylene and isobutylene;
and/or
the $C_{2-6}$ alkynyl is preferably selected from ethyne, propyne, butyne, pentyne, hexyne, isopropyne and isobutyne;
and/or
$R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;
wherein
the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;
wherein
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
$R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;
wherein
the alkyl is $C_{1-6}$ alkyl like methyl, ethyl, propyl, butyl, pentyl, hexyl, isopropyl, or 2-methylpropyl;
and/or
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or
the aryl is selected from phenyl, naphthyl, or anthracene; preferably is naphthyl and phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention,
  the alkyl is $C_{1-6}$ alkyl like methyl, ethyl, propyl, butyl, pentyl, hexyl, isopropyl, or 2-methylpropyl; more preferably the alkyl is methyl;
  and/or
  the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;
  and/or
  the $C_{2-6}$-alkenyl is preferably selected from ethylene, propylene, butylene, pentylene, hexylene, isopropylene and isobutylene;
  and/or
  the $C_{2-6}$-alkynyl is preferably selected from ethyne, propyne, butyne, pentyne, hexyne, isopropyne and isobutyne;
  and/or
  the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
  and/or
  the aryl is selected from phenyl, naphthyl, or anthracene; preferably is naphthyl and phenyl; preferably the aryl is phenyl;
  and/or
  the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; preferably the heterocyclyl is tetrahydropyrane, pyridine, thiophen or thiazole;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention,
  the $C_{1-6}$ alkyl is preferably selected from methyl, ethyl, propyl, butyl,pentyl, hexyl, isopropyl, or 2-methylpropyl;
  and/or
  the $C_{2-6}$-alkenyl is preferably selected from ethylene, propylene, butylene, pentylene, hexylene, isopropylene and isobutylene;
  and/or
  the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_c$ and $R_{c'}$ as defined in any of the embodiments of the present invention,
  the $C_{1-6}$ alkyl is preferably selected from methyl, ethyl, propyl, butyl,pentyl, hexyl, isopropyl, or 2-methylpropyl;
  and/or
  the $C_{2-6}$-alkenyl is preferably selected from ethylene, propylene, butylene, pentylene, hexylene, isopropylene and isobutylene;
  and/or
  the $C_{2-6}$-alkynyl is preferably selected from ethyne, propyne, butyne, pentyne, hexyne, isopropyne and isobutyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_c$ and $R_{c'}$ as defined in any of the embodiments of the present invention,
  the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-8}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$ as defined in any of the embodiments of the present invention,
  the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; even more preferably the heterocyclyl is pyrrolidine, piperidin, tetrahydroisoquinoline, tetrahydroquinoline, azetidine or morpholine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention, the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; even more preferably the heterocyclyl is morpholine, oxadiazole, azetidine or pyrrolidine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ as defined in any of the embodiments of the present invention, the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{4'}$ as defined in any of the embodiments of the present invention, the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention, the alkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl,pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the C$_{2-6}$ alkynyl is preferably selected from ethyne, propyne, butyne, pentyne, hexyne, isopropyne and isobutyne;

and/or the cycloalkyl is C$_{3-8}$ cycloalkyl like cyclopropyl, cyclobutyl, cyclopentyl, cyclohexyl, cycloheptyl, or cyclooctyl; preferably is C$_{3-7}$ cycloalkyl like cyclopropyl, cyclobutyl, cyclopentyl, cyclohexyl, or cycloheptyl; more preferably from C$_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline; even more preferably the heterocyclyl is pyrrolidone;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R$_6$ and R$_{6'}$ as defined in any of the embodiments of the present invention, the alkyl is C$_{1-6}$ alkyl like methyl, ethyl, propyl, butyl, pentyl, hexyl, isopropyl, or 2-methylpropyl; preferably the alkyl is methyl or ethyl;

and/or the C$_{1-6}$ alkyl is preferably selected from methyl, ethyl, propyl, butyl,pentyl, hexyl, isopropyl, or 2-methylpropyl, more preferably the C$_{1-6}$ alkyl is methyl, ethyl or propyl;

and/or the C$_{2-6}$-alkenyl is preferably selected from ethylene, propylene, butylene, pentylene, hexylene, isopropylene and isobutylene;

and/or the C$_{2-6}$ alkynyl is preferably selected from ethyne, propyne, butyne, pentyne, hexyne, isopropyne and isobutyne;

and/or the cycloalkyl is C$_{3-8}$ cycloalkyl like cyclopropyl, cyclobutyl, cyclopentyl, cyclohexyl, cycloheptyl, or cyclooctyl; preferably is C$_{3-7}$ cycloalkyl like cyclopropyl, cyclobutyl, cyclopentyl, cyclohexyl, or cycloheptyl; more preferably from C$_{3-6}$ cycloalkyl like cyclopropyl, cyclobutyl, cyclopentyl or cyclohexyl; even preferably the cycloalkyl is cyclopropyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R$_{6a}$ as defined in any of the embodiments of the present invention, the alkyl is C$_{1-6}$ alkyl like methyl, ethyl, propyl, butyl, pentyl, hexyl, isopropyl, or 2-methylpropyl; preferably the alkyl is methyl or ethyl;

and/or the C$_{1-6}$ alkyl is preferably selected from methyl, ethyl, propyl, butyl,pentyl, hexyl, isopropyl, or 2-methylpropyl; preferably the C$_{1-6}$ alkyl is methyl and/or the aryl is selected from phenyl, naphthyl, or anthracene; preferably is naphthyl and phenyl; preferably the aryl is phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R$_7$ and R$_{7'}$ as defined in any of the embodiments of the present invention, the alkyl is C$_{1-6}$ alkyl like methyl, ethyl, propyl, butyl, pentyl, hexyl, isopropyl, or 2-methylpropyl; preferably the alkyl is methyl;

and/or the C$_{1-6}$ alkyl is preferably selected from methyl, ethyl, propyl, butyl,pentyl, hexyl, isopropyl, or 2-methylpropyl, more preferably the C$_{1-6}$ alkyl is methyl, ethyl or propyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl; more preferably the aryl is phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{7a}$ as defined in any of the embodiments of the present invention, the alkyl (in alkoxy) is $C_{1-6}$ alkyl like methyl, ethyl, propyl, butyl, pentyl, hexyl, isopropyl, or 2-methylpropyl; preferably the alkyl is methyl;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$, $R_{8'}$ and $R_{8''}$ as defined in any of the embodiments of the present invention, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$ alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ and $R_{9'}$ as defined in any of the embodiments of the present invention, the $C_{1-6}$ alkyl is preferably selected from methyl, ethyl, propyl, butyl, pentyl, hexyl, isopropyl, or 2-methylpropyl, more preferably the $C_{1-6}$ alkyl is methyl;

and/or the $C_{2-6}$-alkenyl is preferably selected from ethylene, propylene, butylene, pentylene, hexylene, isopropylene and isobutylene;

and/or the $C_{2-6}$ alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$, $R_{10'}$ and $R_{10''}$ as defined in any of the embodiments of the present invention, the alkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl, more preferably the $C_{1-6}$ alkyl is methyl or ethyl;

and/or the $C_{2-6}$-alkenyl is preferably selected from ethylene, propylene, butylene, pentylene, hexylene, isopropylene and isobutylene;

and/or the $C_{2-6}$ alkynyl is preferably selected from ethyne, propyne, butyne, pentyne, hexyne, isopropyne and isobutyne;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or the aryl is selected from phenyl, naphthyl, or anthracene; preferably is naphthyl and phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention, the $C_1$ alkyl is preferably selected from methyl, ethyl, propyl, butyl,pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention, the $C_{1-6}$ alkyl is preferably selected from methyl, ethyl, propyl, butyl,pentyl, hexyl, isopropyl, or 2-methylpropyl, more preferably the $C_{1-6}$ alkyl is methyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13'}$ as defined in any of the embodiments of the present invention, the $C_{1-6}$ alkyl is preferably selected from methyl, ethyl, propyl, butyl,pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention, the alkyl is $C_{1-6}$ alkyl like methyl, ethyl, propyl, butyl, pentyl, hexyl, isopropyl, or 2-methylpropyl;
and/or
the $C_{1-6}$ alkyl is preferably selected from methyl, ethyl, propyl, butyl,pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-8}$ cycloalkyl like cyclopropyl, cyclobutyl, cyclopentyl or cyclohexyl;
and/or
the aryl is selected from phenyl, naphthyl, or anthracene; preferably is naphthyl and phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from oxazepan, pyrrolidine, imidazole, oxadiazole, tetrazole, azetidine, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole, oxopyrrolidine, pyrimidine, benzodioxolane, benzodioxane, carbazole and quinazoline;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1, 2, 3 or 4; preferably m is 0, 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 0, 1, 2, 3 or 4; preferably n is 0, 1, 2 or 3;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0, 1, 2, 3 or 4; preferably p is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein W is nitrogen or —C($R_{4'}$)—;, preferably nitrogen or —C(methyl)-;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from a bond, substituted or unsubstituted aryl or —$CR_xR_{x'}$—; preferably X is selected from a bond, substituted or unsubstituted phenyl, —CH(methyl)-, —CH($CH_2$—O-methyl)-, —CH(phenyl)-, —CH(benzyl)-, CH(tetrahydropyrane)-, —CH(pyridine)-, —CH(thiophen)- or —CH(thiazole)-;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_x$ is selected from substituted or unsubstituted $C_{1-6}$ alkyl, substituted or unsubstituted aryl, substituted or unsubstituted alkylaryl and substituted or unsubstituted heterocyclyl; more preferably $R_x$ is selected from substituted or unsubstituted methyl, substituted or unsubstituted phenyl, substituted or unsubstituted benzyl, substituted or unsubstituted tetrahydropyrane, substituted or unsubstituted pyridine, substituted or unsubstituted thiophen and substituted or unsubstituted thiazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; preferably $R_{x'}$ is hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{xa}$ independently represents hydrogen, halogen, —$OR_{10}$, —$NR_{10}C(O)R_{10'}$, —CN or —$C(O)NR_{10}R_{10'}$, preferably $R_{xa}$ independently represents hydrogen, fluorine, —OH, —O-ethyl, —NHC(O)-methyl, —$C(O)NH_2$ and —CN;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_1$ is selected from —$NR_6R_{6'}$ and substituted or unsubstituted N-containing-heterocyclyl; preferably $R_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, substituted or unsubstituted —NH-methyl, substituted or unsubstituted —$N(methyl)_2$, substituted or unsubstituted —NH-ethyl, substituted or unsubstituted —NH-benzyl, —$NH_2$, substituted or unsubstituted —NH—CH$_2$-cyclopropyl, substituted or unsubstituted —NH-propyl, substituted or unsubstituted NH—CH$_2$CH$_2$O-methyl, substituted or unsubstituted —NH-cyclopropyl, substituted or unsubstituted —NH-phenethyl, substituted or unsubstituted —N(methyl)-benzyl, substituted or unsubstituted —NHCH$_2$CH$_2$F and substituted or unsubstituted —NHCH$_2$CHF$_2$; more preferably R$_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, —NH-methyl, —N(methyl)$_2$, —NH-ethyl, —NH-benzyl, —NH$_2$, —NH—CH$_2$-cyclopropyl, —NH-propyl, —NH—CH$_2$CH$_2$O-methyl, —NH-cyclopropyl, —NH-phenethyl, —N(methyl)-benzyl, —NHCH$_2$CH$_2$F and —NHCH$_2$CHF$_2$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_2$ is selected from hydrogen, —NR$_7$R$_{7'}$, —CN, —CHR$_7$R$_{7'}$ and substituted or unsubstituted heterocyclyl; preferably R$_2$ is selected from hydrogen, substituted or unsubstituted methyl, substituted or unsubstituted isopropyl, substituted or unsubstituted —NH-methyl, substituted or unsubstituted —N(methyl)$_2$, substituted or unsubstituted —N(ethyl)(methyl), substituted or unsubstituted —NH-phenyl, substituted or unsubstituted —NH-benzyl, substituted or unsubstituted —N(methyl)(benzyl), substituted or unsubstituted —N(methyl)(propyl), substituted or unsubstituted morpholine, substituted or unsubstituted oxadiazole, substituted or unsubstituted azetidine, substituted or unsubstituted pyrrolidine and —CN; preferably R$_2$ is selected from hydrogen, methyl, isopropyl, —NH-methyl, —N(methyl)$_2$, —N(ethyl)(methyl), —NH-phenyl, —NH-benzyl, —N(methyl)(benzyl), —N(methyl)(ethyl-OH), —N(methyl)(ethyl-O-methyl), —N(methyl)(propyl-OH), —N(methyl)(ethyl-N(methyl)$_2$), substituted or unsubstituted morpholine, substituted or unsubstituted oxadiazole, substituted or unsubstituted azetidine, substituted or unsubstituted pyrrolidine and —CN;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_3$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably R$_3$ is selected from hydrogen and substituted or unsubstituted C$_{1-6}$ alkyl; more preferably R$_3$ is selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_4$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably R$_4$ is selected from hydrogen and substituted or unsubstituted C$_{1-6}$ alkyl; more preferably R$_4$ is selected from hydrogen and substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_{4'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl; preferably R$_{4'}$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_5$ and R$_{5'}$ are independently selected from hydrogen, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —OR$_8$, —NO$_2$, —NR$_8$R$_{8'}$, —NR$_8$C(O)R$_{8'}$, —NR$_8$S(O)$_2$R$_{8'}$, —S(O)$_2$NR$_8$R$_{8'}$, —NR$_8$C(O)NR$_8$R$_{8''}$, —SR$_8$, —S(O)R$_{8'}$, S(O)$_2$R$_8$, —CN, haloalkyl, haloalkoxy, —C(O)OR$_8$, —C(O)NR$_8$R$_{8'}$, —OCH$_2$CH$_2$OR$_8$, —NR$_8$S(O)$_2$NR$_8$R$_{8''}$ and C(CH$_3$)$_2$OR$_8$; preferably R$_5$ and R$_{5'}$ are independently selected from hydrogen, halogen, substituted or unsubstituted heterocyclyl, —OR$_8$, —NR$_8$C(O)R$_{8'}$, —CN and —C(O)NR$_8$R$_{8'}$; more preferably R$_5$ and R$_{5'}$ are independently selected from hydrogen, bromine, substituted or unsubstituted pyrrolidine-2-one, substituted or unsubstituted —NHC(O)-methyl, —OH, substituted or unsubstituted —O-methyl, substituted or unsubstituted —O-ethyl, —CN, —C(O)NH$_2$ and substituted or unsubstituted —C(O)N(CH$_3$)$_2$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein R$_6$ and R$_{6'}$ are independently selected from hydrogen, substituted or unsubstituted C$_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_6$ and $R_{6'}$ are independently selected from hydrogen, substituted or unsubstituted $C_{1-6}$ alkyl, substituted or unsubstituted alkylaryl, substituted or unsubstituted cycloalkyl and substituted or unsubstituted alkylcycloalkyl; more preferably $R_6$ and $R_{6'}$ are independently selected from hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl and substituted or unsubstituted —$CH_2$-cyclopropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{6a}$ is selected from hydrogen, substituted or unsubstituted $C_{1-6}$ alkyl and substituted or unsubstituted alkylaryl, preferably $R_{6a}$ is selected from hydrogen, substituted or unsubstituted methyl, substituted or unsubstituted benzyl and substituted or unsubstituted phenethyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl; preferably $R_7$ and $R_{7'}$ are independently selected from hydrogen, substituted or unsubstituted $C_{1-6}$ alkyl, substituted or unsubstituted aryl and substituted or unsubstituted alkylaryl; more preferably $R_7$ and $R_{7'}$ are independently selected from hydrogen, substituted or unsubstituted methyl, substituted or unsubstituted ethyl, substituted or unsubstituted propyl, substituted or unsubstituted phenyl and substituted or unsubstituted benzyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{7a}$ is selected from hydrogen, substituted or unsubstituted alkoxy and substituted or unsubstituted $C_{1-6}$ alkyl; preferably $R_{7a}$ is selected from hydrogen, substituted or unsubstituted methyl or substituted or unsubstituted —O-methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_8$, $R_{8'}$ and $R_{8''}$ are independently selected from hydrogen, unsubstituted $C_{1-6}$ alkyl, unsubstituted $C_{2-6}$ alkenyl and unsubstituted $C_{2-6}$ alkynyl; preferably $R_8$, $R_{8'}$ and $R_{8''}$ are independently selected from hydrogen and unsubstituted $C_{1-6}$ alkyl; more preferably $R_8$, $R_{8'}$ and $R_{8''}$ are independently selected from hydrogen, unsubstituted methyl and unsubstituted ethyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_c$ and $R_{c'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl; preferably, $R_c$ and $R_{c'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_c$ and $R_{c'}$ form with the carbon atom to which they are attached, a substituted or unsubstituted cycloalkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl; preferably $R_9$ is unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl; preferably $R_{10}$, $R_{10'}$ and $R_{10''}$ are independently selected from hydrogen and unsubstituted $C_{1-6}$ alkyl; more preferably $R_{10}$ and $R_{10'}$ are independently selected from hydrogen, and unsubstituted methyl and unsubstituted ethyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl; preferably $R_{11}$ is unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl; preferably $R_{12}$, $R_{12'}$ and $R_{12''}$ are independently selected from hydrogen and unsubstituted $C_{1-6}$ alkyl; more preferably $R_{12}$, $R_{12'}$ and $R_{12''}$ are independently selected from hydrogen and unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1, 2 or 3;
and
n is 0, 1, 2 or 3;
and
p is 0 or 1;
and
W is nitrogen or —C(methyl)-;
and
X is selected from a bond, substituted or unsubstituted phenyl, —CH(methyl)-, —CH(CH$_2$—O-methyl)-, —CH(phenyl)-, —CH(benzyl)-, CH(tetrahydropyrane)-, —CH(pyridine)-, —CH(thiophen)- or —CH(thiazole)-;
and
$R_x$ is selected from substituted or unsubstituted methyl, substituted or unsubstituted phenyl, substituted or unsubstituted benzyl, substituted or unsubstituted tetrahydropyrane, substituted or unsubstituted pyridine, substituted or unsubstituted thiophen and substituted or unsubstituted thiazole;
and
$R_{x'}$ is hydrogen;
and
$R_{xa}$ independently represents hydrogen, fluorine, —OH, —O-ethyl, —NHC(O)-methyl, —C(O)NH$_2$ and —CN
and
$R_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, —NH-methyl, —N(methyl)$_2$, —NH-ethyl, —NH-benzyl, —NH$_2$, —NH—CH$_2$-cyclopropyl, —NH-propyl, —NH—CH$_2$CH$_2$O-methyl, —NH-cyclopropyl, —NH-phenethyl, —N(methyl)-benzyl, —NHCH$_2$CH$_2$F and —NHCH$_2$CHF$_2$;
and
$R_2$ is selected from hydrogen, substituted or unsubstituted methyl, substituted or unsubstituted isopropyl, substituted or unsubstituted —NH-methyl, substituted or unsubstituted —N(methyl)$_2$, substituted or unsubstituted —N(ethyl)(methyl), substituted or unsubstituted —NH-phenyl, substituted or unsubstituted —NH-benzyl, substituted or unsubstituted —N(methyl)(benzyl), substituted or unsubstituted —N(methyl)(propyl), substituted or unsubstituted morpholine, substituted or unsubstituted oxadiazole, substituted or unsubstituted azetidine, substituted or unsubstituted pyrrolidine and —CN; preferably $R_2$ is selected from hydrogen, methyl, isopropyl, —NH-methyl, —N(methyl)$_2$, —N(ethyl)(methyl), —NH-phenyl, —NH-benzyl, —N(methyl)(benzyl), —N(methyl)(ethyl-OH), —N(methyl)(ethyl-O-methyl), —N(methyl)(propyl-OH), —N(methyl)(ethyl-N(methyl)$_2$), substituted or unsubstituted morpholine, substituted or unsubstituted oxadiazole, substituted or unsubstituted azetidine, substituted or unsubstituted pyrrolidine and —CN;
and
$R_3$ is selected from hydrogen and substituted or unsubstituted methyl;
and
$R_4$ is selected from hydrogen and substituted or unsubstituted methyl;

and $R_{4'}$ is substituted or unsubstituted methyl;
and $R_5$ and $R_{5'}$ are independently selected from hydrogen, bromine, substituted or unsubstituted pyrrolidine-2-one, substituted or unsubstituted —NHC(O)-methyl, —OH, substituted or unsubstituted —O-methyl, substituted or unsubstituted —O— ethyl, —CN, —C(O)NH$_2$ and substituted or unsubstituted —C(O)N(CH$_3$)$_2$;
and $R_6$ and $R_{6'}$ are independently selected from hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl and substituted or unsubstituted —CH$_2$-cyclopropyl;
and $R_{6a}$ is selected from hydrogen, substituted or unsubstituted methyl, substituted or unsubstituted benzyl and substituted or unsubstituted phenethyl;
and $R_7$ and $R_{7'}$ are independently selected from hydrogen, substituted or unsubstituted methyl, substituted or unsubstituted ethyl, substituted or unsubstituted propyl, substituted or unsubstituted phenyl and substituted or unsubstituted benzyl;
and $R_{7a}$ is selected from hydrogen, substituted or unsubstituted methyl and substituted or unsubstituted —O-methyl.
and $R_8$, $R_{8'}$ and $R_{8''}$ are independently selected from hydrogen, unsubstituted methyl and unsubstituted ethyl;
and $R_c$ and $R_{c'}$ are both hydrogen;
and $R_9$ is unsubstituted methyl;
and $R_{10}$ and $R_{10'}$ are independently selected from hydrogen, and unsubstituted methyl and unsubstituted ethyl;
and $R_{11}$ is unsubstituted methyl;
and $R_{12}$, $R_{12'}$ and $R_{12''}$ are independently selected from hydrogen and unsubstituted methyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
m is 0, 1, 2 or 3.

In a preferred embodiment
n is 0, 1, 2 or 3.

In a preferred embodiment
p is 0 or 1.

In a preferred embodiment
W is nitrogen or —C(methyl)-.

In a preferred embodiment
X is selected from a bond, substituted or unsubstituted phenyl, —CH(methyl)-, —CH(CH$_2$—O-methyl)-, —CH(phenyl)-, —CH(benzyl)-, CH(tetrahydropyrane)-, —CH(pyridine)-, —CH(thiophen)- or —CH(thiazole)-.

In a preferred embodiment
$R_x$ is substituted or unsubstituted methyl, substituted or unsubstituted phenyl; substituted or unsubstituted tetrahydropyrane, substituted or unsubstituted pyridine, substituted or unsubstituted thiophen or substituted or unsubstituted thiazole.

In a preferred embodiment
$R_{x'}$ is hydrogen.

In a preferred embodiment
$R_x$ is substituted or unsubstituted methyl, substituted or unsubstituted phenyl; substituted or unsubstituted tetrahydropyrane, substituted or unsubstituted pyridine, substituted or unsubstituted thiophen or substituted or unsubstituted thiazole, while $R_{x'}$ is hydrogen.

In a preferred embodiment
$R_x$ is substituted or unsubstituted methyl, or a group selected from

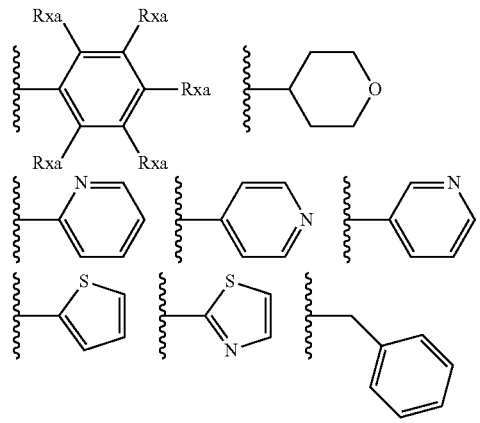

In a preferred embodiment
$R_x$ is substituted or unsubstituted methyl or a group selected from:

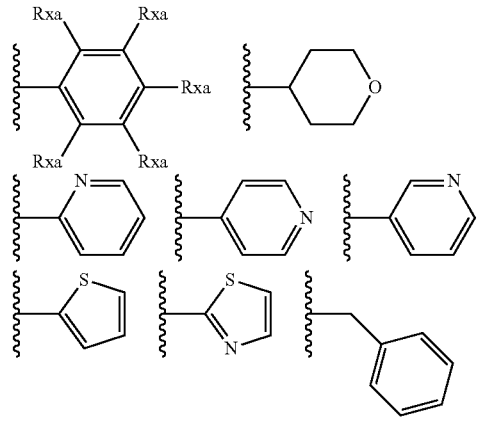

In a preferred embodiment
each $R_{xa}$ independently represents hydrogen, fluorine, —OH, —O-ethyl, —NHC(O)-methyl, —CN or —C(O)NH$_2$, In a preferred embodiment
$R_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, substituted or unsubstituted —NH-methyl, substituted or unsubstituted —N(methyl)$_2$, substituted or unsubstituted —NH-ethyl, substituted or unsubstituted —NH-benzyl, —NH$_2$, substituted or unsubstituted —NH—CH$_2$-cyclopropyl, substituted or unsubstituted —NH-propyl, substituted or unsubstituted NH—CH$_2$CH$_2$O-methyl, substituted or unsubstituted —NH-cyclopropyl, substituted or unsubstituted —NH-phenethyl, substituted or unsubstituted —N(methyl)-benzyl, substituted or unsubstituted —NHCH$_2$CH$_2$F and substituted or unsubstituted —NHCH$_2$CHF$_2$; more preferably R$_1$ is selected from substituted or unsubstituted pyrrolidine, substituted or unsubstituted piperidin, substituted or unsubstituted tetrahydroisoquinoline, substituted or unsubstituted tetrahydroquinoline, substituted or unsubstituted azetidine, substituted or unsubstituted morpholine, —NH-methyl, —N(methyl)$_2$, —NH-ethyl, —NH-benzyl, —NH$_2$, —NH—CH$_2$-cyclopropyl, —NH-propyl, —NH—CH$_2$CH$_2$O-methyl, —NH-cyclopropyl, —NH-phenethyl, —N(methyl)-benzyl, —NHCH$_2$CH$_2$F and —NHCH$_2$CHF$_2$.

In a preferred embodiment
R$_1$ is selected from

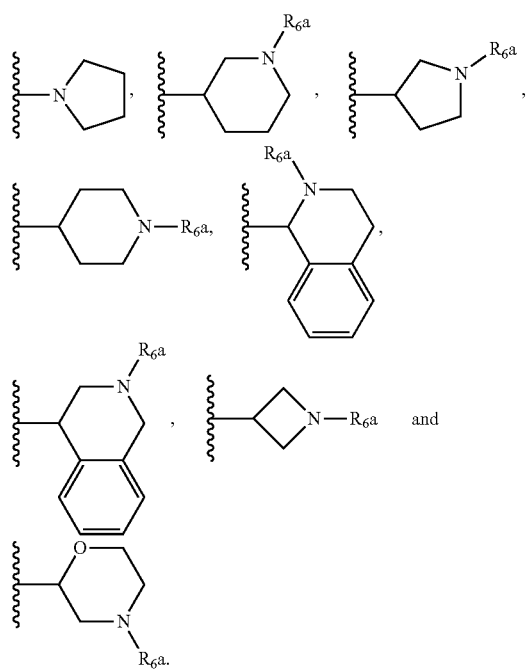

In a preferred embodiment
R$_1$ is selected from

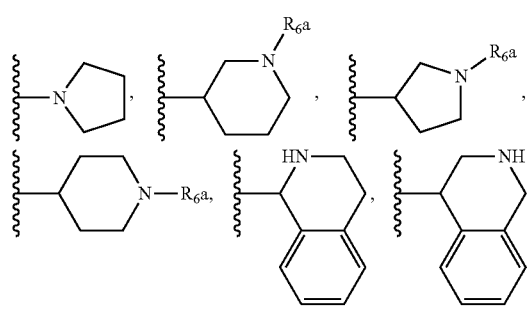

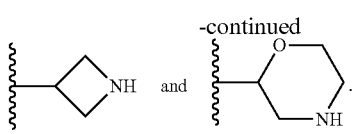

In a preferred embodiment
R$_2$ is selected from hydrogen, substituted or unsubstituted methyl, substituted or unsubstituted isopropyl, substituted or unsubstituted —NH-methyl, substituted or unsubstituted —N(methyl)$_2$, substituted or unsubstituted —N(ethyl)(methyl), substituted or unsubstituted —NH-phenyl, substituted or unsubstituted —NH-benzyl, substituted or unsubstituted —N(methyl)(benzyl), substituted or unsubstituted —N(methyl)(propyl), substituted or unsubstituted morpholine, substituted or unsubstituted oxadiazole, substituted or unsubstituted azetidine, substituted or unsubstituted pyrrolidine and —CN; preferably R$_2$ is selected from hydrogen, methyl, isopropyl, —NH-methyl, —N(methyl)$_2$, —N(ethyl)(methyl), —NH-phenyl, —NH-benzyl, —N(methyl)(benzyl), —N(methyl)(ethyl-OH), —N(methyl)(ethyl-O-methyl), —N(methyl)(propyl-OH), —N(methyl)(ethyl-N(methyl)$_2$), substituted or unsubstituted morpholine, substituted or unsubstituted oxadiazole, substituted or unsubstituted azetidine, substituted or unsubstituted pyrrolidine and —CN;

In a preferred embodiment
R$_2$ is selected from hydrogen, —NR$_7$R$_7'$, —CN, —CHR$_7$R$_7'$ and heterocyclyl wherein the heterocyclyl is selected from:

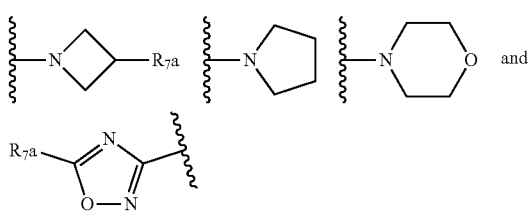

In a preferred embodiment
R$_3$ is selected from hydrogen and substituted or unsubstituted methyl.

In a preferred embodiment
R$_4$ is selected from hydrogen and substituted or unsubstituted methyl.

In a preferred embodiment
R$_3$ is selected from hydrogen and substituted or unsubstituted methyl while R$_4$ is selected from hydrogen and substituted or unsubstituted methyl.

In a preferred embodiment
R$_3$ and R$_4$ are both hydrogen.

In a preferred embodiment
R$_3$ and R$_4$ are both substituted or unsubstituted methyl.

In a preferred embodiment
R$_{4'}$ is substituted or unsubstituted methyl.

In a preferred embodiment
R$_5$ is hydrogen, bromine, substituted or unsubstituted pyrrolidone, —OH, substituted or unsubstituted —O-methyl, substituted or unsubstituted —O-ethyl, —NHC(O)-methyl, —CN, —C(O)NH$_2$ or —C(O)N(methyl)$_2$.

In a preferred embodiment
$R_{5'}$ is hydrogen.

In a preferred embodiment
$R_5$ is hydrogen, bromine, substituted or unsubstituted pyrrolidone, —OH, substituted or unsubstituted —O-methyl, substituted or unsubstituted —O-ethyl, —NHC(O)-methyl, —CN, —C(O)NH$_2$ or —C(O)N(methyl)$_2$, while $R_{5'}$ is hydrogen.

In a preferred embodiment
$R_6$ is hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl or substituted or unsubstituted —CH$_2$-cyclopropyl.

In a preferred embodiment
$R_{6'}$ is hydrogen or substituted or unsubstituted methyl.

In a preferred embodiment
$R_6$ is hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl or substituted or unsubstituted —CH$_2$-cyclopropyl, while $R_{6'}$ is hydrogen or substituted or unsubstituted methyl.

In a preferred embodiment
$R_6$ is hydrogen, substituted or unsubstituted methyl, substituted or unsubstituted ethyl, substituted or unsubstituted propyl, substituted or unsubstituted benzyl, substituted or unsubstituted phenethyl, substituted or unsubstituted cyclopropyl or substituted or unsubstituted —CH$_2$-cyclopropyl, while $R_6$ is substituted or unsubstituted methyl.

In a preferred embodiment
$R_{6a}$ is selected from hydrogen, substituted or unsubstituted methyl, substituted or unsubstituted benzyl and substituted or unsubstituted phenethyl.

In a preferred embodiment
$R_7$ is hydrogen, substituted or unsubstituted methyl, substituted or unsubstituted ethyl, substituted or unsubstituted propyl, substituted or unsubstituted phenyl and substituted or unsubstituted benzyl.

In a preferred embodiment
$R_{7'}$ is hydrogen or substituted or unsubstituted methyl.

In a preferred embodiment
$R_7$ is hydrogen, substituted or unsubstituted methyl, substituted or unsubstituted ethyl, substituted or unsubstituted propyl, substituted or unsubstituted phenyl and substituted or unsubstituted benzyl, while $R_{7'}$ is hydrogen or substituted or unsubstituted methyl.

In a preferred embodiment
$R_7$ and $R_{7'}$ are both substituted or unsubstituted methyl.

In a preferred embodiment
$R_{7a}$ is hydrogen, substituted or unsubstituted —O-methyl or substituted or unsubstituted methyl.

In a preferred embodiment
$R_8$ is hydrogen, unsubstituted methyl or unsubstituted ethyl.

In a preferred embodiment
$R_{8'}$ is hydrogen or unsubstituted methyl.

In a preferred embodiment
$R_8$ is hydrogen or unsubstituted methyl, while $R_{8'}$ is hydrogen or unsubstituted methyl.

In a preferred embodiment
$R_9$ is unsubstituted methyl.

In a preferred embodiment
$R_c$ is hydrogen.

In a preferred embodiment
$R_{c'}$ is hydrogen.

In a preferred embodiment
$R_c$ and $R_{c'}$ are both hydrogen.

In a preferred embodiment
$R_{10}$ is hydrogen or unsubstituted ethyl.

In a preferred embodiment
$R_{10'}$ is hydrogen or unsubstituted methyl.

In a preferred embodiment
$R_{10}$ is hydrogen while $R_{10'}$ is hydrogen or unsubstituted methyl.

In a preferred embodiment
$R_{11}$ is unsubstituted methyl;

In a preferred embodiment
$R_{12}$ is hydrogen or unsubstituted methyl;

In an particular embodiment
the halogen is fluorine, chlorine, iodine or bromine.

In an particular embodiment
the halogen is fluorine.

In an particular embodiment
the halogen is bromine.

In a preferred further embodiment, the compounds of the general Formula (I) are selected from

| EX | Structure | Chemical name |
|---|---|---|
| 1 | 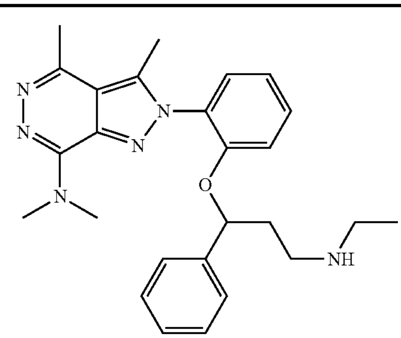 | 2-(2-(3-(Ethylamino)-1-phenylpropoxy)phenyl)-N,N,3,4-tetramethyl-2H-pyrazolo[3,4-d]pyridazin-7-amine |

| EX | Structure | Chemical name |
|---|---|---|
| 2 | 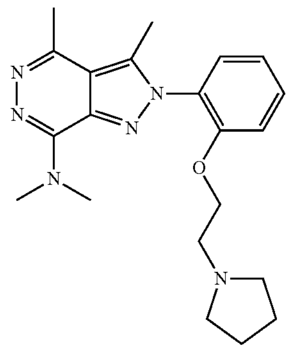 [SMILES: Cc1nnc(N(C)C)c2nn(-c3ccccc3OCCN3CCCC3)c(C)c12] | N,N,3,4-tetramethyl-2-(2-(2-(pyrrolidin-1-yl)ethoxy)phenyl)-2H-pyrazolo[3,4-d]pyridazin-7-amine |
| 3 | 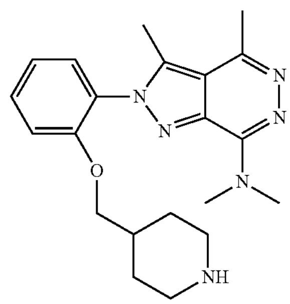 [SMILES: Cc1nnc(N(C)C)c2nn(-c3ccccc3OCC3CCNCC3)c(C)c12] | N,N,3,4-tetramethyl-2-(2-(piperidin-4-ylmethoxy)phenyl)-2H-pyrazolo[3,4-d]pyridazin-7-amine |
| 4 | 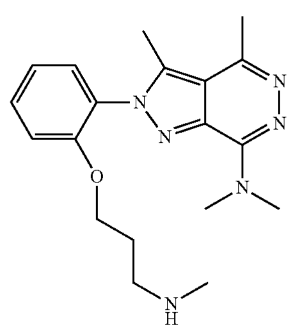 [SMILES: CNCCCOc1ccccc1-n1nc2c(N(C)C)nnc(C)c2c1C] | N,N,3,4-tetramethyl-2-(2-(3-(methylamino)propoxy)phenyl)-2H-pyrazolo[3,4-d]pyridazin-7-amine |
| 5 | 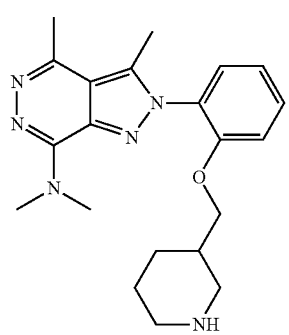 [SMILES: Cc1nnc(N(C)C)c2nn(-c3ccccc3OCC3CCCNC3)c(C)c12] | N,N,3,4-tetramethyl-2-(2-(piperidin-3-ylmethoxy)phenyl)-2H-pyrazolo[3,4-d]pyridazin-7-amine |

| EX | Structure | Chemical name |
|---|---|---|
| 6 | 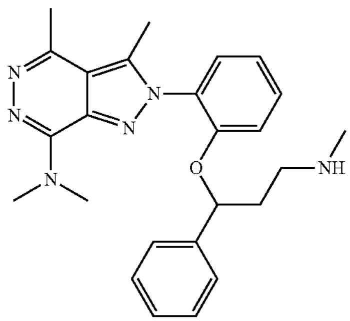 [SMILES: CNCCC(Oc1ccccc1-n1nc2c(N(C)C)nnc(C)c2c1C)c1ccccc1] | N,N,3,4-tetramethyl-2-(2-(3-(methylamino)-1-phenylpropoxy)phenyl)-2H-pyrazolo[3,4-d]pyridazin-7-amine |
| 7 | 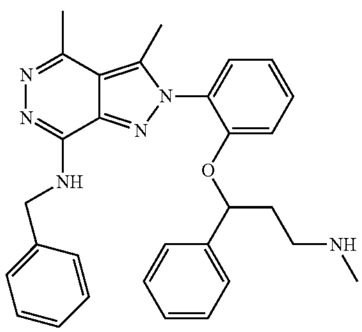 [SMILES: CNCCC(Oc1ccccc1-n1nc2c(NCc3ccccc3)nnc(C)c2c1C)c1ccccc1] | N-benzyl-3,4-dimethyl-2-(2-(3-(methylamino)-1-phenylpropoxy)phenyl)-2H-pyrazolo[3,4-d]pyridazin-7-amine |
| 8 | 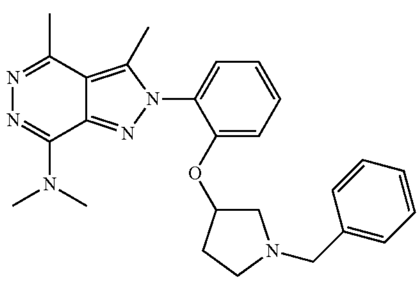 [SMILES: Cc1nnc(N(C)C)c2nn(-c3ccccc3OC3CCN(Cc4ccccc4)C3)c(C)c12] | 2-(2-((1-benzylpyrrolidin-3-yl)oxy)phenyl)-N,N,3,4-tetramethyl-2H-pyrazolo[3,4-d]pyridazin-7-amine |
| 9 | 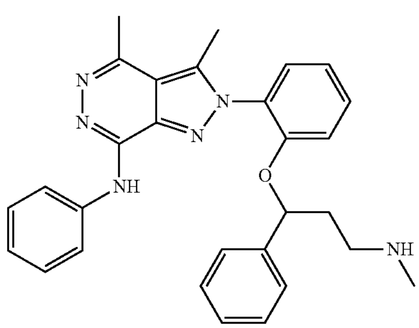 [SMILES: CNCCC(Oc1ccccc1-n1nc2c(Nc3ccccc3)nnc(C)c2c1C)c1ccccc1] | 3,4-dimethyl-2-(2-(3-(methylamino)-1-phenylpropoxy)phenyl)-N-phenyl-2H-pyrazolo[3,4-d]pyridazin-7-amine |
| 10 | 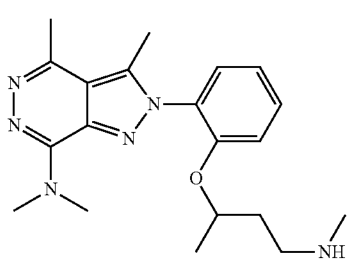 [SMILES: CNCCC(C)Oc1ccccc1-n1nc2c(N(C)C)nnc(C)c2c1C] | N,N,3,4-tetramethyl-2-(2-((4-(methylamino)butan-2-yl)oxy)phenyl)-2H-pyrazolo[3,4-d]pyridazin-7-amine |

| EX | Structure | Chemical name |
|---|---|---|
| 11 | 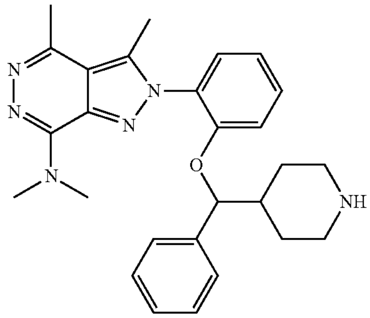 [SMILES: Cc1nnc(N(C)C)c2nn(-c3ccccc3OC(c3ccccc3)C3CCNCC3)c(C)c12] | N,N,3,4-tetramethyl-2-(2-(phenyl(piperidin-4-yl)methoxy)phenyl)-2H-pyrazolo[3,4-d]pyridazin-7-amine |
| 12 | 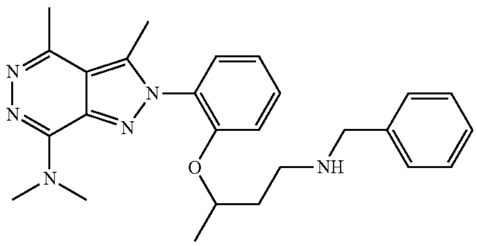 [SMILES: Cc1nnc(N(C)C)c2nn(-c3ccccc3OC(C)CCNCc3ccccc3)c(C)c12] | 2-(2-((4-(benzylamino)butan-2-yl)oxy)phenyl)-N,N,3,4-tetramethyl-2H-pyrazolo[3,4-d]pyridazin-7-amine |
| 13 | 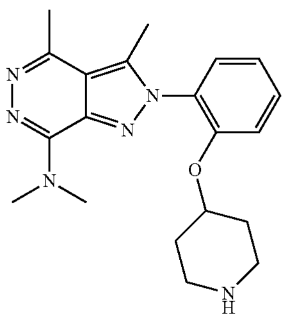 [SMILES: Cc1nnc(N(C)C)c2nn(-c3ccccc3OC3CCNCC3)c(C)c12] | N,N,3,4-tetramethyl-2-(2-(piperidin-4-yloxy)phenyl)-2H-pyrazolo[3,4-d]pyridazin-7-amine |
| 14 | 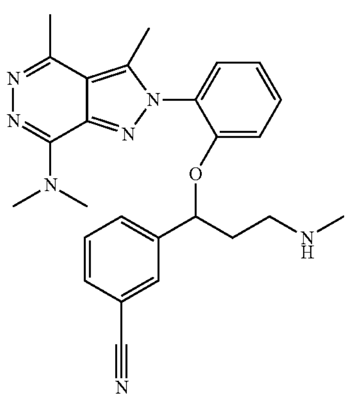 [SMILES: CNCCC(Oc1ccccc1-n1nc2c(N(C)C)nnc(C)c2c1C)c1cccc(C#N)c1] | 3-(1-(2-(7-(dimethylamino)-3,4-dimethyl-2H-pyrazolo[3,4-d]pyridazin-2-yl)phenoxy)-3-(methylamino)propyl)benzonitrile |
| 15 | 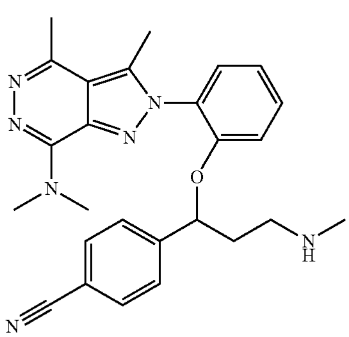 [SMILES: CNCCC(Oc1ccccc1-n1nc2c(N(C)C)nnc(C)c2c1C)c1ccc(C#N)cc1] | 4-(1-(2-(7-(dimethylamino)-3,4-dimethyl-2H-pyrazolo[3,4-d]pyridazin-2-yl)phenoxy)-3-(methylamino)propyl)benzonitrile |

| EX | Structure | Chemical name |
|---|---|---|
| 16 | 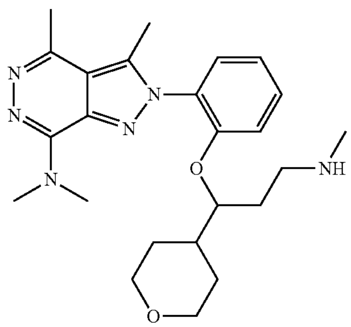 [SMILES: CNCCC(Oc1ccccc1-n1nc2c(N(C)C)nnc(C)c2c1C)C1CCOCC1] | N,N,3,4-tetramethyl-2-(2-(3-(methylamino)-1-(tetrahydro-2H-pyran-4-yl)propoxy)phenyl)-2H-pyrazolo[3,4-d]pyridazin-7-amine |
| 17 | 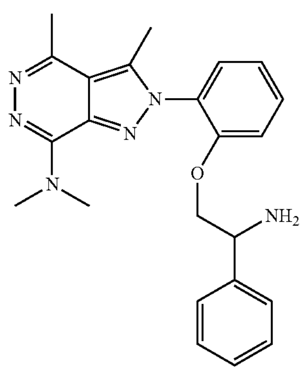 [SMILES: Cc1nnc(N(C)C)c2nn(-c3ccccc3OCC(N)c3ccccc3)c(C)c12] | 2-(2-(2-amino-2-phenylethoxy)phenyl)-N,N,3,4-tetramethyl-2H-pyrazolo[3,4-d]pyridazin-7-amine |
| 18 | 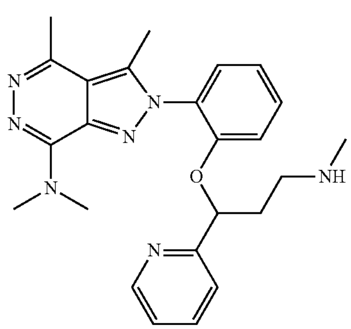 [SMILES: CNCCC(Oc1ccccc1-n1nc2c(N(C)C)nnc(C)c2c1C)c1ccccn1] | N,N,3,4-tetramethyl-2-(2-(3-(methylamino)-1-(pyridin-2-yl)propoxy)phenyl)-2H-pyrazolo[3,4-d]pyridazin-7-amine |
| 19 | 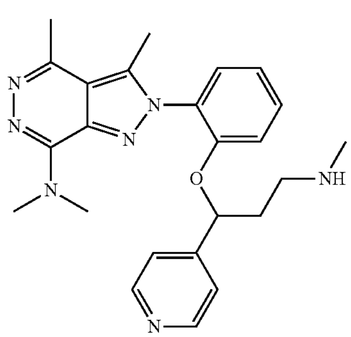 [SMILES: CNCCC(Oc1ccccc1-n1nc2c(N(C)C)nnc(C)c2c1C)c1ccncc1] | N,N,3,4-tetramethyl-2-(2-(3-(methylamino)-1-(pyridin-4-yl)propoxy)phenyl)-2H-pyrazolo[3,4-d]pyridazin-7-amine |

| EX | Structure | Chemical name |
|---|---|---|
| 20 | 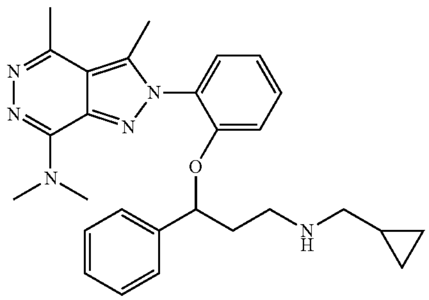 [SMILES: Cc1nnc(N(C)C)c2nn(-c3ccccc3OC(CCNCC3CC3)c3ccccc3)c(C)c12] | 2-(2-(3-((cyclopropylmethyl)amino)-1-phenylpropoxy)phenyl)-N,N,3,4-tetramethyl-2H-pyrazolo[3,4-d]pyridazin-7-amine |
| 21 | 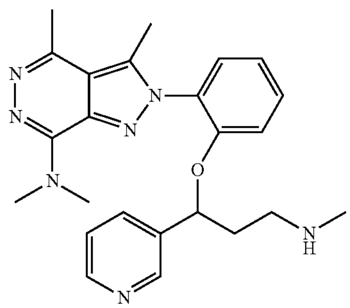 [SMILES: CNCCC(Oc1ccccc1-n1nc2c(N(C)C)nnc(C)c2c1C)c1cccnc1] | N,N,3,4-tetramethyl-2-(2-(3-(methylamino)-1-(pyridin-3-yl)propoxy)phenyl)-2H-pyrazolo[3,4-d]pyridazin-7-amine |
| 22 | 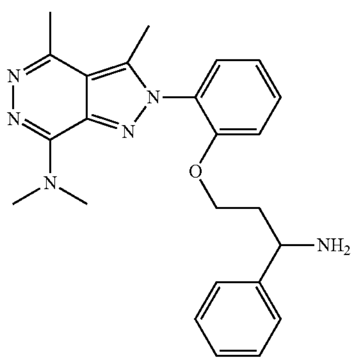 [SMILES: Cc1nnc(N(C)C)c2nn(-c3ccccc3OCCC(N)c3ccccc3)c(C)c12] | 2-(2-(3-amino-3-phenylpropoxy)phenyl)-N,N,3,4-tetramethyl-2H-pyrazolo[3,4-d]pyridazin-7-amine |
| 23 | 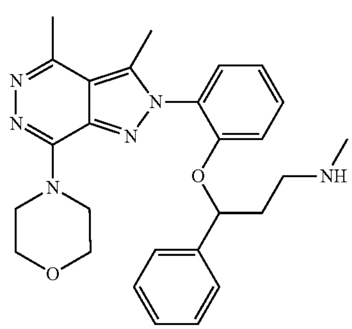 [SMILES: CNCCC(Oc1ccccc1-n1nc2c(N3CCOCC3)nnc(C)c2c1C)c1ccccc1] | 3-(2-(3,4-dimethyl-7-morpholino-2H-pyrazolo[3,4-d]pyridazin-2-yl)phenoxy)-N-methyl-3-phenylpropan-1-amine |
| 24 | 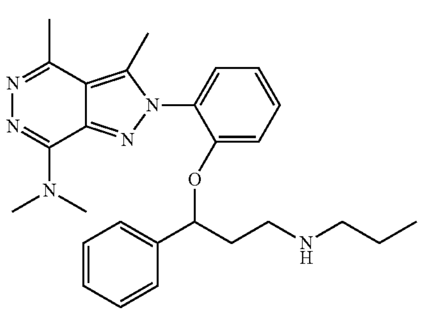 [SMILES: CCCNCCC(Oc1ccccc1-n1nc2c(N(C)C)nnc(C)c2c1C)c1ccccc1] | N,N,3,4-tetramethyl-2-(2-(1-phenyl-3-(propylamino)propoxy)phenyl)-2H-pyrazolo[3,4-d]pyridazin-7-amine |

-continued

| EX | Structure | Chemical name |
|---|---|---|
| 25 | 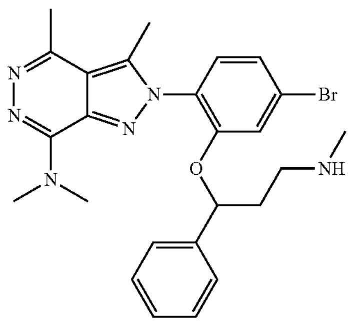 [SMILES: CNCCC(Oc1cc(Br)ccc1-n1nc2c(N(C)C)nnc(C)c2c1C)c1ccccc1] | 2-(4-bromo-2-(3-(methylamino)-1-phenylpropoxy)phenyl)-N,N,3,4-tetramethyl-2H-pyrazolo[3,4-d]pyridazin-7-amine |
| 26 | 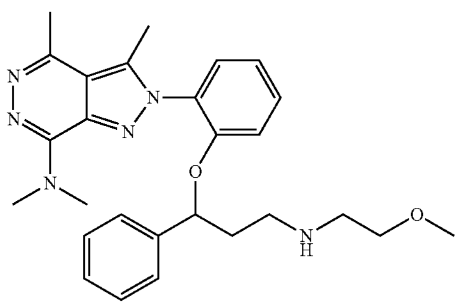 [SMILES: COCCNCCC(Oc1ccccc1-n1nc2c(N(C)C)nnc(C)c2c1C)c1ccccc1] | 2-(2-(3-((2-methoxyethyl)amino)-1-phenylpropoxy)phenyl)-N,N,3,4-tetramethyl-2H-pyrazolo[3,4-d]pyridazin-7-amine |
| 27 | 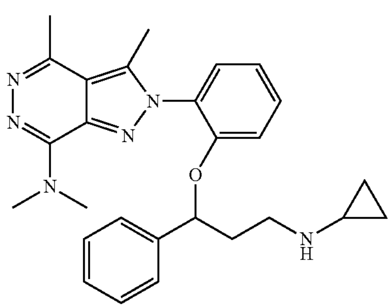 [SMILES: Cc1nnc(N(C)C)c2nn(-c3ccccc3OC(CCNC3CC3)c3ccccc3)c(C)c12] | 2-(2-(3-(cyclopropylamino)-1-phenylpropoxy)phenyl)-N,N,3,4-tetramethyl-2H-pyrazolo[3,4-d]pyridazin-7-amine |
| 28 | 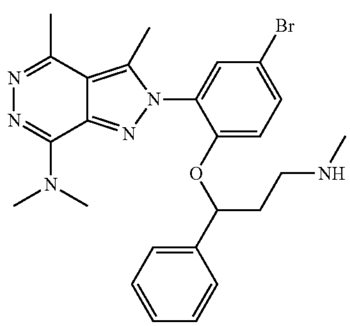 [SMILES: CNCCC(Oc1ccc(Br)cc1-n1nc2c(N(C)C)nnc(C)c2c1C)c1ccccc1] | 2-(5-bromo-2-(3-(methylamino)-1-phenylpropoxy)phenyl)-N,N,3,4-tetramethyl-2H-pyrazolo[3,4-d]pyridazin-7-amine |
| 29 | 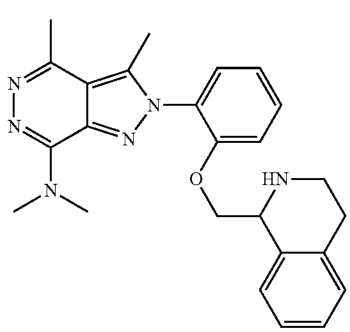 [SMILES: Cc1nnc(N(C)C)c2nn(-c3ccccc3OCC3NCCc4ccccc43)c(C)c12] | N,N,3,4-tetramethyl-2-(2-((1,2,3,4-tetrahydroisoquinolin-1-yl)methoxy)phenyl)-2H-pyrazolo[3,4-d]pyridazin-7-amine |

| EX | Structure | Chemical name |
|---|---|---|
| 30 | 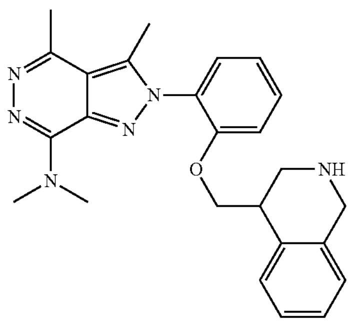 [SMILES: Cc1nnc(N(C)C)c2nn(-c3ccccc3OCC3CNCc4ccccc43)c(C)c12] | N,N,3,4-tetramethyl-2-(2-((1,2,3,4-tetrahydroisoquinolin-4-yl)methoxy)phenyl)-2H-pyrazolo[3,4-d]pyridazin-7-amine |
| 31 | 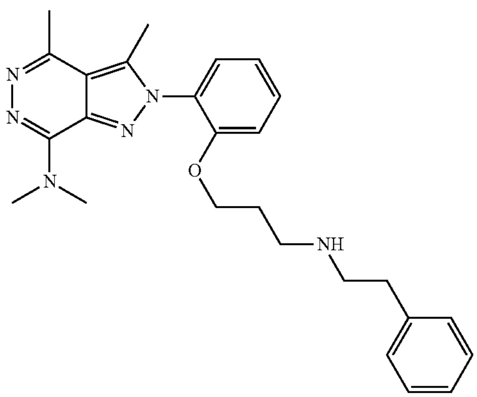 [SMILES: Cc1nnc(N(C)C)c2nn(-c3ccccc3OCCCNCCc3ccccc3)c(C)c12] | N,N,3,4-tetramethyl-2-(2-(3-(phenethylamino)propoxy)phenyl)-2H-pyrazolo[3,4-d]pyridazin-7-amine |
| 32 | 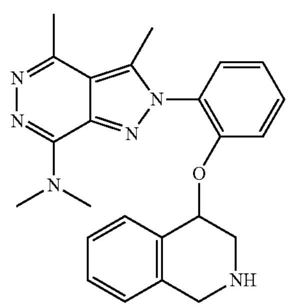 [SMILES: Cc1nnc(N(C)C)c2nn(-c3ccccc3OC3CNCc4ccccc43)c(C)c12] | N,N,3,4-tetramethyl-2-(2-((1,2,3,4-tetrahydroisoquinolin-4-yl)oxy)phenyl)-2H-pyrazolo[3,4-d]pyridazin-7-amine |
| 33 | 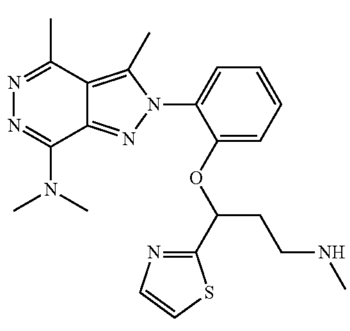 [SMILES: CNCCC(Oc1ccccc1-n1nc2c(N(C)C)nnc(C)c2c1C)c1nccs1] | N,N,3,4-tetramethyl-2-(2-(3-(methylamino)-1-(thiazol-2-yl)propoxy)phenyl)-2H-pyrazolo[3,4-d]pyridazin-7-amine |

-continued

| EX | Structure | Chemical name |
|---|---|---|
| 34 | 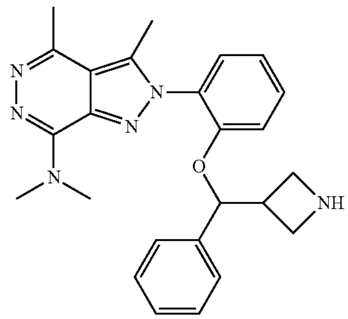 [SMILES: Cc1nnc(N(C)C)c2nn(-c3ccccc3OC(c3ccccc3)C3CNC3)c(C)c12] | 2-(2-(azetidin-3-yl(phenyl)methoxy)phenyl)-N,N,3,4-tetramethyl-2H-pyrazolo[3,4-d]pyridazin-7-amine |
| 35 | 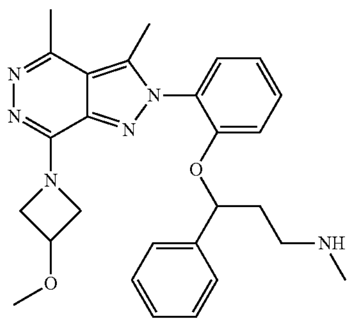 [SMILES: CNCCC(Oc1ccccc1-n1nc2c(N3CC(OC)C3)nnc(C)c2c1C)c1ccccc1] | 3-(2-(7-(3-methoxyazetidin-1-yl)-3,4-dimethyl-2H-pyrazolo[3,4-d]pyridazin-2-yl)phenoxy)-N-methyl-3-phenylpropan-1-amine |
| 36 | 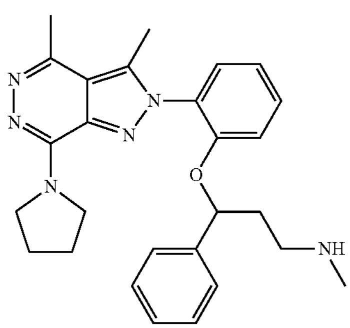 [SMILES: CNCCC(Oc1ccccc1-n1nc2c(N3CCCC3)nnc(C)c2c1C)c1ccccc1] | 3-(2-(3,4-dimethyl-7-(pyrrolidin-1-yl)-2H-pyrazolo[3,4-d]pyridazin-2-yl)phenoxy)-N-methyl-3-phenylpropan-1-amine |
| 37 | 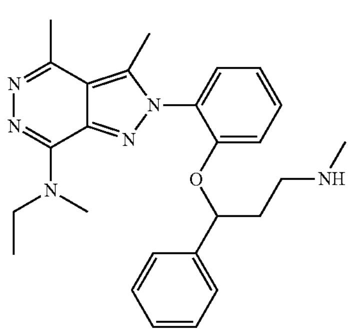 [SMILES: CCN(C)c1nnc(C)c2c(C)n(-c3ccccc3OC(CCNC)c3ccccc3)nc12] | N-ethyl-N,3,4-trimethyl-2-(2-(3-(methylamino)-1-phenylpropoxy)phenyl)-2H-pyrazolo[3,4-d]pyridazin-7-amine [2] |

-continued

| EX | Structure | Chemical name |
|---|---|---|
| 38 | 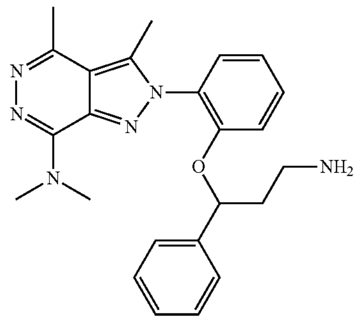 [SMILES: Cc1nnc(N(C)C)c2nn(-c3ccccc3OC(CCN)c3ccccc3)c(C)c12] | 2-(2-(3-amino-1-phenylpropoxy)phenyl)-N,N,3,4-tetramethyl-2H-pyrazolo[3,4-d]pyridazin-7-amine |
| 39 | 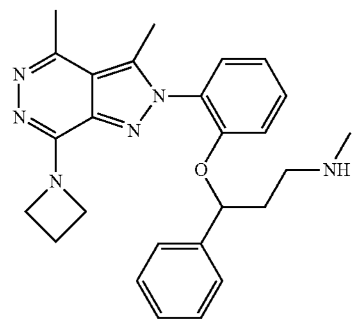 [SMILES: CNCCC(Oc1ccccc1-n1nc2c(N3CCC3)nnc(C)c2c1C)c1ccccc1] | 3-(2-(7-(azetidin-1-yl)-3,4-dimethyl-2H-pyrazolo[3,4-d]pyridazin-2-yl)phenoxy)-N-methyl-3-phenylpropan-1-amine |
| 40 | 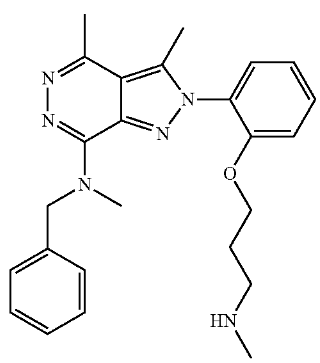 [SMILES: CNCCCOc1ccccc1-n1nc2c(N(C)Cc3ccccc3)nnc(C)c2c1C] | N-benzyl-N,3,4-trimethyl-2-(2-(3-(methylamino)propoxy)phenyl)-2H-pyrazolo[3,4-d]pyridazin-7-amine |
| 41 | 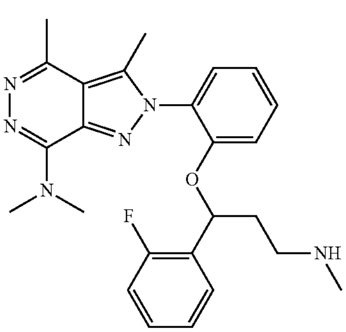 [SMILES: CNCCC(Oc1ccccc1-n1nc2c(N(C)C)nnc(C)c2c1C)c1ccccc1F] | 2-(2-(1-(2-fluorophenyl)-3-(methylamino)propoxy)phenyl)-N,N,3,4-tetramethyl-2H-pyrazolo[3,4-d]pyridazin-7-amine |

-continued

| EX | Structure | Chemical name |
|---|---|---|
| 42 | 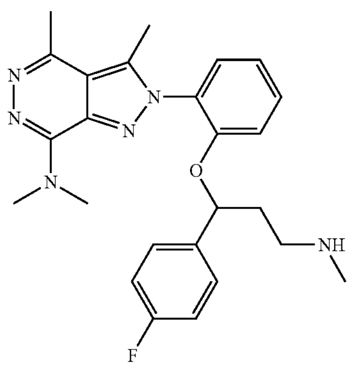 [SMILES: CNCCC(Oc1ccccc1-n1nc2c(N(C)C)nnc(C)c2c1C)c1ccc(F)cc1] | 2-(2-(1-(4-fluorophenyl)-3-(methylamino)propoxy)phenyl)-N,N,3,4-tetramethyl-2H-pyrazolo[3,4-d]pyridazin-7-amine |
| 43 | 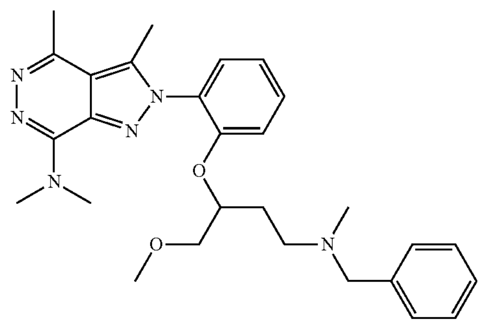 [SMILES: COCC(CCN(C)Cc1ccccc1)Oc1ccccc1-n1nc2c(N(C)C)nnc(C)c2c1C] | 2-(2-((4-(benzyl(methyl)amino)-1-methoxybutan-2-yl)oxy)phenyl)-N,N,3,4-tetramethyl-2H-pyrazolo[3,4-d]pyridazin-7-amine |
| 44 | 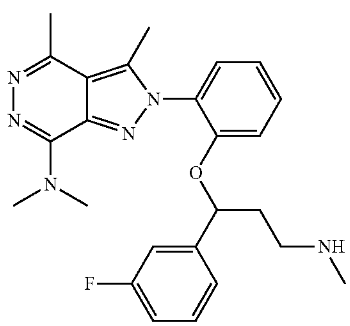 [SMILES: CNCCC(Oc1ccccc1-n1nc2c(N(C)C)nnc(C)c2c1C)c1cccc(F)c1] | 2-(2-(1-(3-fluorophenyl)-3-(methylamino)propoxy)phenyl)-N,N,3,4-tetramethyl-2H-pyrazolo[3,4-d]pyridazin-7-amine |
| 45 | 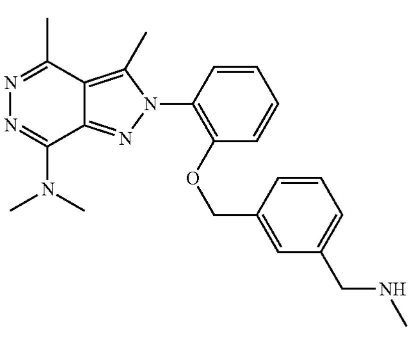 [SMILES: CNCc1cccc(COc2ccccc2-n2nc3c(N(C)C)nnc(C)c3c2C)c1] | N,N,3,4-tetramethyl-2-(2-((3-((methylamino)methyl)benzyl)oxy)phenyl)-2H-pyrazolo[3,4-d]pyridazin-7-amine |

| EX | Structure | Chemical name |
|---|---|---|
| 46 | 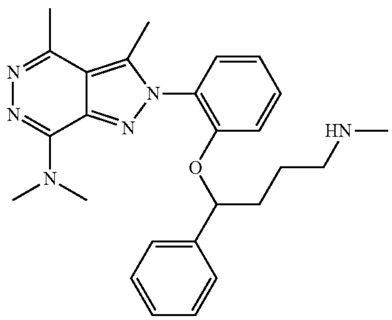 [SMILES: CNCCCC(Oc1ccccc1-n1nc2c(N(C)C)nnc(C)c2c1C)c1ccccc1] | N,N,3,4-tetramethyl-2-(2-(4-(methylamino)-1-phenylbutoxy)phenyl)-2H-pyrazolo[3,4-d]pyridazin-7-amine |
| 47 | 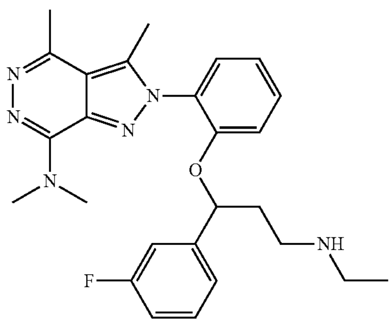 [SMILES: CCNCCC(Oc1ccccc1-n1nc2c(N(C)C)nnc(C)c2c1C)c1cccc(F)c1] | 2-(2-(3-(ethylamino)-1-(3-fluorophenyl)propoxy)phenyl)-N,N,3,4-tetramethyl-2H-pyrazolo[3,4-d]pyridazin-7-amine |
| 48 | 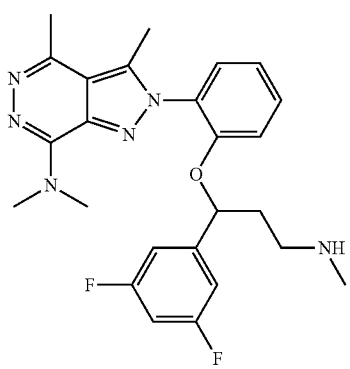 [SMILES: CNCCC(Oc1ccccc1-n1nc2c(N(C)C)nnc(C)c2c1C)c1cc(F)cc(F)c1] | 2-(2-(1-(3,5-difluorophenyl)-3-(methylamino)propoxy)phenyl)-N,N,3,4-tetramethyl-2H-pyrazolo[3,4-d]pyridazin-7-amine |
| 49 | 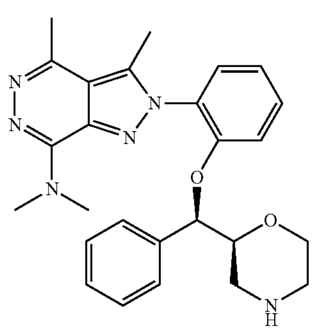 [SMILES: Cc1nnc(N(C)C)c2nn(-c3ccccc3O[C@H](c3ccccc3)[C@@H]3CNCCO3)c(C)c12] | N,N,3,4-tetramethyl-2-(2-((R)-((S)-morpholin-2-yl)(phenyl)methoxy)phenyl)-2H-pyrazolo[3,4-d]pyridazin-7-amine [3] |

| EX | Structure | Chemical name |
|---|---|---|
| 50 | 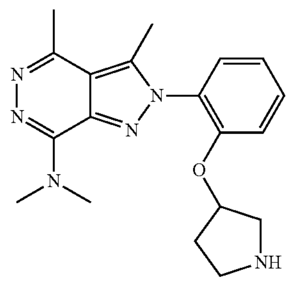 [SMILES: Cc1nnc(N(C)C)c2nn(-c3ccccc3OC3CCNC3)c(C)c12] | N,N,3,4-Tetramethyl-2-(2-(pyrrolidin-3-yloxy)phenyl)-2H-pyrazolo[3,4-d]pyridazin-7-amine |
| 51 | 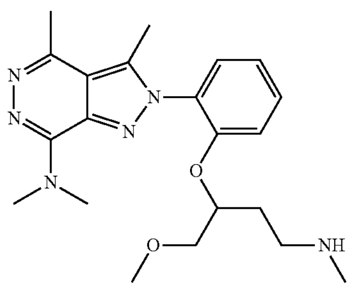 [SMILES: CNCCC(COC)Oc1ccccc1-n1nc2c(N(C)C)nnc(C)c2c1C] | 2-(2-((1-methoxy-4-(methylamino)butan-2-yl)oxy)phenyl)-N,N,3,4-tetramethyl-2H-pyrazolo[3,4-d]pyridazin-7-amine |
| 52 | 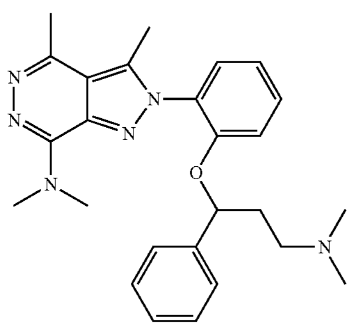 [SMILES: Cc1nnc(N(C)C)c2nn(-c3ccccc3OC(CCN(C)C)c3ccccc3)c(C)c12] | 2-(2-(3-(Dimethylamino)-1-phenylpropoxy)phenyl)-N,N,3,4-tetramethyl-2H-pyrazolo[3,4-d]pyridazin-7-amine |
| 53 | 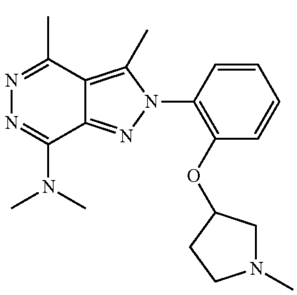 [SMILES: Cc1nnc(N(C)C)c2nn(-c3ccccc3OC3CCN(C)C3)c(C)c12] | N,N,3,4-tetramethyl-2-(2-((1-methylpyrrolidin-3-yl)oxy)phenyl)-2H-pyrazolo[3,4-d]pyridazin-7-amine |
| 54 | 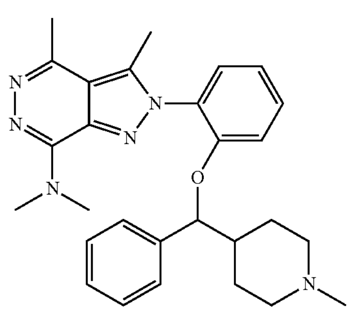 [SMILES: Cc1nnc(N(C)C)c2nn(-c3ccccc3OC(c3ccccc3)C3CCN(C)CC3)c(C)c12] | N,N,3,4-tetramethyl-2-(2-((1-methylpiperidin-4-yl)(phenyl)methoxy)phenyl)-2H-pyrazolo[3,4-d]pyridazin-7-amine |

-continued

| EX | Structure | Chemical name |
|---|---|---|
| 55 | 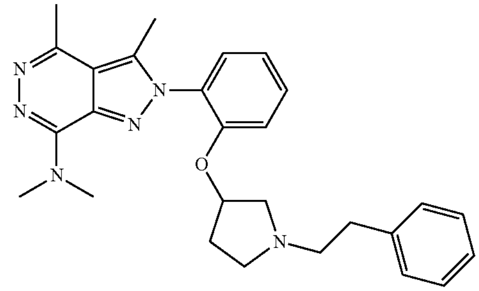 [SMILES: Cc1nnc(N(C)C)c2nn(-c3ccccc3OC3CCN(CCc4ccccc4)C3)c(C)c12] | N,N,3,4-tetramethyl-2-(2-((1-phenethylpyrrolidin-3-yl)oxy)phenyl)-2H-pyrazolo[3,4-d]pyridazin-7-amine |
| 56 | 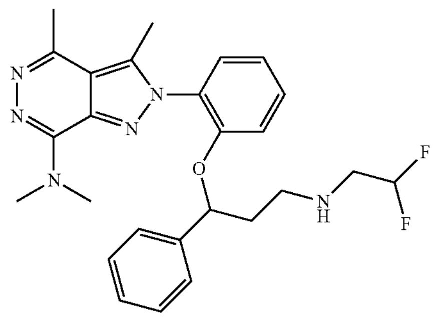 [SMILES: Cc1nnc(N(C)C)c2nn(-c3ccccc3OC(CCNCC(F)F)c3ccccc3)c(C)c12] | 2-(2-(3-((2,2-difluoroethyl)amino)-1-phenylpropoxy)phenyl)-N,N,3,4-tetramethyl-2H-pyrazolo[3,4-d]pyridazin-7-amine |
| 57 | 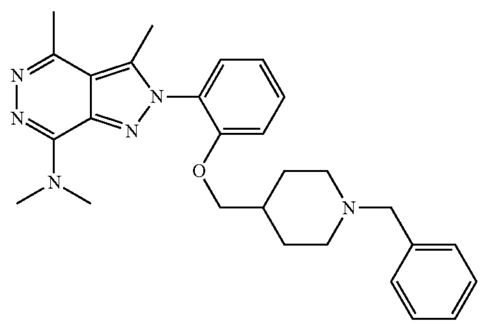 [SMILES: Cc1nnc(N(C)C)c2nn(-c3ccccc3OCC3CCN(Cc4ccccc4)CC3)c(C)c12] | 2-(2-((1-benzylpiperidin-4-yl)methoxy)phenyl)-N,N,3,4-tetramethyl-2H-pyrazolo[3,4-c]pyridazin-7-amine |
| 58 | 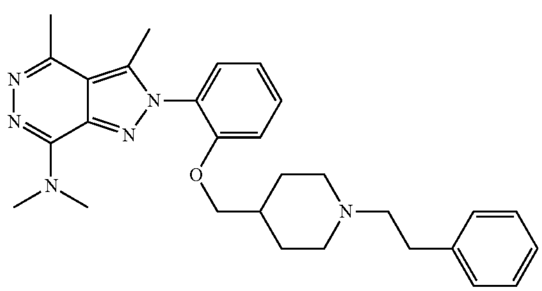 [SMILES: Cc1nnc(N(C)C)c2nn(-c3ccccc3OCC3CCN(CCc4ccccc4)CC3)c(C)c12] | N,N,3,4-tetramethyl-2-(2-((1-phenethylpiperidin-4-yl)methoxy)phenyl)-2H-pyrazolo[3,4-d]pyridazin-7-amine |
| 59 | 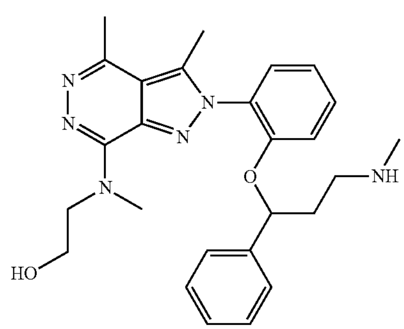 [SMILES: CNCCC(Oc1ccccc1-n1nc2c(N(C)CCO)nnc(C)c2c1C)c1ccccc1] | 2-((3,4-Dimethyl-2-(2-(3-(methylamino)-1-phenylpropoxy)phenyl)-2H-pyrazolo[3,4-d]pyridazin-7-yl)(methyl)amino)ethanol |

-continued

| EX | Structure | Chemical name |
|----|-----------|---------------|
| 60 | 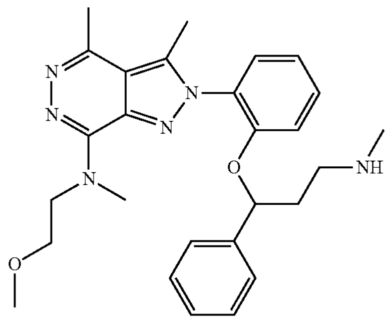 [SMILES: CNCCC(Oc1ccccc1-n1nc2c(N(C)CCOC)nnc(C)c2c1C)c1ccccc1] | N-(2-methoxyethyl)-N,3,4-trimethyl-2-(2-(3-(methylamino)-1-phenylpropoxy)phenyl)-2H-pyrazolo[3,4-d]pyridazin-7-amine |
| 61 | 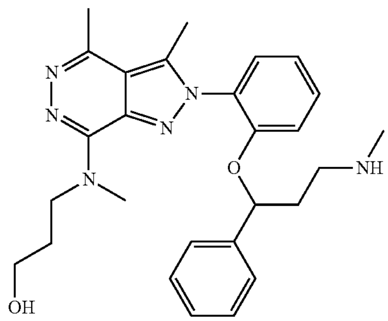 [SMILES: CNCCC(Oc1ccccc1-n1nc2c(N(C)CCCO)nnc(C)c2c1C)c1ccccc1] | 3-((3,4-dimethyl-2-(2-(3-(methylamino)-1-phenylpropoxy)phenyl)-2H-pyrazolo[3,4-d]pyridazin-7-yl)(methyl)amino)propan-1-ol |
| 62 | 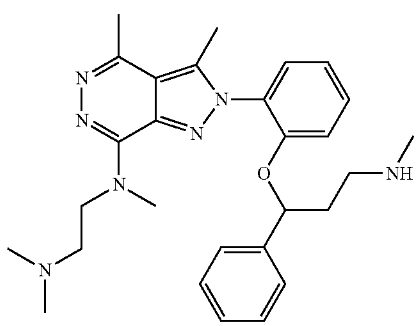 | N1-(3,4-dimethyl-2-(2-(3-(methylamino)-1-phenylpropoxy)phenyl)-2H-pyrazolo[3,4-d]pyridazin-7-yl)-N1,N2,N2-trimethylethane-1,2-diamine |
| 63 | 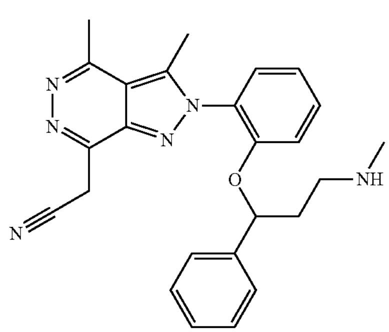 [SMILES: CNCCC(Oc1ccccc1-n1nc2c(CC#N)nnc(C)c2c1C)c1ccccc1] | 2-(3,4-Dimethyl-2-(2-(3-(methylamino)-1-phenylpropoxy)phenyl)-2H-pyrazolo[3,4-d]pyridazin-7-yl)acetonitrile |

-continued

| EX | Structure | Chemical name |
|---|---|---|
| 64 | 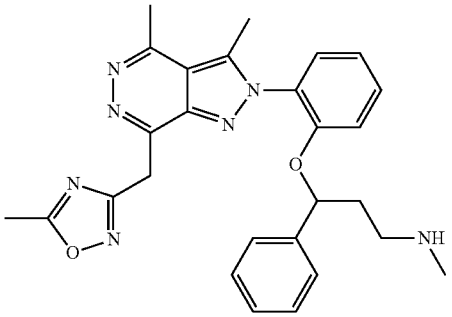 | 3-(2-(3,4-Dimethyl-7-((5-methyl-1,2,4-oxadiazol-3-yl)methyl)-2H-pyrazolo[3,4-d]pyridazin-2-yl)phenoxy)-N-methyl-3-phenylpropan-1-amine |
| 65 | 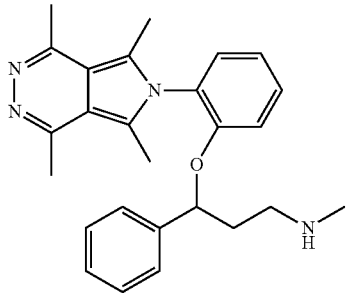 [SMILES: CNCCC(Oc1ccccc1-n1c(C)c2c(C)nnc(C)c2c1C)c1ccccc1] | N-Methyl-3-phenyl-3-(2-(1,4,5,7-tetramethyl-6H-pyrrolo[3,4-d]pyridazin-6-yl)phenoxy)propan-1-amine |
| 66 | 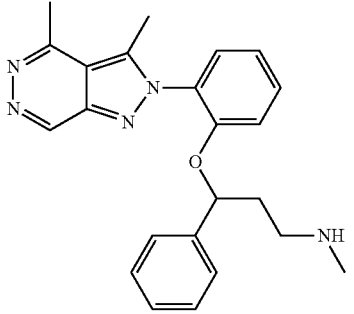 [SMILES: CNCCC(Oc1ccccc1-n1nc2cnnc(C)c2c1C)c1ccccc1] | 3-(2-(3,4-Dimethyl-2H-pyrazolo[3,4-d]pyridazin-2-yl)phenoxy)-N-methyl-3-phenylpropan-1-amine |
| 67 | 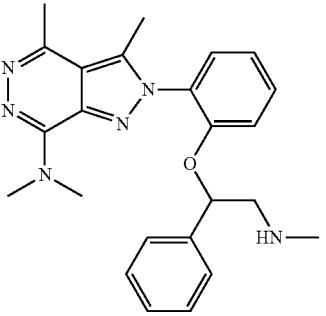 [SMILES: CNCC(Oc1ccccc1-n1nc2c(N(C)C)nnc(C)c2c1C)c1ccccc1] | N,N,3,4-Tetramethyl-2-(2-(2-(methylamino)-1-phenylethoxy)phenyl)-2H-pyrazolo[3,4-d]pyridazin-7-amine |
| 68 | 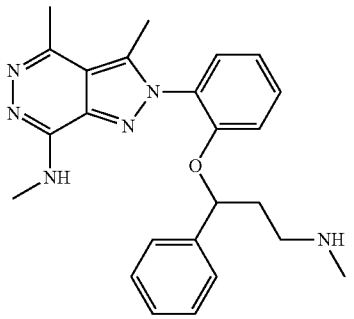 [SMILES: CNCCC(Oc1ccccc1-n1nc2c(NC)nnc(C)c2c1C)c1ccccc1] | N,3,4-Trimethyl-2-(2-(3-(methylamino)-1-phenylpropoxy)phenyl)-2H-pyrazolo[3,4-d]pyridazin-7-amine |

-continued

| EX | Structure | Chemical name |
|---|---|---|
| 69 | 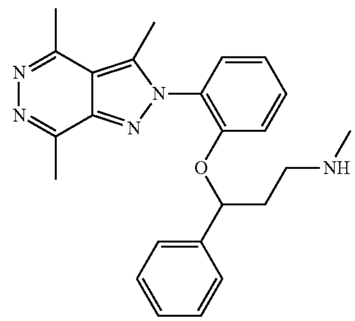 [SMILES: CNCCC(Oc1ccccc1-n1nc2c(C)nnc(C)c2c1C)c1ccccc1] | N-methyl-3-phenyl-3-(2-(3,4,7-trimethyl-2H-pyrazolo[3,4-d]pyridazin-2-yl)phenoxy)propan-1-amine |
| 70 | 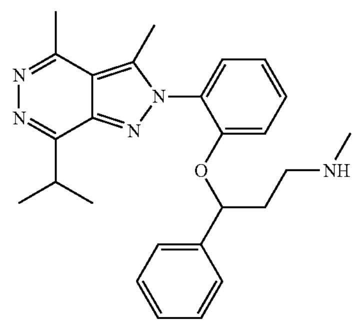 | 3-(2-(7-isopropyl-3,4-dimethyl-2H-pyrazolo[3,4-d]pyridazin-2-yl)phenoxy)-N-methyl-3-phenylpropan-1-amine |
| 71 | 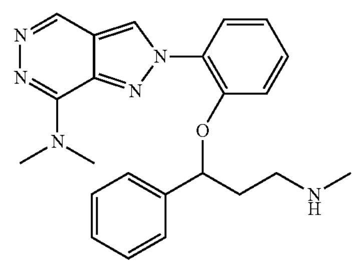 [SMILES: CNCCC(Oc1ccccc1-n1cc2cnnc(N(C)C)c2n1)c1ccccc1] | N,N-dimethyl-2-(2-(3-(methylamino)-1-phenylpropoxy)phenyl)-2H-pyrazolo[3,4-d]pyridazin-7-amine |
| 72 | 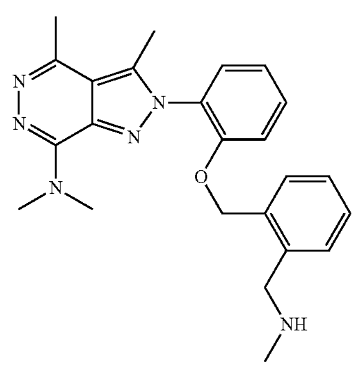 [SMILES: CNCc1ccccc1COc1ccccc1-n1nc2c(N(C)C)nnc(C)c2c1C] | N,N,3,4-Tetramethyl-2-(2-((2-((methylamino)methyl)benzyl)oxy)phenyl)-2H-pyrazolo[3,4-d]pyridazin-7-amine |
| 73 | 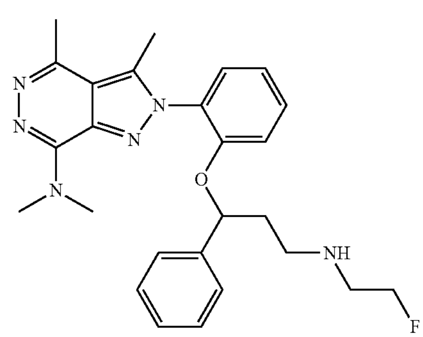 [SMILES: Cc1nnc(N(C)C)c2nn(-c3ccccc3OC(CCNCCF)c3ccccc3)c(C)c12] | 2-(2-(3-((2-Fluoroethyl)amino)-1-phenylpropoxy)phenyl)-N,N,3,4-tetramethyl-2H-pyrazolo[3,4-d]pyridazin-7-amine |

| EX | Structure | Chemical name |
|---|---|---|
| 74 | 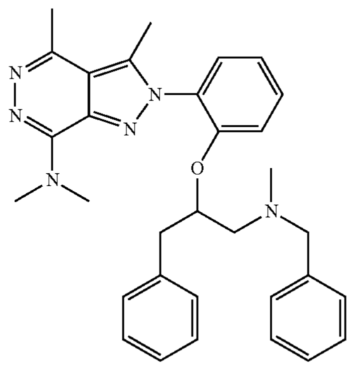 [SMILES: Cc1nnc(N(C)C)c2nn(-c3ccccc3OC(Cc3ccccc3)CN(C)Cc3ccccc3)c(C)c12] | 2-(2-((1-(Benzyl(methyl)amino)-3-phenylpropan-2-yl)oxy)phenyl)-N,N,3,4-tetramethyl-2H-pyrazolo[3,4-d]pyridazin-7-amine |
| 75 | 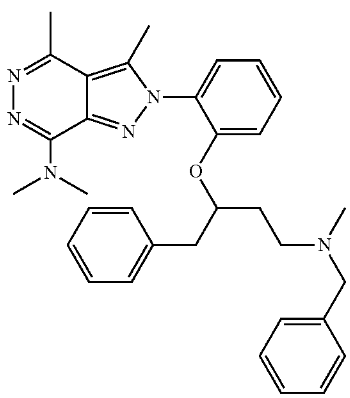 [SMILES: Cc1nnc(N(C)C)c2nn(-c3ccccc3OC(CCN(C)Cc3ccccc3)Cc3ccccc3)c(C)c12] | 2-(2-((4-(benzyl(methyl)amino)-1-phenylbutan-2-yl)oxy)phenyl)-N,N,3,4-tetramethyl-2H-pyrazolo[3,4-d]pyridazin-7-amine |
| 76 | 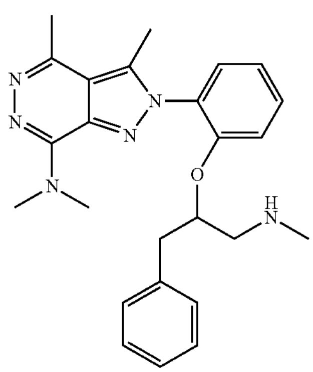 [SMILES: CNCC(Cc1ccccc1)Oc1ccccc1-n1nc2c(N(C)C)nnc(C)c2c1C] | N,N,3,4-Tetramethyl-2-(2-((1-(methylamino)-3-phenylpropan-2-yl)oxy)phenyl)-2H-pyrazolo[3,4-d]pyridazin-7-amine |
| 77 | 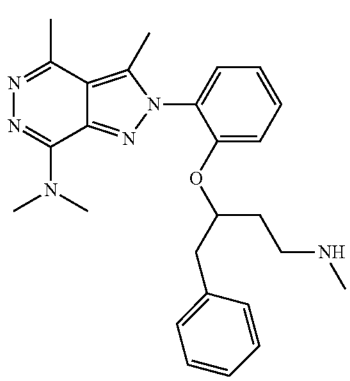 [SMILES: CNCCC(Cc1ccccc1)Oc1ccccc1-n1nc2c(N(C)C)nnc(C)c2c1C] | N,N,3,4-tetramethyl-2-(2-((4-(methylamino)-1-phenylbutan-2-yl)oxy)phenyl)-2H-pyrazolo[3,4-d]pyridazin-7-amine |

-continued

| EX | Structure | Chemical name |
|---|---|---|
| 78 | 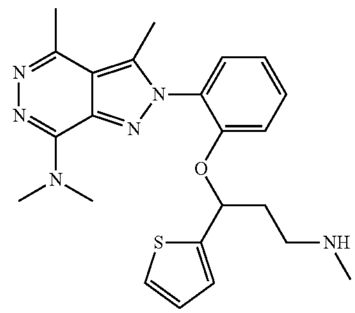 [SMILES: CNCCC(Oc1ccccc1-n1nc2c(N(C)C)nnc(C)c2c1C)c1cccs1] | N,N,3,4-Tetramethyl-2-(2-(3-(methylamino)-1-(thiophen-2-yl)propoxy)phenyl)-2H-pyrazolo[3,4-d]pyridazin-7-amine |
| 79 | 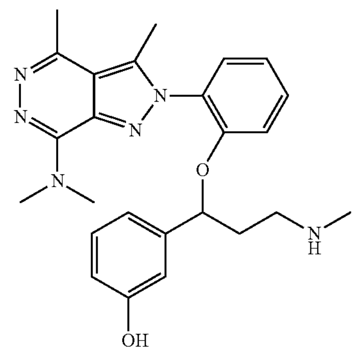 [SMILES: CNCCC(Oc1ccccc1-n1nc2c(N(C)C)nnc(C)c2c1C)c1cccc(O)c1] | 3-(1-(2-(7-(Dimethylamino)-3,4-dimethyl-2H-pyrazolo[3,4-d]pyridazin-2-yl)phenoxy)-3-(methylamino)propyl)phenol |
| 80 | 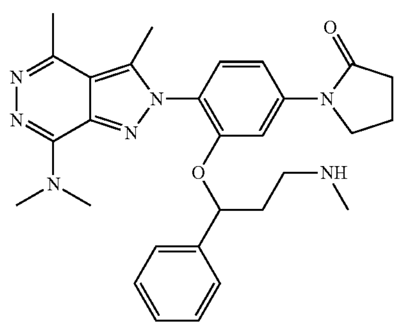 [SMILES: CNCCC(Oc1cc(N2CCCC2=O)ccc1-n1nc2c(N(C)C)nnc(C)c2c1C)c1ccccc1] | 1-(4-(7-(Dimethylamino)-3,4-dimethyl-2H-pyrazolo[3,4-d]pyridazin-2-yl)-3-(3-(methylamino)-1-phenylpropoxy)phenyl)pyrrolidin-2-one |
| 81 | 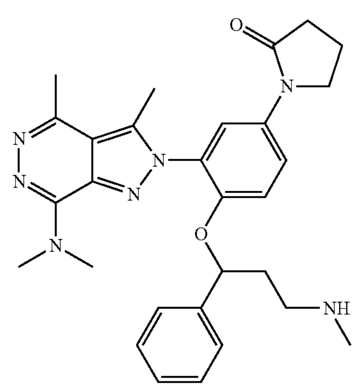 [SMILES: CNCCC(Oc1ccc(N2CCCC2=O)cc1-n1nc2c(N(C)C)nnc(C)c2c1C)c1ccccc1] | 1-(3-(7-(dimethylamino)-3,4-dimethyl-2H-pyrazolo[3,4-d]pyridazin-2-yl)-4-(3-(methylamino)-1-phenylpropoxy)phenyl)pyrrolidin-2-one |

| EX | Structure | Chemical name |
|---|---|---|
| 82 | 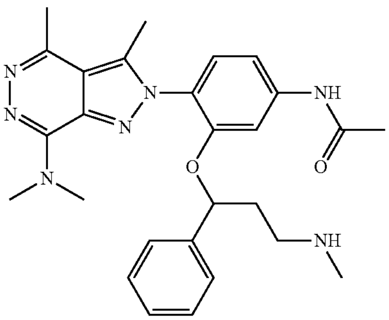 [SMILES: CNCCC(Oc1cc(NC(C)=O)ccc1-n1nc2c(N(C)C)nnc(C)c2c1C)c1ccccc1] | N-(4-(7-(dimethylamino)-3,4-dimethyl-2H-pyrazolo[3,4-d]pyridazin-2-yl)-3-(3-(methylamino)-1-phenylpropoxy)phenyl)acetamide |
| 83 | 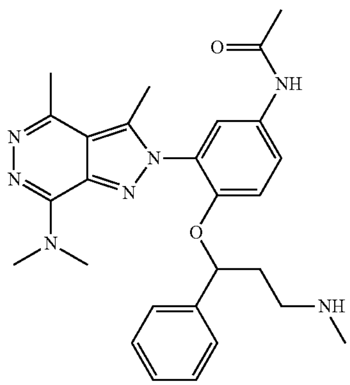 [SMILES: CNCCC(Oc1ccc(NC(C)=O)cc1-n1nc2c(N(C)C)nnc(C)c2c1C)c1ccccc1] | N-(3-(7-(dimethylamino)-3,4-dimethyl-2H-pyrazolo[3,4-d]pyridazin-2-yl)-4-(3-(methylamino)-1-phenylpropoxy)phenyl)acetamide |
| 84 | 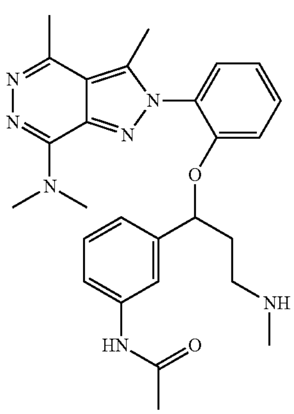 [SMILES: CNCCC(Oc1ccccc1-n1nc2c(N(C)C)nnc(C)c2c1C)c1cccc(NC(C)=O)c1] | N-(3-(1-(2-(7-(dimethylamino)-3,4-dimethyl-2H-pyrazolo[3,4-d]pyridazin-2-yl)phenoxy)-3-(methylamino)propyl)phenyl)acetamide |
| 85 | 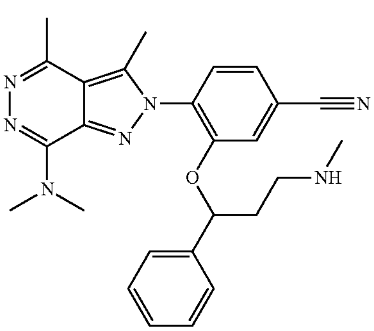 [SMILES: CNCCC(Oc1cc(C#N)ccc1-n1nc2c(N(C)C)nnc(C)c2c1C)c1ccccc1] | 4-(7-(Dimethylamino)-3,4-dimethyl-2H-pyrazolo[3,4-d]pyridazin-2-yl)-3-(3-(methylamino)-1-phenylpropoxy)benzonitrile |

| EX | Structure | Chemical name |
|---|---|---|
| 86 | 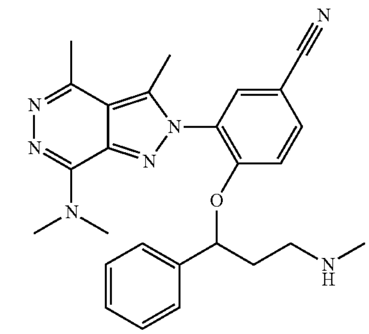 [SMILES: CNCCC(Oc1ccc(C#N)cc1-n1nc2c(N(C)C)nnc(C)c2c1C)c1ccccc1] | 3-(7-(dimethylamino)-3,4-dimethyl-2H-pyrazolo[3,4-d]pyridazin-2-yl)-4-(3-(methylamino)-1-phenylpropoxy)benzonitrile |
| 87 | 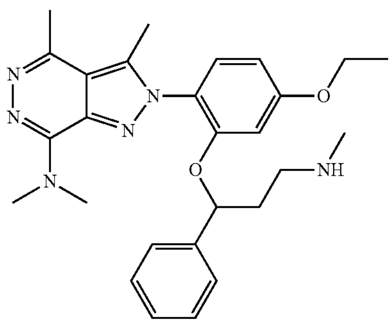 [SMILES: CCOc1ccc(-n2nc3c(N(C)C)nnc(C)c3c2C)c(OC(CCNC)c2ccccc2)c1] | 2-(4-Ethoxy-2-(3-(methylamino)-1-phenylpropoxy)phenyl)-N,N,3,4-tetramethyl-2H-pyrazolo[3,4-d]pyridazin-7-amine |
| 88 | 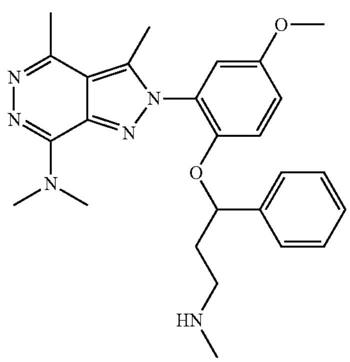 [SMILES: CNCCC(Oc1ccc(OC)cc1-n1nc2c(N(C)C)nnc(C)c2c1C)c1ccccc1] | 2-(5-methoxy-2-(3-(methylamino)-1-phenylpropoxy)phenyl)-N,N,3,4-tetramethyl-2H-pyrazolo[3,4-d]pyridazin-7-amine [1] |
| 89 | 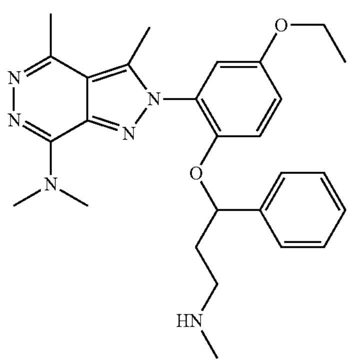 [SMILES: CCOc1ccc(OC(CCNC)c2ccccc2)c(-n2nc3c(N(C)C)nnc(C)c3c2C)c1] | 2-(5-ethoxy-2-(3-(methylamino)-1-phenylpropoxy)phenyl)-N,N,3,4-tetramethyl-2H-pyrazolo[3,4-d]pyridazin-7-amine |

| EX | Structure | Chemical name |
|---|---|---|
| 90 | 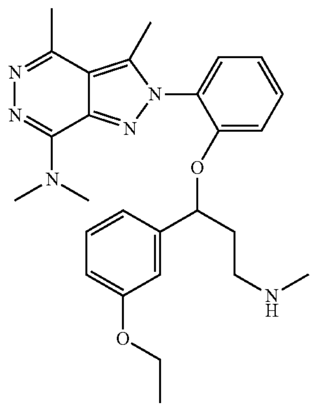 [SMILES: CCOc1cccc(C(CCNC)Oc2ccccc2-n2nc3c(N(C)C)nnc(C)c3c2C)c1] | 2-(2-(1-(3-ethoxyphenyl)-3-(methylamino)propoxy)phenyl)-N,N,3,4-tetramethyl-2H-pyrazolo[3,4-d]pyridazin-7-amine |
| 91 | 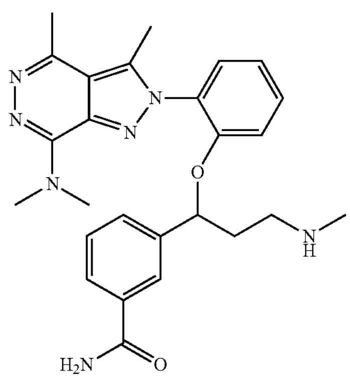 [SMILES: CNCCC(Oc1ccccc1-n1nc2c(N(C)C)nnc(C)c2c1C)c1cccc(C(N)=O)c1] | 3-(1-(2-(7-(Dimethylamino)-3,4-dimethyl-2H-pyrazolo[3,4-d]pyridazin-2-yl)phenoxy)-3-(methylamino)propyl)benzamide |
| 92 | 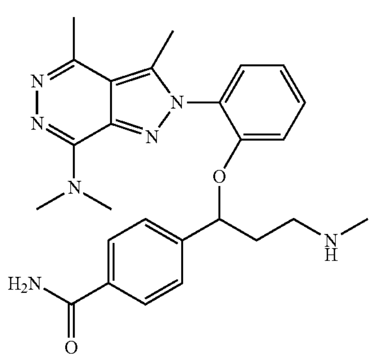 [SMILES: CNCCC(Oc1ccccc1-n1nc2c(N(C)C)nnc(C)c2c1C)c1ccc(C(N)=O)cc1] | 4-(1-(2-(7-(dimethylamino)-3,4-dimethyl-2H-pyrazolo[3,4-d]pyridazin-2-yl)phenoxy)-3-(methylamino)propyl)benzamide |
| 93 | 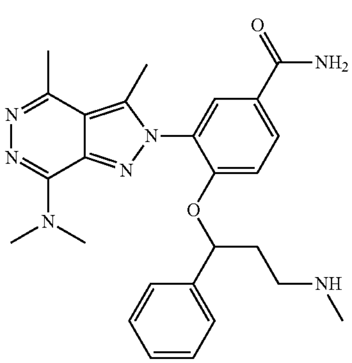 [SMILES: CNCCC(Oc1ccc(C(N)=O)cc1-n1nc2c(N(C)C)nnc(C)c2c1C)c1ccccc1] | 3-(7-(dimethylamino)-3,4-dimethyl-2H-pyrazolo[3,4-d]pyridazin-2-yl)-4-(3-(methylamino)-1-phenylpropoxy)benzamide |

-continued

| EX | Structure | Chemical name |
|---|---|---|
| 94 | 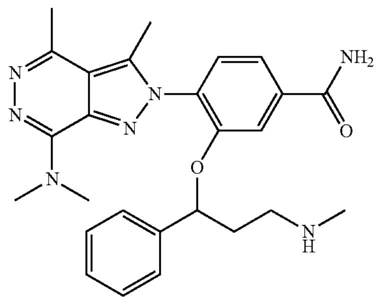 [SMILES: CNCCC(Oc1cc(C(N)=O)ccc1-n1nc2c(N(C)C)nnc(C)c2c1C)c1ccccc1] | 4-(7-(dimethylamino)-3,4-dimethyl-2H-pyrazolo[3,4-d]pyridazin-2-yl)-3-(3-(methylamino)-1-phenylpropoxy)benzamide |
| 95 | 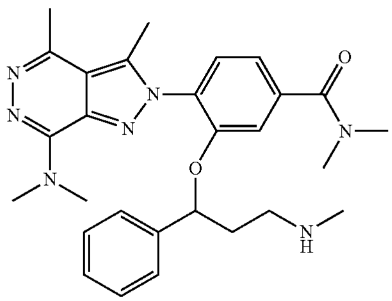 [SMILES: CNCCC(Oc1cc(C(=O)N(C)C)ccc1-n1nc2c(N(C)C)nnc(C)c2c1C)c1ccccc1] | 3-(1-(2-(7-(Dimethylamino)-3,4-dimethyl-2H-pyrazolo[3,4-d]pyridazin-2-yl)phenoxy)-3-(methylamino)propyl)benzamide |
| 96 | 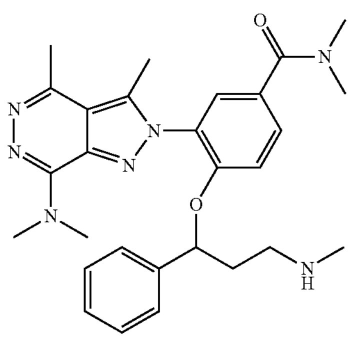 [SMILES: CNCCC(Oc1ccc(C(=O)N(C)C)cc1-n1nc2c(N(C)C)nnc(C)c2c1C)c1ccccc1] | 3-(7-(Dimethylamino)-3,4-dimethyl-2H-pyrazolo[3,4-d]pyridazin-2-yl)-N,N-dimethyl-4-(3-(methylamino)-1-phenylpropoxy)benzamide |
| 97 | 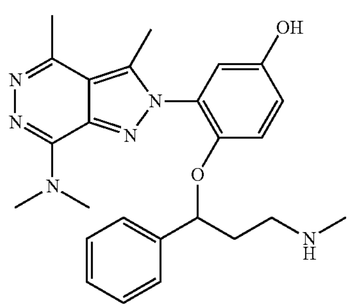 [SMILES: CNCCC(Oc1ccc(O)cc1-n1nc2c(N(C)C)nnc(C)c2c1C)c1ccccc1] | 3-(7-(Dimethylamino)-3,4-dimethyl-2H-pyrazolo[3,4-d]pyridazin-2-yl)-4-(3-(methylamino)-1-phenylpropoxy)phenol |
| 98 | 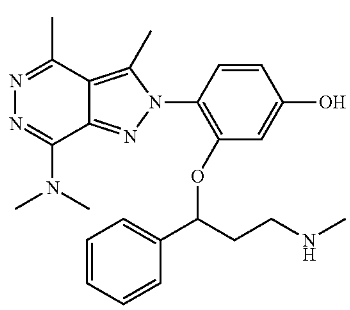 [SMILES: CNCCC(Oc1cc(O)ccc1-n1nc2c(N(C)C)nnc(C)c2c1C)c1ccccc1] | 4-(7-(dimethylamino)-3,4-dimethyl-2H-pyrazolo[3,4-d]pyridazin-2-yl)-3-(3-(methylamino)-1-phenylpropoxy)phenol |

| EX | Structure | Chemical name |
|---|---|---|
| 99 | 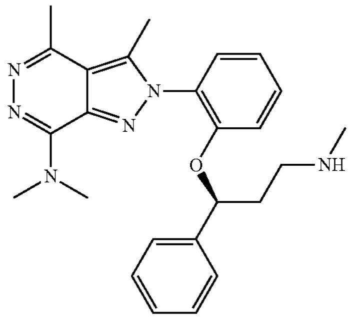 [SMILES: CNCC[C@H](Oc1ccccc1-n1nc2c(N(C)C)nnc(C)c2c1C)c1ccccc1] | (S)-N,N,3,4-Tetramethyl-2-(2-(3-(methylamino)-1-phenylpropoxy)phenyl)-2H-pyrazolo[3,4-d]pyridazin-7-amine |
| 100 | 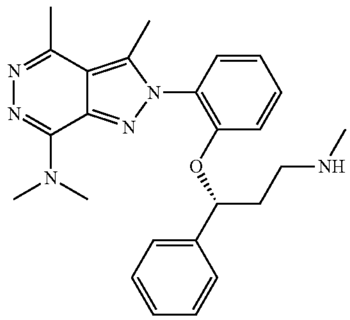 [SMILES: CNCC[C@@H](Oc1ccccc1-n1nc2c(N(C)C)nnc(C)c2c1C)c1ccccc1] | (R)-N,N,3,4-tetramethyl-2-(2-(3-(methylamino)-1-phenylpropoxy)phenyl)-2H-pyrazolo[3,4-d]pyridazin-7-amine |
| 101 | 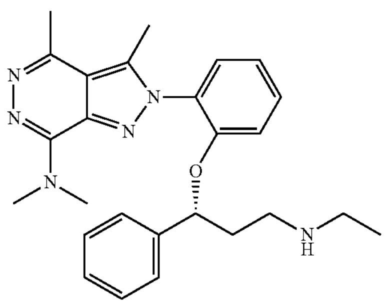 [SMILES: CCNCC[C@@H](Oc1ccccc1-n1nc2c(N(C)C)nnc(C)c2c1C)c1ccccc1] | (R)-2-(2-(3-(Ethylamino)-1-phenylpropoxy)phenyl)-N,N,3,4-tetramethyl-2H-pyrazolo[3,4-d]pyridazin-7-amine |
| 102 | 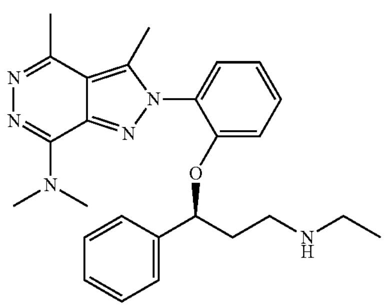 [SMILES: CCNCC[C@H](Oc1ccccc1-n1nc2c(N(C)C)nnc(C)c2c1C)c1ccccc1] | (S)-2-(2-(3-(ethylamino)-1-phenylpropoxy)phenyl)-N,N,3,4-tetramethyl-2H-pyrazolo[3,4-d]pyridazin-7-amine |
| 103 | 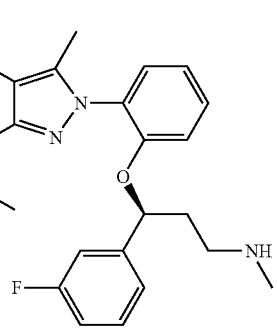 | (S)-2-(2-(1-(3-Fluorophenyl)-3-(methylamino)propoxy)phenyl)-N,N,3,4-tetramethyl-2H-pyrazolo[3,4-d]pyridazin-7-amine |

| EX | Structure | Chemical name |
|---|---|---|
| 104 | | (R)-2-(2-(1-(3-fluorophenyl)-3-(methylamino)propoxy)phenyl)-N,N,3,4-tetramethyl-2H-pyrazolo[3,4-d]pyridazin-7-amine | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_x$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

the alkyl, alkenyl or alkynyl in $R_x$ or $R_{x'}$, if substituted, is substituted with one or more substituent/s selected from —$OR_9$, halogen, —CN, haloalkyl, haloalkoxy and —$NR_9R_{9'}$;

wherein $R_9$ and $R_{9'}$ are independently selected from hydrogen, unsubstituted $C_{1-6}$ alkyl, unsubstituted $C_{2-6}$ alkenyl and unsubstituted $C_{2-6}$ alkynyl;

the aryl, heterocyclyl or cycloalkyl, also in alkylaryl, alkylcycloalkyl and alkylheterocyclyl, in $R_x$, if substituted, is substituted with one or more substituent/s selected from halogen, —$R_{10}$, —$OR_{10}$, —$NO_2$, —$NR_{10}R_{10'}$, —$NR_{10}C(O)R_{10'}$, —$NR_{10}S(O)_2R_{10'}$, —$S(O)_2NR_{10}R_{10'}$, —$NR_{10}C(O)NR_{10'}R_{10''}$, —$SR_{10}$, —$S(O)R_{10}$, $S(O)_2R_{10}$, —CN, haloalkyl, haloalkoxy, —$C(O)OR_{10}$, —$C(O)NR_{10}R_{10'}$, —$OCH_2CH_2OR_{10}$, —$NR_{10}S(O)_2NR_{10'}R_{10''}$ and $C(CH_3)_2OR_{10}$;

wherein $R_{10}$, $R_{10'}$ and $R_{10''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_x$ is selected from substituted or unsubstituted $C_{1-6}$ alkyl, substituted or unsubstituted aryl, substituted or unsubstituted alkylaryl and substituted or unsubstituted heterocyclyl $R_{x'}$ is selected from hydrogen;

the alkyl, alkenyl or alkynyl in $R_x$, if substituted, is substituted with —$OR_9$;

wherein $R_9$ and $R_{9'}$ are unsubstituted $C_{1-6}$ alkyl;

the aryl, heterocyclyl or cycloalkyl, also in alkylaryl, alkylcycloalkyl and alkylheterocyclyl, in $R_x$, if substituted, is substituted with one or more substituent/s selected from halogen, —$OR_{10}$, —$NR_{10}C(O)R_{10'}$, —CN and —$C(O)NR_{10}R_{10'}$;

wherein $R_{10}$, $R_{10'}$ and $R_{10''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from —$NR_6R_{6'}$ and substituted or unsubstituted N-containing-heterocyclyl;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;

wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'}$, $NR_{11}C(O)R_{11'}$, —$NR_{11}S(O)_2R_{11'}$, —$S(O)_2$ $NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OR_{11}$, —$NR_{11}S(O)_2NR_{11'}R_{11''}$, $C(CH_3)_2OR_{11}$, substituted or unsubstituted alkylaryl, substituted or unsubstituted alkylcycloalkyl and substituted or unsubstituted alkyheterocyclyl;

wherein the alkyl, alkenyl or alkynyl in $R_6$ or $R_{6'}$, if substituted, is substituted with one or more substituent/s selected from —$OR_{11}$, halogen, —CN, haloalkyl, haloalkoxy and —$NR_{11}R_{11'}$;
wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from —$NR_6R_{6'}$ and substituted or unsubstituted N-containing-heterocyclyl;
  wherein $R_6$ and $R_{6'}$ are independently selected from hydrogen, substituted or unsubstituted $C_{1-6}$ alkyl, substituted or unsubstituted alkylaryl, substituted or unsubstituted cycloalkyl and substituted or unsubstituted alkylcycloalkyl;
  wherein said cycloalkyl, aryl or heterocyclyl in $R_1$ or $R_6$, also in alkylaryl, alkylcycloalkyl and alkylheterocyclyl, if substituted, is substituted with one or more substituent/s selected from —$R_{11}$ and substituted or unsubstituted alkylaryl;
  wherein the alkyl, alkenyl or alkynyl in $R_6$ or $R_{6'}$, if substituted, is substituted with one or more substituent/s selected from —$OR_{11}$ and halogen;
  wherein $R_{11}$ is unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_2$ is selected from hydrogen, —$NR_7R_{7'}$, —CN, —$CHR_7R_{7'}$ and substituted or unsubstituted heterocyclyl;
  wherein $R_7$ and $R_{7'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
  wherein said cycloalkyl, aryl or heterocyclyl in $R_2$, $R_7$ or $R_{7'}$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'}$, $NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OR_{12}$, —$NR_{12}S(O)_2NR_{12'}R_{12''}$ and $C(CH_3)_2OR_{12}$;
  wherein the alkyl, alkenyl or alkynyl in $R_7$ or $R_{7'}$, if substituted, is substituted with one or more substituent/s selected from —$OR_{12}$, halogen, —CN, haloalkyl, haloalkoxy and —$NR_{12}R_{12'}$;
  wherein $R_{12}$, $R_{12'}$ and $R_{12''}$ are independently selected from hydrogen, unsubstituted $C_{1-6}$ alkyl, and unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_2$ is selected from hydrogen, —$NR_7R_{7'}$, —CN, —$CHR_7R_{7'}$ and substituted or unsubstituted heterocyclyl;
  wherein $R_7$ and $R_{7'}$ are independently selected from hydrogen, substituted or unsubstituted $C_{1-6}$ alkyl, substituted or unsubstituted aryl and substituted or unsubstituted alkylaryl;
  wherein said cycloalkyl, aryl or heterocyclyl in $R_2$, $R_7$ or $R_{7'}$, also in alkylaryl, alkylcycloalkyl and alkylheterocyclyl, if substituted, is substituted with one or more substituent/s selected from —$R_{12}$ and —$OR_{12}$;
  wherein the alkyl, alkenyl or alkynyl in $R_7$ or $R_{7'}$, if substituted, is substituted with one or more substituent/s selected from —$OR_{12}$ and —$NR_{12}R_{12'}$;
  wherein $R_{12}$ and $R_{12'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in $R_x$, $R_{x'}$, $R_6$, $R_{6'}$, $R_7$ or $R_{7'}$, if substituted, is substituted with one or more substituent/s selected from —$OR_{13}$, halogen, —CN, haloalkyl, haloalkoxy and —$NR_{13}R_{13'}$;
  wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl, also in alkylaryl, alkylcycloalkyl and alkylheterocyclyl, other than those defined in $R_x$, $R_1$, $R_2$, $R_6$, $R_{6'}$, $R_7$ or $R_{7'}$, if substituted, is substituted with one or more substituent/s selected from halogen, —$R_{14}$, —$OR_{14}$, —$NO_2$, —$NR_{14}R_{14'}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OR_{14}$, —$NR_{14}S(O)_2NR_{14'}R_{14''}$ and $C(CH_3)_2OR_{14}$;
  wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_x$ or $R_{x'}$, if substituted, is substituted with one or more substituent/s selected from —$OR_9$, halogen, —CN, haloalkyl, haloalkoxy and —$NR_9R_{9'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_x$ or $R_{x'}$, if substituted, is substituted with —$OR_9$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the aryl, heterocyclyl or cycloalkyl, also in alkylaryl, alkylcycloalkyl and alkylheterocyclyl, in $R_x$, if substituted, is substituted with one or more substituent/s selected from halogen, —$R_{10}$, —$OR_{10}$, —$NO_2$, —$NR_{10}R_{10'}$, —$NR_{10}C(O)R_{10'}$, —$NR_{10}S(O)_2R_{10'}$, —$S(O)_2NR_{10}R_{10'}$, —$NR_{10}C(O)NR_{10'}R_{10''}$, —$SR_{10}$, —$S(O)R_{10}$, $S(O)_2R_{10}$, —CN, haloalkyl, haloalkoxy, —$C(O)OR_{10}$, —$C(O)NR_{10}R_{10'}$, —$OCH_2CH_2OR_{10}$, —$NR_{10}S(O)_2NR_{10'}R_{10''}$ and $C(CH_3)_2OR_{10}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the aryl, heterocyclyl or cycloalkyl, also in alkylaryl, alkylcycloalkyl and alkylheterocyclyl, in $R_x$, if substituted, is substituted with one or more substituent/s selected from halogen, —$OR_{10}$, —$NR_{10}C(O)R_{10'}$, —CN and —$C(O)NR_{10}R_{10'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'}$, $NR_{11}C(O)R_{11'}$, —$NR_{11}S(O)_2R_{11'}$, —$S(O)_2$ $NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OR_{11}$, —$NR_{11}S(O)_2NR_{11'}R_{11''}$, $C(CH_3)_2OR_{11}$, substituted or unsubstituted alkylaryl, substituted or unsubstituted alkylcycloalkyl and substituted or unsubstituted alkyheterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the cycloalkyl, aryl or heterocyclyl in $R_1$ or $R_6$, also in alkylaryl, alkylcycloalkyl and alkylheterocyclyl, if substituted, is substituted with one or more substituent/s selected from —$R_{11}$ and substituted or unsubstituted alkylaryl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_6$ or $R_{6'}$, if substituted, is substituted with one or more substituent/s selected from —$OR_1$, halogen, —CN, haloalkyl, haloalkoxy and —$NR_{11}R_{11'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_6$ or $R_{6'}$, if substituted, is substituted with one or more substituent/s selected from —$OR_{11}$ and halogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the cycloalkyl, aryl or heterocyclyl in $R_2$, $R_7$ or $R_{7'}$, also in alkylaryl, alkylcycloalkyl and alkylheterocyclyl, if substituted, is substituted with one or more substituent/s selected from halogen, —$R_{12}$, —$OR_{12}$, —$NO_2$, —$NR_{12}R_{12'}$, $NR_{12}C(O)R_{12'}$, —$NR_{12}S(O)_2R_{12'}$, —$S(O)_2$ $NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, —$OCH_2CH_2OR_{12}$, —$NR_{12}S(O)_2NR_{12'}R_{12''}$ and $C(CH_3)_2OR_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the cycloalkyl, aryl or heterocyclyl in $R_2$, $R_7$ or $R_{7'}$, also in alkylaryl, alkylcycloalkyl and alkylheterocyclyl, if substituted, is substituted with one or more substituent/s selected from —$R_{12}$ and —$OR_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_7$ or $R_{7'}$, if substituted, is substituted with one or more substituent/s selected from —$OR_{12}$, halogen, —CN, haloalkyl, haloalkoxy and —$NR_{12}R_{12'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl in $R_7$ or $R_{7'}$, if substituted, is substituted with one or more substituent/s selected from —$OR_{12}$ and —$NR_{12}R_{12'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the alkyl, alkenyl or alkynyl, other than those defined in $R_x$, $R_{x'}$, $R_6$, $R_{6'}$, $R_7$ or $R_{7'}$, if substituted, is substituted with one or more substituent/s selected from —$OR_{13}$, halogen, —CN, haloalkyl, haloalkoxy and —$NR_{13}R_{13'}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I),
the aryl, heterocyclyl or cycloalkyl, also in alkylaryl, alkylcycloalkyl and alkylheterocyclyl, other than those defined in $R_x$, $R_1$, $R_2$, $R_6$, $R_{6'}$, $R_7$ or $R_{7'}$, if substituted, is substituted with one or more substituent/s selected from halogen, —$R_{14}$, —$OR_{14}$, —$NO_2$, —$NR_{14}R_{14'}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14}$, —CN, haloalkyl, haloalkoxy, —$C(O)OR_{14}$, —$C(O)NR_{14}R_{14'}$, —$OCH_2CH_2OR_{14}$, —$NR_{14}S(O)_2NR_{14'}R_{14''}$ and $C(CH_3)_2OR_{14}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the halogen is fluorine, chlorine, iodine or bromine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)
the halogen is fluorine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)
the halogen is bromine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the haloalkyl is —$CF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I),
the haloalkoxy is —$OCF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the α2δ subunit, particularly the α2δ-1 subunit, of the voltage-gated calcium channel and the μ-opioid receptor it is a very preferred embodiment in which the compounds are selected which act as dual ligands of the α2δ subunit, particularly the α2δ-1 subunit, of the voltage-gated calcium channel and the μ-opioid receptor and especially compounds which have a binding expressed as $K_i$ responding to the following scales:

$K_i(\mu)$ is preferably <1000 nM, more preferably <500 nM, even more preferably <100 nM.

$K_i(\alpha 2\delta)$ is preferably <10000 nM, more preferably <5000 nM, even more preferably <500 nM.

In the following the phrase "compound of the invention" is used. This is to be understood as any compound according to the invention as described above according to general Formula (I), (I') and (I²').

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

For the sake of clarity the expression "a compound according to Formula (I), wherein e.g. $R_1$, $R_2$, $R_3$, $R_4$, $R_5$, $R_{5'}$, $R_c$, $R_{c'}$, X, W, m and p are as defined below in the detailed description" would (just like the expression "a compound of Formula (I) as defined in any one of claims e.g. 1 to 10" found in the claims) refer to "a compound according to Formula (I)", wherein the definitions of the respective substituents $R_1$ etc. (also from the cited claims) are applied. In addition, this would also mean, though (especially in regards to the claims) that also one or more disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims e.g. 1 to 10".

In general the processes are described below in the experimental part. The starting materials are commercially available or can be prepared by conventional methods.

A preferred aspect of the invention is also a process for the production of a compound according to Formula (I), following scheme 1, scheme 2 or scheme 3.

A preferred embodiment of the invention is a process for the production of a compound according to Formula (I), wherein, if not defined otherwise, m, n, p, $R_1$, $R_2$, $R_3$, $R_4$, $R_5$, $R_{5'}$, $R_c$, $R_{c'}$, W and X have the meanings defined in the description.

In a particular embodiment there is a process for the production of a compound according to Formula (I),

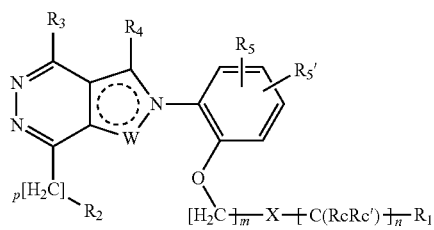

wherein the group $[CH_2]_pR_2$ is attached to the core structure through a carbon atom, said process comprises treating a compound of formula III

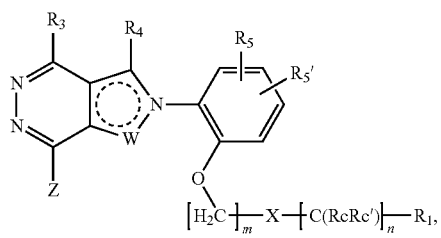

wherein Z represents a halogen, preferably chloro, or triflate with a suitable organometallic reagent of formula IVa,

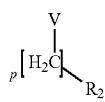

IVa wherein V represents a suitable organometallic reagent, preferably a boron or zinc reagent.

In a particular embodiment there is a process for the production of a compound according to Formula (I),

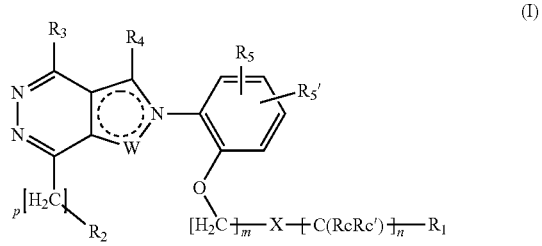

wherein the group $[CH_2]_pR_2$ is attached to the core structure through a nitrogen atom, said process comprises treating a compound of formula III

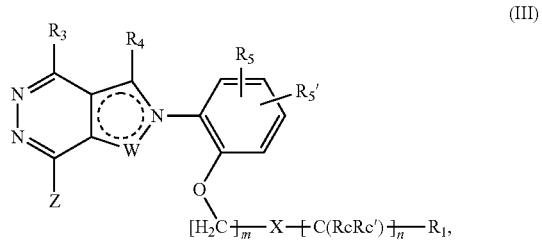

wherein Z represents a halogen, preferably chloro, or triflate with an amine of formula IVb HNR$_7$R$_7$.     IVb.

In a particular embodiment there is a process for the production of a compound according to Formula (I),

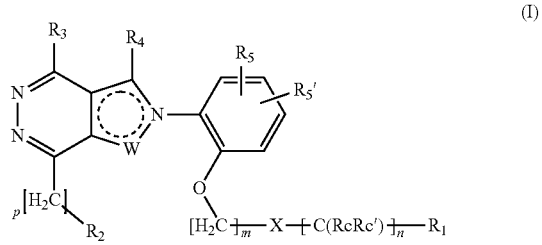

said process comprises treating a compound of formula VH

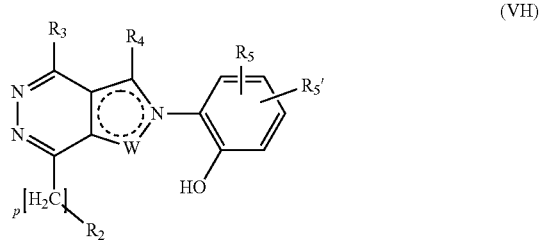

with a compound of formula VI

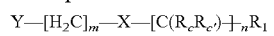

Y—[H$_2$C]$_m$—X—[C(R$_c$R$_{c'}$)]$_n$R$_1$     VI wherein Y represents a leaving group, such as halogen, mesylate, tosylate, nosylate or triflate, or OH.

In a particular embodiment there is a process for the production of a compound according to Formula (III), (IIIP) or (IIIH),

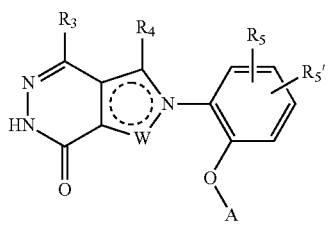

II A = [CH$_2$]$_m$—X—[C(R$_c$R$_{c'}$)]$_n$—R$_1$
IIP A = P

↓

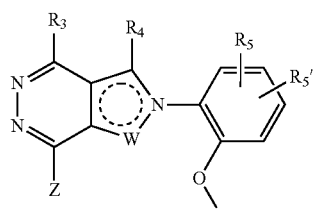

III A = [CH$_2$]$_m$—X—[C(R$_c$R$_{c'}$)]$_n$—R$_1$
IIIP A = P
IIIH A = H  } VI

Y—[H$_2$C]$_m$—X—[C(R$_c$R$_{c'}$)]$_n$—R$_1$  VI wherein P represents a suitable protecting group, such as alkyl or benzyl, preferably methyl, Y represents a leaving group, such as halogen, mesylate, tosylate, nosylate or triflate, or OH, and Z represents an halogen, preferably chloro, or triflate, following the method described for scheme 1.

In a particular embodiment there is a process for the production of a compound according to Formula (I), (VP) or (VH),

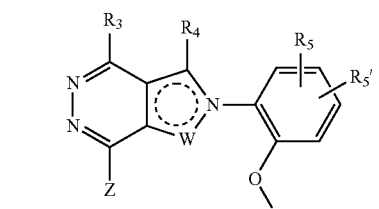

III A = [CH$_2$]$_m$—X—[C(R$_c$R$_{c'}$)]$_n$—R$_1$
IIIP A = P
IIIH A = H  } VI

$_p$[H$_2$C]
R$_2$
IVa or HNR$_7$R$_{7'}$
IVb

↓

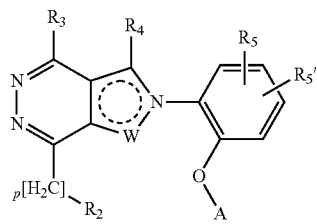

I A = [CH$_2$]$_m$—X—[C(R$_c$R$_{c'}$)]$_n$—R$_1$
VP A = P
VH A = H  } VI

Y—[H$_2$C]$_m$—X—[C(R$_c$R$_{c'}$)]$_n$—R$_1$  VI wherein P represents a suitable protecting group, such as alkyl or benzyl, preferably methyl, Y represents a leaving group, such as halogen, mesylate, tosylate, nosylate or triflate, or OH, and Z represents an halogen, preferably chloro, or triflate, following the method described for scheme 1.

In a particular embodiment there is a process for the production of a compound according to Formula (IX) or (IXP),

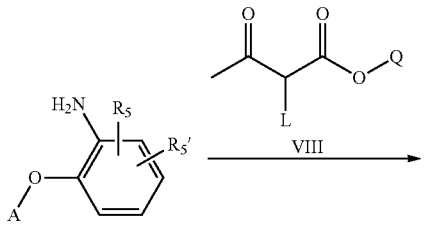

VII A = [CH$_2$]$_m$—X—[C(R$_c$R$_{c'}$)]$_n$—R$_1$
VIIP A = P

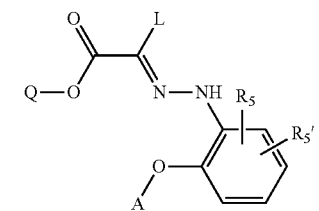

IX A = [CH$_2$]$_m$—X—[C(R$_c$R$_{c'}$)]$_n$—R$_1$
IXP A = P wherein P represents a suitable protecting group, such as alkyl or benzyl, preferably methyl, and L represents halogen, like fluorine, chlorine, bromine or iodine, following the method described for scheme 2.

In a particular embodiment there is a process for the production of a compound according to Formula (XI) or (XIP),

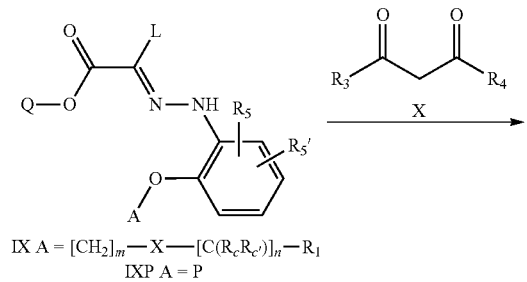

IX A = [CH$_2$]$_m$—X—[C(R$_c$R$_{c'}$)]$_n$—R$_1$
IXP A = P

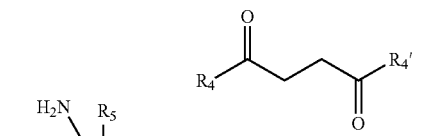

VII A = [CH$_2$]$_m$—X—[C(R$_c$R$_{c'}$)]$_n$—R$_1$
VIIP A = P

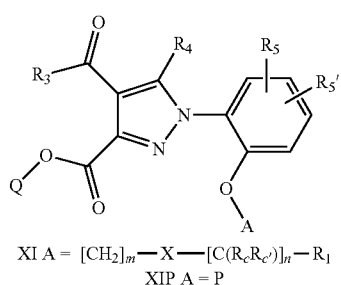

XI A = [CH$_2$]$_m$—X—[C(R$_c$R$_{c'}$)]$_n$—R$_1$
XIP A = P

XIII A = [CH$_2$]$_m$—X—[C(R$_c$R$_{c'}$)]$_n$—R$_1$
XIIIP A = P wherein P represents a suitable protecting group, such as alkyl or benzyl, preferably methyl, and Q represents an alkyl group, preferably methyl or ethyl, following the method described for scheme 2.

In a particular embodiment there is a process for the production of a compound according to Formula (IIa) or (IIaP), wherein P represents a suitable protecting group, such as alkyl or benzyl, preferably methyl, following the method described for scheme 3.

In a particular embodiment there is a process for the production of a compound according to Formula (XV) or (XVP),

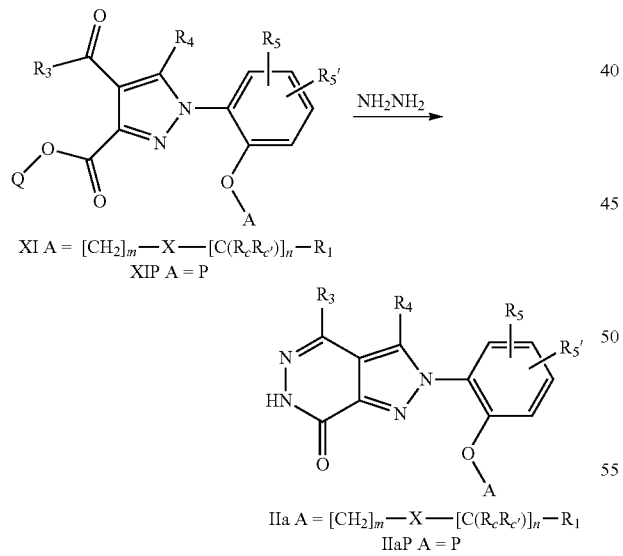

XI A = [CH$_2$]$_m$—X—[C(R$_c$R$_{c'}$)]$_n$—R$_1$
XIP A = P

IIa A = [CH$_2$]$_m$—X—[C(R$_c$R$_{c'}$)]$_n$—R$_1$
IIaP A = P

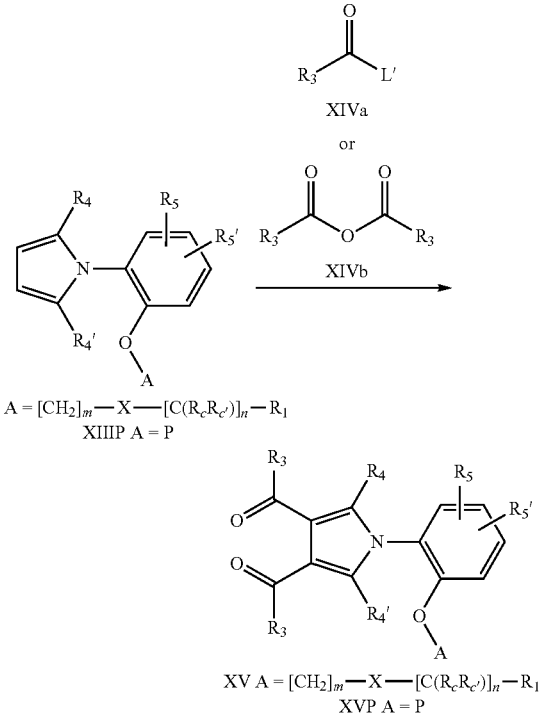

XIII A = [CH$_2$]$_m$—X—[C(R$_c$R$_{c'}$)]$_n$—R$_1$
XIIIP A = P

XV A = [CH$_2$]$_m$—X—[C(R$_c$R$_{c'}$)]$_n$—R$_1$
XVP A = P wherein P represents a suitable protecting group, such as alkyl or benzyl, preferably methyl, and Q represents an alkyl group, preferably methyl or ethyl, following the method described for scheme 2.

In a particular embodiment there is a process for the production of a compound according to Formula (XIII) or (XIIIP), wherein P represents a suitable protecting group, such as alkyl or benzyl, preferably methyl, and L' represents halogen, like fluorine, chlorine, bromine or iodine, following the method described for scheme 3.

In a particular embodiment there is a process for the production of a compound according to Formula (Ib), (VbP) or (VbH),

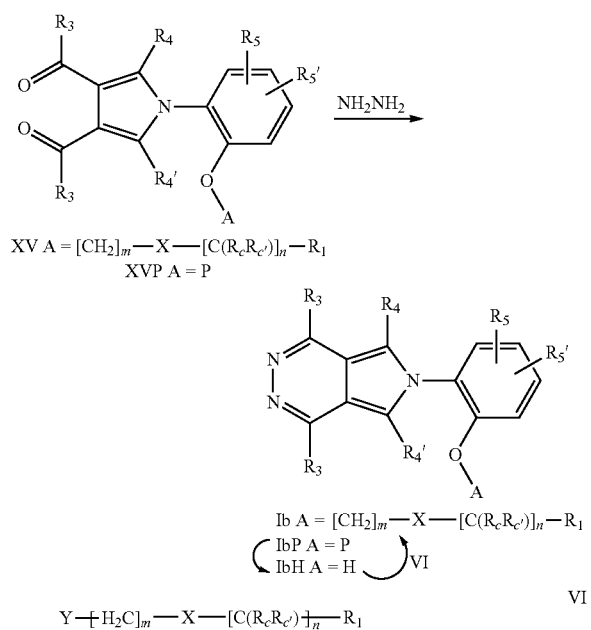

XV A = [CH₂]ₘ—X—[C(R_cR_c')]ₙ—R₁
XVP A = P

Ib A = [CH₂]ₘ—X—[C(R_cR_c')]ₙ—R₁
IbP A = P
IbH A = H

Y—[H₂C]ₘ—X—[C(R_cR_c')]ₙ—R₁     VI wherein P represents a suitable protecting group, such as alkyl or benzyl, preferably methyl, Y represents a leaving group, such as halogen, mesylate, tosylate, nosylate or triflate, or OH, following the method described for scheme 3.

In a particular embodiment there is a process for the production of a compound according to Formula (I), by the reduction reaction of a carbonyl derivative with a suitable reductive reagent, preferably sodium borohydride, in an organic solvent, preferably MeOH, to afford a hydroxyl compound.

In a particular embodiment there is a process for the production of a compound according to Formula (I), by deprotection reaction of a compound of formula I that contains an amine protecting group such as a carbamate, preferably tert-butoxy carbonyl, by any suitable method, such as treatment with an acid, preferably HCl or trifluoroacetic acid in an appropriate solvent such as 1,4-dioxane, DCM, ethyl acetate or a mixture of an organic solvent and water.

In a particular embodiment there is a process for the production of a compound according to Formula (I), by reductive amination reaction of a compound of formula I that contains an amino group with an aldehyde, preferably carried out with a reductive reagent, preferably sodium triacetoxyborohydride, in an organic solvent, preferably DCE, in the presence of an organic base, preferably DIPEA or TEA. Alternatively, the reaction can be carried out in the presence of an acid, preferably acetic acid.

In a particular embodiment there is a process for the production of a compound according to Formula (I), by reaction of a compound of formula I that contains an amino group with an alkylating reagent, in the presence of a base, preferably DIPEA or K₂CO₃, in an organic solvent, preferably acetonitrile, at suitable temperature, such as in the range of 0-120° C.

In a particular embodiment there is a process for the production of a compound according to Formula (I), by reaction of a compound of formula I that contains an amino group with a vinyl derivative, in an organic solvent, preferably 2-methoxyethanol, at suitable temperature, such as in the range of 20-140° C.

In a particular embodiment a compound of Formula (II),

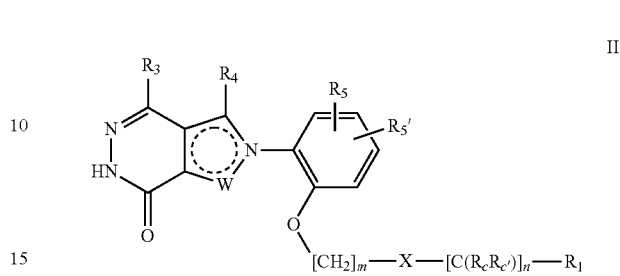

is used for the preparation of compounds of Formula (I).

In a particular embodiment a compound of Formula (IIP),

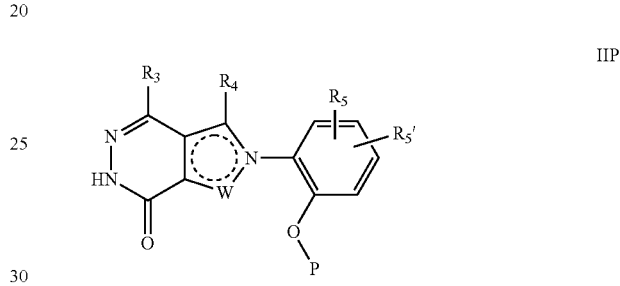

wherein P is a suitable protecting group, such as alkyl or benzyl, preferably methyl, is used for the preparation of compounds of Formula (I).

In a particular embodiment a compound of Formula (III),

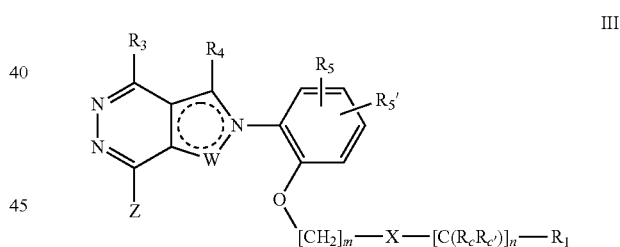

is used for the preparation of compounds of Formula (I).

In a particular embodiment a compound of Formula (IIIP),

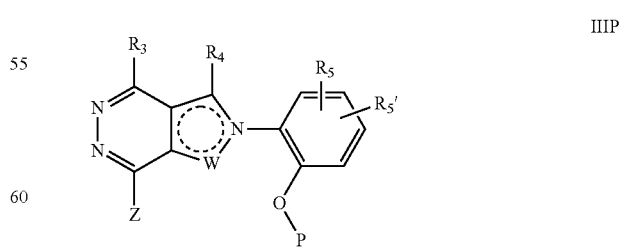

wherein P is a suitable protecting group, such as alkyl or benzyl, preferably methyl, and Z represents an halogen, preferably chloro, or triflate, is used for the preparation of compounds of Formula (I).

In a particular embodiment a compound of Formula (IIIH),

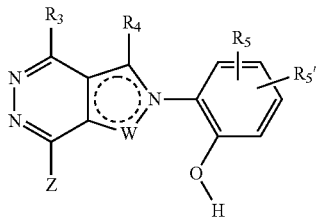 IIIH wherein Z represents an halogen, preferably chloro, or triflate, is used for the preparation of compounds of Formula (I).

In a particular embodiment a compound of Formula (IVa),

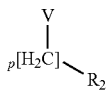 IVa wherein V represents a suitable organometallic reagent, preferably a boron or zinc reagent, is used for the preparation of compounds of Formula (I).

In a particular embodiment a compound of Formula (IVb),

 IVb

HNR₇R₇' is used for the preparation of compounds of Formula (I).

In a particular embodiment a compound of Formula (VP),

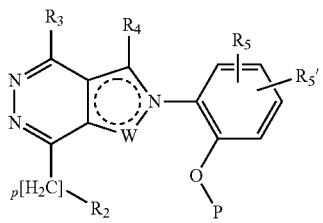 VP wherein P is a suitable protecting group, such as alkyl or benzyl, preferably methyl, is used for the preparation of compounds of Formula (I).

In a particular embodiment a compound of Formula (VH),

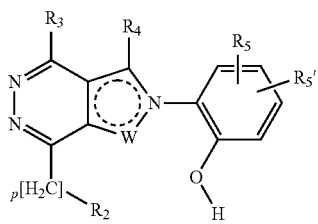 VH is used for the preparation of compounds of Formula (I).

In a particular embodiment a compound of Formula (VI),

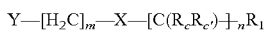 VI

Y—[H₂C]ₘ—X—[C(R_cR_c')]ₙ—R₁ wherein Y is a leaving group, such as halogen, mesylate, tosylate, nosylate or triflate, or OH, is used for the preparation of compounds of Formula (I).

In a particular embodiment a compound of Formula (VII),

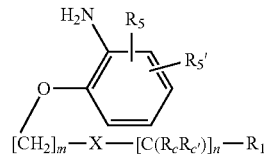 VII is used for the preparation of compounds of Formula (I).

In a particular embodiment a compound of Formula (VIIP),

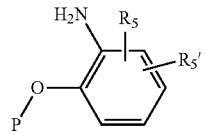 VIIP wherein P is a suitable protecting group, such as alkyl or benzyl, preferably methyl, is used for the preparation of compounds of Formula (I).

In a particular embodiment a compound of Formula (VIII),

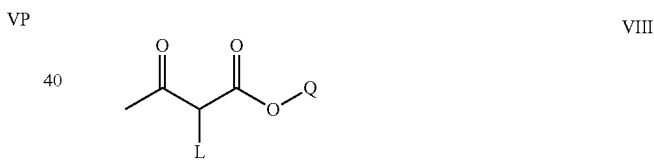 VIII wherein Q is an alkyl group, preferably methyl or ethyl, is used for the preparation of compounds of Formula (I).

In a particular embodiment a compound of Formula (IX),

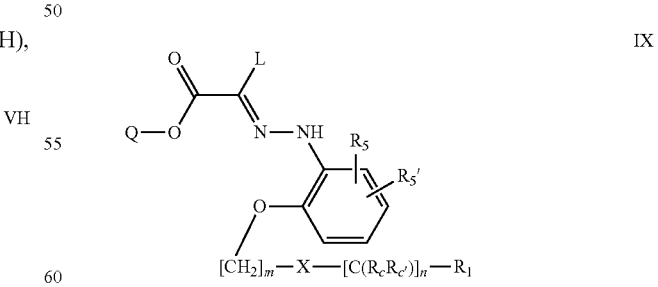 IX wherein L represents halogen, like fluorine, bromine, iodine or chlorine, is used for the preparation of compounds of Formula (I).

In a particular embodiment a compound of Formula (IXP),

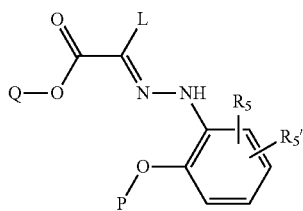

wherein P is a suitable protecting group, such as alkyl or benzyl, preferably methyl, Q is an alkyl group, preferably methyl or ethyl and L represents halogen, like fluorine, bromine, iodine or chlorine, is used for the preparation of compounds of Formula (I).

In a particular embodiment a compound of Formula (X),

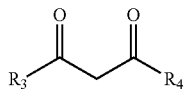

is used for the preparation of compounds of Formula (I).

In a particular embodiment a compound of Formula (XI),

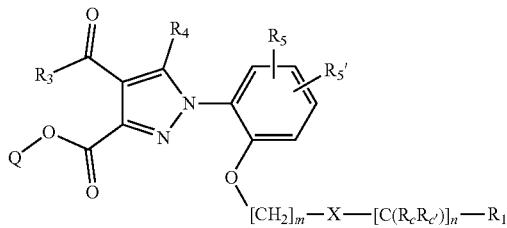

wherein Q is an alkyl group, preferably methyl or ethyl, is used for the preparation of compounds of Formula (I).

In a particular embodiment a compound of Formula (XIP),

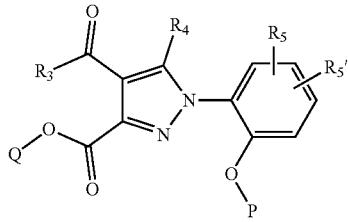

wherein P is a suitable protecting group, such as alkyl or benzyl, preferably methyl and Q is an alkyl group, preferably methyl or ethyl, is used for the preparation of compounds of Formula (I).

In a particular embodiment a compound of Formula (IIa),

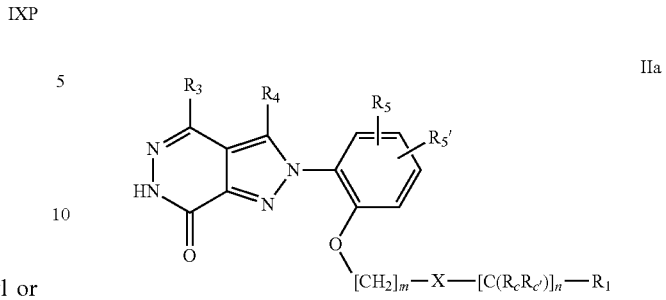

is used for the preparation of compounds of Formula (I).

In a particular embodiment a compound of Formula (IIaP),

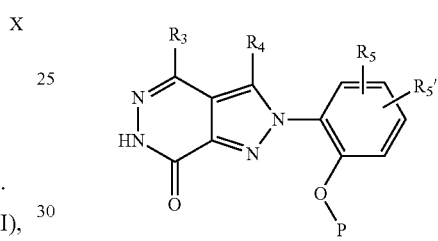

wherein P is a suitable protecting group, such as alkyl or benzyl, preferably methyl, is used for the preparation of compounds of Formula (I).

In a particular embodiment a compound of Formula (XII),

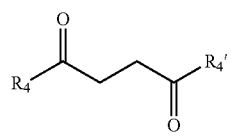

is used for the preparation of compounds of Formula (I).

In a particular embodiment a compound of Formula (XIII),

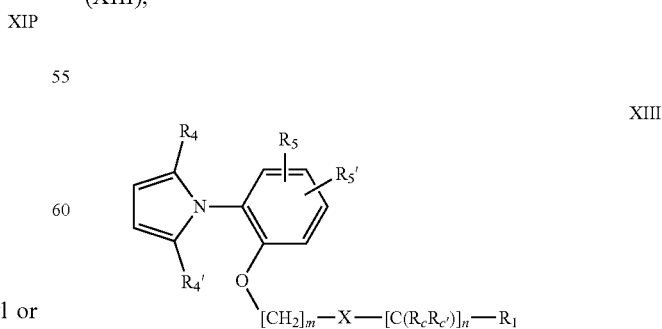

is used for the preparation of compounds of Formula (I).

In a particular embodiment a compound of Formula (XIIIP),

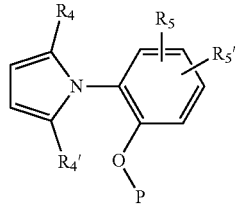
XIIIP wherein P is a suitable protecting group, such as alkyl or benzyl, preferably methyl, is used for the preparation of compounds of Formula (I).

In a particular embodiment a compound of Formula (XIVa),

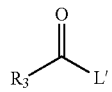
XIVa wherein L' represents halogen, like fluorine, bromine, iodine or chlorine, is used for the preparation of compounds of Formula (I).

In a particular embodiment a compound of Formula (XIVb),

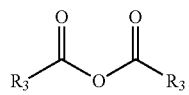
XIVb is used for the preparation of compounds of Formula (I).

In a particular embodiment a compound of Formula (XV),

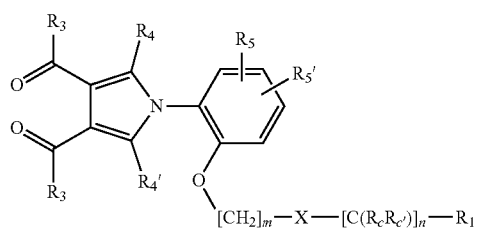
XV is used for the preparation of compounds of Formula (I).

In a particular embodiment a compound of Formula (XVP),

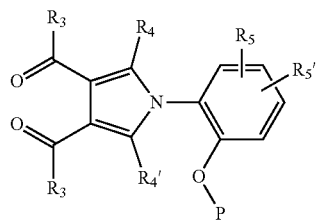
XVP wherein P is a suitable protecting group, such as alkyl or benzyl, preferably methyl, is used for the preparation of compounds of Formula (I).

In a particular embodiment a compound of Formula (Ib),

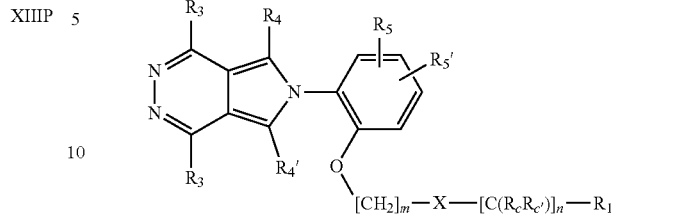
Ib is used for the preparation of compounds of Formula (I).

In a particular embodiment a compound of Formula (VbP),

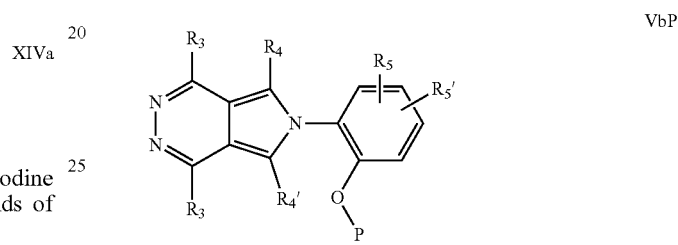
VbP wherein P is a suitable protecting group, such as alkyl or benzyl, preferably methyl, is used for the preparation of compounds of Formula (I).

In a particular embodiment a compound of Formula (VbH),

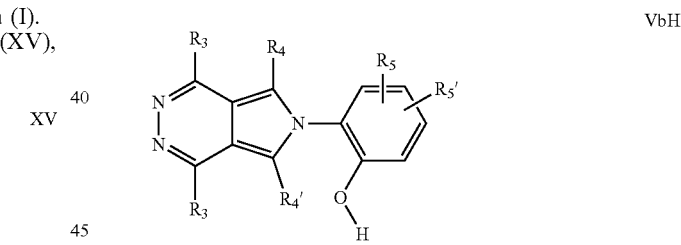
VbH is used for the preparation of compounds of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

General Experimental Part (Methods and Equipment of the Synthesis and Analysis

Synthesis Description

A two-step process is described for the preparation of compounds of general formula (I) starting from a compound of formula II, as shown in Scheme 1:

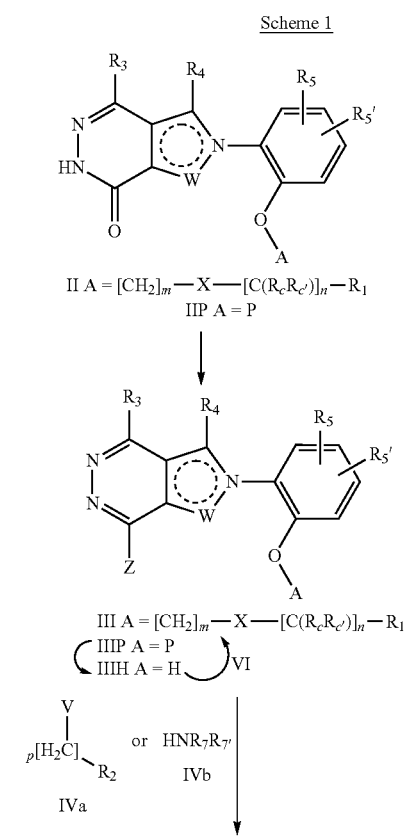

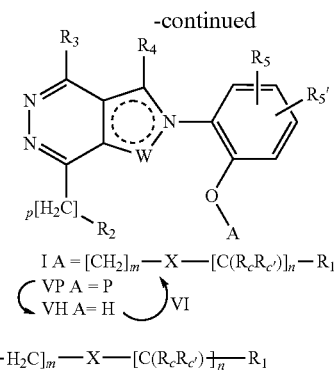

I A = [CH$_2$]$_m$—X—[C(R$_c$R$_{c'}$)]$_n$—R$_1$
VP A = P
VH A = H

Y—[H$_2$C]$_m$—X—[C(R$_c$R$_{c'}$)]$_n$—R$_1$    VI wherein R$_1$, R$_2$, R$_3$, R$_4$, R$_5$, R$_{5'}$, R$_7$, R$_{7'}$, R$_c$, R$_{c'}$, W, X, m, n and p have the meanings as defined above for a compound of formula (I), Y represents a leaving group (such as halogen, mesylate, tosylate, nosylate or triflate) or OH, Z represents an halogen (preferably chloro) or triflate, V represents a suitable organometallic reagent (preferably a boron or zinc reagent) and P represents a suitable protecting group (such as alkyl or benzyl, preferably methyl).

The two-step process can be carried out as described below:

Step 1: A compound of formula III, where Z represents chloro, can be prepared from a compound of formula II by treating a compound of formula II with a suitable chlorinating reagent such as phosphorus oxychloride, optionally in the presence of a suitable solvent, preferably heating. When Z represents a triflate group, the reaction can be performed by treating a compound of formula II with trifluoromethane sulphonic anhydride in the presence of pyridine Step 2: A compound of formula I can be prepared by reacting a compound of formula III with suitable compounds and reaction conditions depending on the meaning of the group [CH$_2$]$_p$R$_2$:

a) When the group [CH$_2$]$_p$R$_2$ is attached through a carbon atom, the reaction can be performed by treating a compound of formula III with a suitable organometallic reagent of formula IVa, preferably a boron or zinc reagent. The coupling reaction is carried out using a suitable catalyst (preferably a Pd catalyst) and a suitable ligand (preferably a phosphine ligand) in the presence of a base, such as K$_2$CO$_3$ or Cs$_2$CO$_3$ in a suitable polar solvent, such as dioxane.

b) When the group [CH$_2$]$_p$R$_2$ is attached through a nitrogen atom, as is the case when p is 0 and R$_2$ is NR$_7$R$_{7'}$, the reaction can be performed by treating a compound of formula III with an amine of formula IVb. The reaction may be carried out in a suitable solvent, such as isopropanol, ethanol or acetonitrile; optionally in the presence of an organic base such as triethylamine or diisopropylethylamine or an inorganic base such as K$_2$CO$_3$ or Cs$_2$CO$_3$; at a suitable temperature comprised between room temperature and the reflux temperature, preferably heating, or alternatively, the reactions can be carried out in a microwave reactor. Alternatively, the amine of formula IVb can be introduced using a Pd catalysed procedure in the presence of a suitable catalyst, a suitable ligand (preferably a phosphine ligand), a suitable base and a suitable solvent, such as dioxane.

The group [CH$_2$]$_m$—X—[C(R$_c$R$_{c'}$)]$_n$—R$_1$ can be present from the beginning of the synthesis or alternatively it can be incorporated later on, by reaction of a compound of formula IIIH or VH with a compound of formula VI to render a compound of formula III or I, respectively. A compound of formula IIIH or VH may be obtained by deprotection of a compound of formula IIIP or VP, wherein P represents a suitable protecting group, such as alkyl or benzyl. When the protecting group P represents alkyl (preferably methyl), the deprotection is carried out by treating a compound of formula IIIP or VP with boron tribromide or boron trichloride, in a suitable solvent such as dichloromethane, at a suitable temperature, preferably cooling below 0° C. When the protecting group P represents benzyl, the deprotection reaction is preferably carried out by hydrogenation under hydrogen atmosphere and metal catalysis, preferably by the use of palladium over charcoal as catalyst in a suitable solvent such as methanol or ethanol, optionally in the presence of an acid such as acetic acid or hydrochloric acid.

The reaction of a phenol of formula IIIH or VH with a compound of formula VI to render a compound of formula III or I, respectively, may be carried out under different reaction conditions depending on the meaning of Y:

a) When Y represents a leaving group such as halogen, mesylate, tosylate, nosylate or triflate, compound VI is an alkylating agent. The alkylation reaction can be carried out in a suitable solvent, such as dimethylformamide dimethylformamide; in the presence of a base such as K$_2$CO$_3$, Cs$_2$CO$_3$, sodium hydride or potassium tert-butoxide; at a suitable temperature comprised between room temperature and the reflux temperature, preferably heating, or alternatively, the reaction can be carried out in a microwave reactor. Additionally, an activating agent such as sodium iodide can be used.

b) When Y represents OH, the reaction may be carried out by treating a phenol of formula IIIH or VH with an alcohol of formula VI in the presence of an azo compound such as 1,1'-(azodicarbonyl)dipiperidine (ADDP), diisopropylazodicarboxylate (DIAD) or diethyl azodicarboxylate (DEAD) and a phosphine such as tributylphosphine or triphenylphoshine. The reaction is carried out in a suitable solvent, such as toluene or tetrahydrofuran; at a suitable temperature comprised between room temperature and the reflux temperature, preferably heating, or alternatively, the reactions can be carried out in a microwave reactor.

Alternatively, a compound of formula VH can be synthesized from a compound of formula IIIH by reaction with a compound of formula IVa or IVb, following the conditions described for the preparation of a compound of formula I from a compound of formula III.

The compounds of formula IIIP and VP can be obtained following the two-step process described in Scheme 1, starting from a protected compound of formula IIP.

The compounds of formula II and IIP can be synthesized following procedures described in the literature. As a way of example, the preparation of compounds of general formula II or IIP, wherein W represents nitrogen (compounds of formula IIa or IIaP), is described in Scheme 2:

Scheme 2

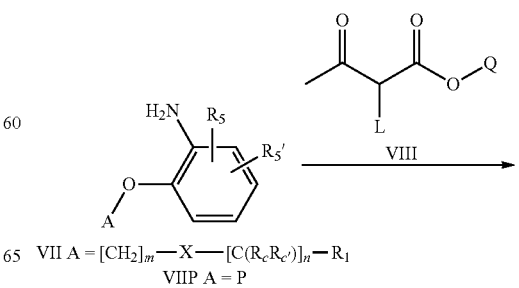

VII A = [CH$_2$]$_m$—X—[C(R$_c$R$_{c'}$)]$_n$—R$_1$
VIIP A = P

-continued

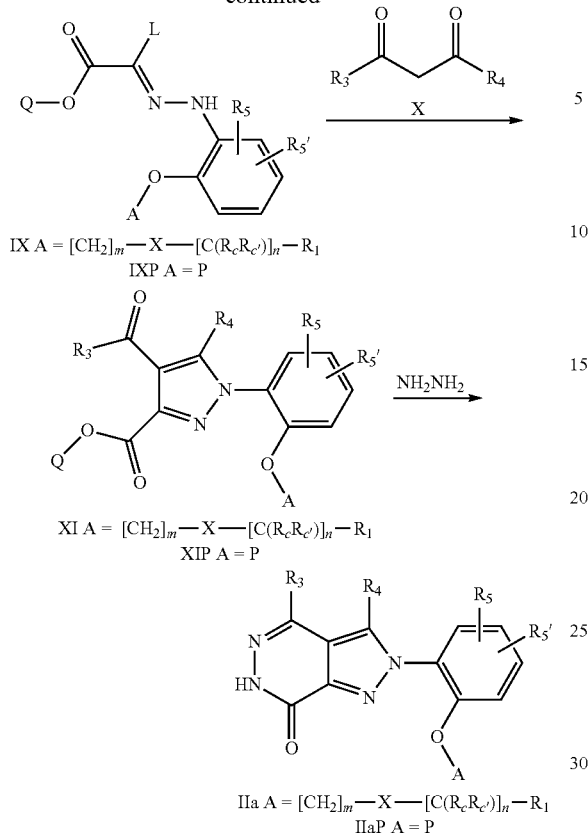

Scheme 3

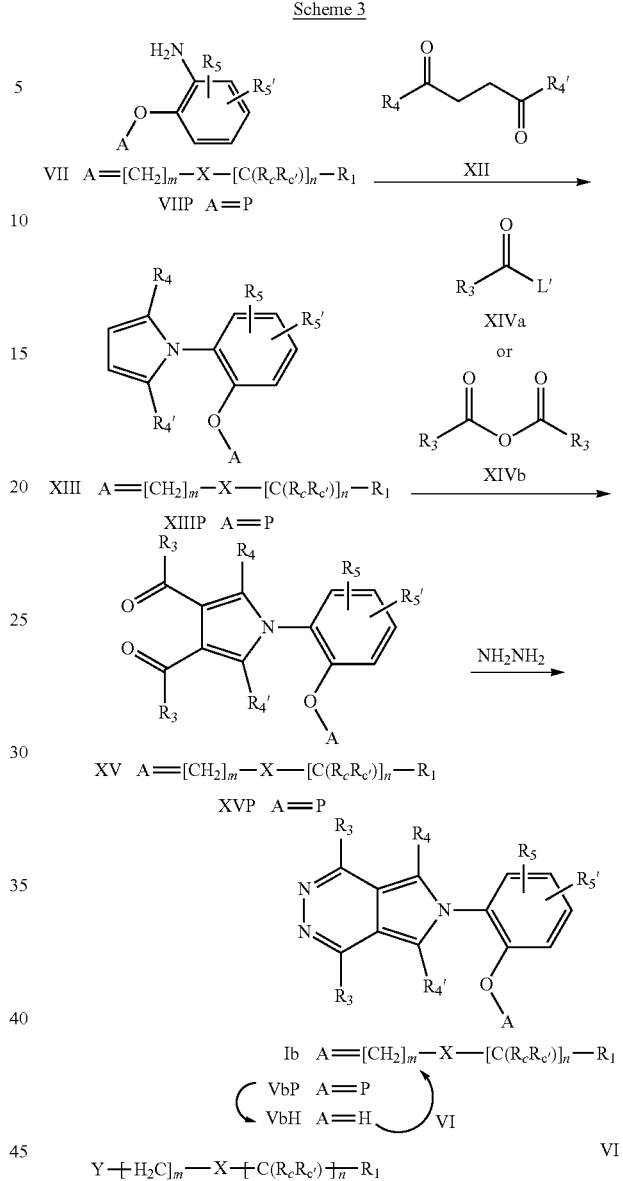

wherein $R_1$, $R_2$, $R_3$, $R_4$, $R_5$, $R_{5'}$, $R_c$, $R_{c'}$, X, m, n and p have the meanings as defined above for a compound of formula (I), L represents halogen, Q represents an alkyl group (preferably methyl or ethyl) and P represents a suitable protecting group (such as alkyl or benzyl, preferably methyl).

The reaction of an aniline compound of formula VII with a compound of formula VIII under suitable reaction conditions renders a compound of formula IX. As a way of example, when L represents Cl, a compound of formula IX can be prepared by treating a compound of formula VII with sodium nitrite in a mixture of hydrochloric acid and ethanol at 0° C., followed by reaction with a compound of formula VIII in a mixture of ethanol and water at room temperature.

A compound of formula IX is then reacted with a di-keto compound of formula X to obtain a pyrazole of formula XI. The reaction is carried out in the presence of a strong base such as sodium ethoxide and in a suitable solvent such as ethanol.

Finally, treatment of a compound of formula XI with hydrazine, in a suitable solvent such as ethanol or acetic acid, at a suitable temperature, preferably heating, yields a compound of formula IIa.

Following the same sequence described in Scheme 2 starting from a conveniently protected aniline of formula VIIP, the corresponding protected compound of formula IIaP can be obtained.

The preparation of compounds of general formula I wherein W represents $CR_{4'}$ and wherein the group $[CH_2]_pR_2$ is the same as $R_3$ (compounds of formula Ib) can be carried out as described in Scheme 3:

wherein $R_1$, $R_3$, $R_4$, $R_{4'}$, $R_5$, $R_{5'}$, $R_c$, $R_{c'}$, X, m and n have the meanings as defined above for a compound of formula (I), L' represents halogen, Y represents a leaving group (such as halogen, mesylate, tosylate, nosylate or triflate) or OH and P represents a suitable protecting group (such as alkyl or benzyl, preferably methyl).

The reaction of an aniline compound of formula VII with a di-keto compound of formula XII, in a suitable solvent such as toluene and optionally in the presence of an acid such as acetic acid, renders a pyrrole compound of formula XIII.

A compound of formula XIII is then treated with an acylating agent of formula XIVa or XIVb to obtain an acylpyrrole of formula XV. The reaction is carried out, using a Lewis acid such as tin(IV) chloride or aluminum chloride, in a suitable solvent such as dichloromethane, dichloroethane or toluene, or mixtures thereof.

Finally, treatment of a compound of formula XV with hydrazine, in a suitable solvent such as ethanol or acetic acid or mixtures thereof, at a suitable temperature comprised between room temperature and the reflux temperature, preferably at room temperature, yields a compound of formula Ib.

Following the same sequence described in Scheme 3 starting from a conveniently protected aniline of formula VIIP, the corresponding precursor compound of formula VbP can be obtained.

The compounds of general formula IVa, IVb, VI, VII, VIIP, VIII, X, XII, XIVa and XIVb wherein $R_1$, $R_2$, $R_7$, $R_{7'}$, $R_c$, $R_{c'}$, $R_6$, $R_{6'}$, L, P, Q, V, Y, X, m, n and p have the meanings as defined above, are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions. As a way of example, some of these conversions include the reductive amination of an amino group with an aldehyde or ketone, or alternatively the reaction of an amino group with an alkylating agent, to prepare a further substituted amino group; the hydrolysis of a cyano group to yield the corresponding carboxamido group; the hydrolysis of a cyano group to yield the corresponding carboxylic acid; the conversion of a carboxylic acid into a carboxamide; the alkylation of a primary amide to yield a further substituted amide; the debenzylation of a N-benzyl amino group to render an NH amino group; the derivatization of a bromo or iodo-aryl, including its conversion to a cyano, hydroxy, alcoxy or N-acyl group, to prepare a substituted aryl compound; or the conversion of a cyano group into a nitrogenated 5-member-ring heterocycle.

In addition, the amino group present in $R_1$ in a compound of formula I can also be introduced from a suitable precursor by appropriate conversion reactions of functional groups, such as the conversion of an ester group into an amide followed by reduction to the corresponding amino group; the oxidation of a a hydroxyl group into an aldehyde or ketone followed by reductive amination with a suitable amine or the alkylation reaction of a leaving group (halogen or sulfonate group) with a suitable amine to incorporate the corresponding amino group.

In some of the processes described above it may be necessary to protect the reactive or labile groups present with suitable protecting groups, such as for example Boc (tert-butoxycarbonyl) for the protection of amino groups. The procedures for the introduction and removal of these protecting groups are well known in the art and can be found thoroughly described in the literature.

In addition, a compound of formula I that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

EXAMPLES

Intermediates and Examples

The following abbreviations are used in the examples:
ACN: acetonitrile
AcOH: acetic acid
Anh: anhydrous
Boc: tert-butoxycarbonyl
Conc: concentrated
Dba: dibenzylideneacetone
DCM: dichloromethane
DEA: diethylamine
DIPEA: N,N-diisopropylethylamine
DMA: dimethylacetamide
DMF: dimethylformamide
DMSO: dimethylsulfoxide
Eq: equivalent/s
EtOAc; ethyl acetate
EtOH: ethanol
EX: example
h: hour/s
HATU: 1-[bis(dimethylamino)methylene]-1H-1,2,3-triazolo [4,5-b]pyridinium 3-oxid hexafluorophosphate
HPLC: high performance liquid chromatography
INT: intermediate
IPA: isopropanol
LiHMDS: lithium bis(trimethylsilyl)amide
MeI: iodomethane
MeOH: methanol
MS: mass spectrometry
Min.: minutes
Quant: quantitative
Ret.: retention
r.t.: room temperature
Sat: saturated
TEA: triethylamine
TFA: trifluoroacetic acid
THF: tetrahydrofuran
Wt: weight
XantPhos: 4,5-bis(diphenylphosphino)-9,9-dimethylxanthene The following methods were used to determine the HPLC-MS spectra:
Method A
Column Xbridge C18 XP 30×4.6 mm, 2.5 um
Temperature: 40° C.
Flow: 2.0 mL/min
Gradient: $NH_4HCO_3$ pH 8: ACN (95:5)---0.5 min---(95:5)---6.5 min---(0:100)---1 min---(0:100)
Sample dissolved approx. 1 mg/mL in $NH_4HCO_3$ pH 8/ACN
Method B
Column: Gemini-NX 30×4.6 mm, 3 um
Temperature: 40° C.
Flow: 2.0 mL/min
Gradient: $NH_4HCO_3$ pH 8: ACN (95:5)---0.5 min---(95:5)---6.5 min---(0:100)---1 min---(0:100)
Sample dissolved approx. 1 mg/mL in $NH_4HCO_3$ pH 8/ACN
Method C
Column: Kinetex EVO 50×4.6 mm, 2.6 um
Temperature:40° C.
Flow: 2.0 mL/min
Gradient: $NH_4HCO_3$ pH 8: ACN (95:5)---0.5 min---(95:5)---6.5 min---(0:100)---1 min---(0:100)
Sample dissolved approx. 1 mg/mL in $NH_4HCO_3$ pH 8/ACN
Method D
Column: Kinetex EVO 50×4.6 mm, 2.6 um
Temperature:40° C.
Flow: 1.5 mL/min
Gradient: $NH_4HCO_3$ pH 8: ACN (95:5)---0.5 min---(95:5)---6.5 min---(0:100)---2 min---(0:100)
Sample dissolved approx. 1 mg/mL in $NH_4HCO_3$ pH 8/ACN

Synthesis of Intermediates

Intermediate 1

7-Chloro-2-(2-methoxyphenyl)-3,4-dimethyl-2H-pyrazolo[3,4-d]pyridazine

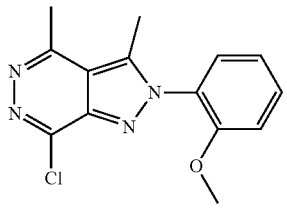 [SMILES: COc1ccccc1-n1nc2c(Cl)nnc(C)c2c1C]

Step 1. (Z)-Ethyl 2-chloro-2-(2-(2-methoxyphenyl)hydrazono)acetate: To a cooled solution of 2-methoxyaniline (10 g, 81 mmol) in a mixture of conc. HCl (16 mL) and EtOH (16 mL), a solution of sodium nitrite (6.1 g, 81 mmol) in water (24 mL) was added dropwise. After stirring for 20 min at 0° C., ethyl 2-chloro-3-oxobutanoate (11.2 mL, 81 mmol) was added. The mixture was diluted with EtOH/water 9:1 v/v (180 mL). Finally, sodium acetate (10.9 g, 133 mmol) and EtOH (75 mL) were added and it was stirred at room temperature for 2 h. Water (400 mL) was then added, the resulting suspension was filtered and the collected solids were dried under vacuum to afford the title compound (16.5 g, 79% yield).

Step 2. Ethyl 4-acetyl-1-(2-methoxyphenyl)-5-methyl-1H-pyrazole-3-carboxylate: Acetylacetone (6.6 mL, 64 mmol) was added to sodium ethoxide solution (21 wt % in EtOH, 24 mL, 64 mmol) and the mixture was stirred at r.t. overnight. Then, the product obtained in step 1 (16.5 g, 64 mmol) was added. The mixture was stirred at r.t. for 4 h and then it was left standing for 18 h without stirring. Water (234 mL) was added, the suspension was filtered and the solids were dried under vacuum to afford the title compound (18.3 g, 94% yield).

Step 3. 2-(2-Methoxyphenyl)-3,4-dimethyl-2H-pyrazolo[3,4-d]pyridazin-7(6H)-one: To a solution of the product obtained in step 2 (11.6 g, 57 mmol) in EtOH (112 mL), hydrazine (50-60% in water, 16.8 mL, 172 mmol) was added and the mixture was heated to reflux for 5 h. The suspension was cooled to room temperature and the solids were filtered, washed with cold EtOH and dried under vacuum to afford the title compound (11.5 g, 74% yield).

Step 4. Title compound: A mixture of the product obtained in step 3 (12.2 g, 45 mmol) and POCl$_3$ (183 mL) was heated at 100° C. for 3 h. POCl$_3$ was then distilled off. The residue was cooled to 0° C. and it was basified to pH 8 by careful addition of ice (exothermic reaction) and 28% NaOH (approx. 250 mL). The precipitated solids were stirred for 1-2 h at r.t. in order to obtain a filterable suspension and then they were collected by filtration, washed with water and dried under vacuum to yield the title compound (13.5 g, 100% yield).

This method was used for the preparation of Intermediates 2-3 using suitable starting materials:

| INT | Structure | Chemical name |
|---|---|---|
| 2 | 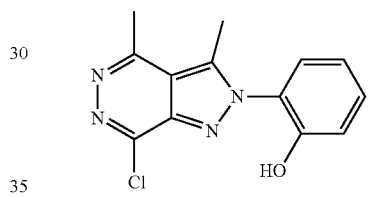 | 2-(5-bromo-2-methoxyphenyl)-7-chloro-3,4-dimethyl-2H-pyrazolo[3,4-d]pyridazine |
| 3 | 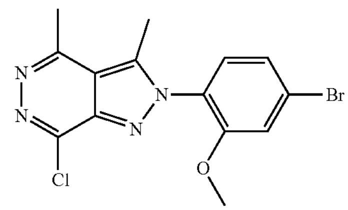 [SMILES: COc1cc(Br)ccc1-n1nc2c(Cl)nnc(C)c2c1C] | 2-(4-bromo-2-methoxyphenyl)-7-chloro-3,4-dimethyl-2H-pyrazolo[3,4-d]pyridazine |

Intermediate 4

2-(7-Chloro-3,4-dimethyl-2H-pyrazolo[3,4-d]pyridazin-2-yl)phenol

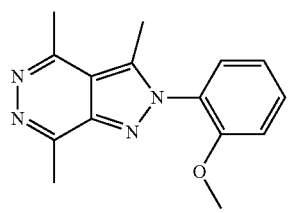 [SMILES: COc1ccccc1-n1nc2c(C)nnc(C)c2c1C]

To a solution of Intermediate 1 (1.5 g, 4.6 mmol) in DCM (20 mL), cooled at −78° C., BBr$_3$ (1 M solution in DCM, 6.2 mL, 6.2 mmol) was added dropwise. The reaction was slowly warmed to −30° C. and maintained at this temperature overnight in the freezer. Additional BBr$_3$ was added (13.9 mL, 13.9 mmol) and it was stirred at −30° C. for 3 h. Then 1 M NaOH was added to adjust the pH to 9-10 and it was extracted with DCM to remove residual starting material. The pH of the basic aqueous phase was then adjusted to 8, upon which precipitation occurred. The resultant suspension was filtered and the solids were washed with water and then dried under vacuum to obtain the title compound (0.76 g, 60% yield) as a crude product that was used as such without further purification.

Intermediate 5

2-(2-Methoxyphenyl)-3,4,7-trimethyl-2H-pyrazolo[3,4-d]pyridazine

This intermediate was prepared following the procedure described in Steps 1 to 3 of Intermediate 1, using 3-chloropentane-2,4-dione instead of ethyl 2-chloro-3-oxobutanoate in Step 1.

Intermediate 6

7-Isopropyl-2-(2-methoxyphenyl)-3,4-dimethyl-2H-pyrazolo[3,4-d]pyridazine

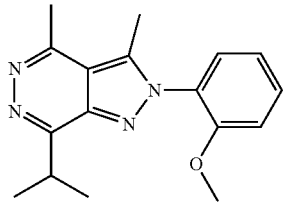 [SMILES: COc1ccccc1-n1nc2c(C(C)C)nnc(C)c2c1C]

Step 1. 2-(2-Methoxyphenyl)-3,4-dimethyl-7-(prop-1-en-2-yl)-2H-pyrazolo[3,4-d]pyridazine: A mixture of intermediate 1 (250 mg, 0.86 mmol) and K₂CO₃ (299 mg, 2.1 mmol) in 1,2-dimethoxyethane/water 3:1 (6.2 mL) was degassed by bubbling argon through the mixture. Finally, 4,4,5,5-tetramethyl-2-(prop-1-en-2-yl)-1,3,2-dioxaborolane (262 mg, 1.5 mmol) and Pd(PPh₃)₄ (100 mg, 0.087 mmol) were added. The reaction was heated at 100° C. under argon overnight. After cooling to r.t., the mixture was filtered through a pad of Celite, washing with EtOAc. The solvent was concentrated to dryness and the crude product was purified by flash chromatography, silica gel, gradient DCM to MeOH:DCM (1:4) to give the title compound (139 mg, 54% yield).

Step 2. 7-Isopropyl-2-(2-methoxyphenyl)-3,4-dimethyl-2H-pyrazolo[3,4-d]pyridazine: A suspension of the product obtained in Step 1 (317 mg, 1.07 mmol) and Pd (10% wt on carbon, 45 mg) in MeOH (5 mL) was stirred under 2 bars of H₂ overnight. The catalyst was filtered off and the solvent was removed under vacuum. The crude product was purified by flash chromatography, silica gel, gradient DCM to MeOH:DCM (1:4) to give the title compound (177 mg, 55% yield).

Intermediate 7

2-(2-Methoxyphenyl)-N,N-dimethyl-2H-pyrazolo[3,4-d]pyridazin-7-amine

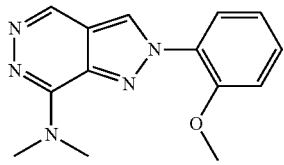 [SMILES: COc1ccccc1-n1cc2cnnc(N(C)C)c2n1]

Step 1. (E)-Ethyl 2-(2-(2-methoxyphenyl)hydrazono)propanoate: The compound was prepared following the procedure described in Step 1 of Intermediate 1, using ethyl 2-methyl-3-oxobutanoate instead of ethyl 2-chloro-3-oxobutanoate (4.8 g, overweight, 79 wt %, quantitative yield assumed).

Step 2. Ethyl 4-formyl-1-(2-methoxyphenyl)-1H-pyrazole-3-carboxylate: To a cooled solution of POCl₃ (4.55 mL) and DMF (4.9 mL), a solution of the product obtained in Step 1 (4.8 g, 79 wt %, 16.2 mmol) in DMF (16 mL) was added. The mixture was stirred for 1 h at 0° C. and then it was heated at 70° C. for 4 h. The reaction mixture was poured into ice (65 g), neutralized by addition of solid K₂CO₃ and extracted with EtOAc. The combined organic phases were washed with water, brine, dried over MgSO₄ and concentrated to dryness to afford the title compound (1.9 g, 43% yield).

Step 3. 2-(2-Methoxyphenyl)-2H-pyrazolo[3,4-d]pyridazin-7(6H)-one: Following the experimental procedure described in Step 3 of Intermediate 1, starting from the product obtained in Step 2 (1.9 g, 7.1 mmol), the title compound was obtained (0.95 g, 54% yield).

Step 4. 7-Chloro-2-(2-methoxyphenyl)-2H-pyrazolo[3,4-d]pyridazine: Following the experimental procedure described in Step 4 of Intermediate 1, starting from the product obtained in Step 3 (0.9 g, 3.9 mmol), the title compound was obtained (1.8 g, overweight, 55 wt %, quantitative yield assumed).

Step 5. Title compound: In a round-bottom pressure flask, a mixture of the product obtained in Step 4 (1 g, 3.9 mmol), TEA (1.1 mL, 7.8 mmol) and dimethylamine (2 M in THF, 2.36 mL, 4.72 mmol) in IPA (14 mL) was heated at 120° C. overnight. Then, water was added and the reaction mixture was extracted with DCM. The combined organic extracts were washed with brine, dried over MgSO₄ and concentrated to dryness. The crude compound was purified by flash chromatography, silica gel, gradient DCM to MeOH:DCM (1:4) to give the title compound (140 mg, 14% yield).

Synthesis of Examples

Example 1

2-(2-(3-(Ethylamino)-1-phenylpropoxy)phenyl)-N,N,3,4-tetramethyl-2H-pyrazolo[3,4-d]pyridazin-7-amine

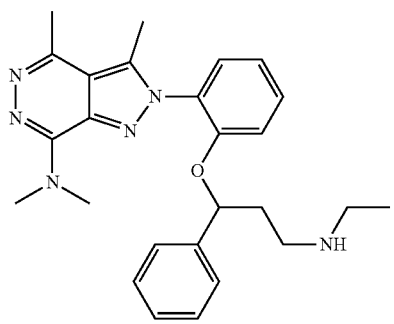 [SMILES: CCNCCC(Oc1ccccc1-n1nc2c(N(C)C)nnc(C)c2c1C)c1ccccc1]

Step 1. tert-Butyl (3-chloro-3-phenylpropyl)(ethyl)carbamate: To a cooled solution of 3-(ethylamino)-1-phenylpropan-1-ol (2.4 g, 13.4 mmol) in DCM (9.6 mL), a solution of SOCl₂ (1.17 mL, 16 mmol) in DCM (5 mL) was added dropwise. The mixture was stirred at r.t. for 2 h and then it was concentrated to dryness. The crude product thus obtained was dissolved in tert-butanol (12 mL). Then, 1.8 M NaOH solution (15 mL, 26 mmol) and di-tert-butyl dicarbonate (2.9 g, 13.3 mmol) were added and the reaction mixture was stirred for 15 min at r.t. Brine and DCM were added, the phases were separated and the aqueous layer was extracted with DCM. The combined organic phases were washed with brine, dried over $MgSO_4$ and concentrated to dryness to obtain the title compound as a crude product that was purified by flash chromatography, silica gel, gradient DCM to MeOH:DCM (1:4) to give the title compound (2 g, 56% yield).

Step 2. 2-(2-Methoxyphenyl)-N,N,3,4-tetramethyl-2H-pyrazolo[3,4-c]pyridazin-7-amine: In a round-bottom pressure flask, a mixture of Intermediate 1 (10 g, 35 mmol), TEA (9.6 mL, 69 mmol) and dimethylamine (2 M in THF, 21 mL, 41 mmol) in isopropanol (100 mL) was heated at 120° C. overnight. Then, water was added and the reaction mixture was extracted with DCM. The combined organic extracts were washed with brine, dried over $MgSO_4$ and concentrated to dryness to render the title compound (9.9 g, 96% yield).

Step 3. 2-(7-(Dimethylamino)-3,4-dimethyl-2H-pyrazolo[3,4-d]pyridazin-2-yl)phenol: To a solution of the product obtained in Step 2 (9.9 g, 33.4 mmol) in DCM (485 mL), cooled at −78° C., $BBr_3$ (1M solution in DCM, 167 mL, 167 mmol) was added dropwise. The reaction was slowly warmed to −30° C. and maintained overnight at this temperature in the freezer. Then 1 M NaOH was added to adjust pH to 9-10, DCM was distilled off and the solids were filtered and washed with water to obtain the title compound (8.3 g, 88% yield).

Step 4. tert-Butyl (3-(3-(7-(dimethylamino)-3,4-dimethyl-2H-pyrazolo[3,4-d]pyridazin-2-yl)phenoxy)-3-phenylpropyl)(ethyl)carbamate: A suspension of the product obtained in Step 3 (1.49 g, 5.25 mmol), $K_2CO_3$ (2.18 g, 15.78 mmol) and the product obtained in Step 1 (2.03 g, 6.83 mmol) in DMF (15 mL) was heated in a sealed tube at 100° C. overnight. Water and EtOAc were added to the cooled reaction mixture and the phases were separated. The aqueous phase was extracted twice with EtOAc. The combined organic phases were washed with brine, dried with sodium sulfate and concentrated to dryness. The residue was purified by flash chromatography, silica gel, gradient DCM to MeOH:DCM (1:4) to give the title compound (1.58 g, 55% yield).

Step 5. Title compound: To a solution of the product obtained in Step 4 (1.5 g, 2.9 mmol) in DCM (20 mL), TFA (2.2 mL, 29 mmol) was added and the reaction mixture was stirred at r.t. overnight. Additional TFA (1 mL, 13 mmol) was added to achieve full conversion. It was then concentrated to dryness and the residue was redissolved in DCM that was washed with 1 M NaOH. The organic phase was dried over MgSO4 and concentrated to dryness. The crude product was purified by flash chromatography, silica gel, gradient DCM to MeOH:DCM (1:4) to give the title compound (1.1 g, 85% yield). HPLC retention time (method A): 3.56 min; MS: 445.2 (M+H).

This method was used for the preparation of Examples 2-49 using suitable starting materials[1]:

| EX | Structure | Chemical name | Ret time (min) | MS (M + H) | HPLC Method |
|---|---|---|---|---|---|
| 2 | 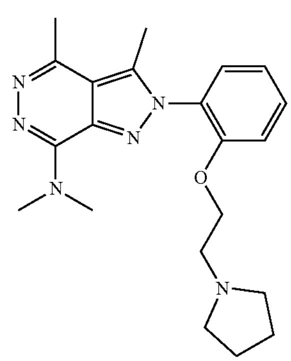 [SMILES: Cc1nnc(N(C)C)c2nn(-c3ccccc3OCCN3CCCC3)c(C)c12] | N,N,3,4-tetramethyl-2-(2-(2-(pyrrolidin-1-yl)ethoxy)phenyl)-2H-pyrazolo[3,4-d]pyridazin-7-amine | 3.05 | 381.2 | A |
| 3 | 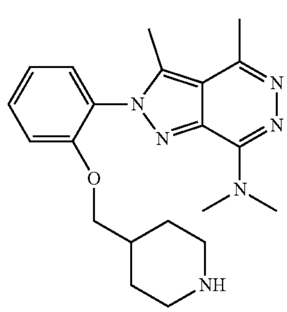 [SMILES: Cc1nnc(N(C)C)c2nn(-c3ccccc3OCC3CCNCC3)c(C)c12] | N,N,3,4-tetramethyl-2-(2-(piperidin-4-ylmethoxy)phenyl)-2H-pyrazolo[3,4-d]pyridazin-7-amine | 2.85 | 381.2 | A |

-continued

| EX | Structure | Chemical name | Ret time (min) | MS (M + H) | HPLC Method |
|---|---|---|---|---|---|
| 4 | 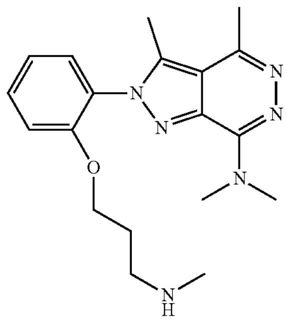 [SMILES: CNCCCOc1ccccc1-n1nc2c(N(C)C)nnc(C)c2c1C] | N,N,3,4-tetramethyl-2-(2-(3-(methylamino)propoxy)phenyl)-2H-pyrazolo[3,4-d]pyridazin-7-amine | 2.78 | 355.2 | A |
| 5 | 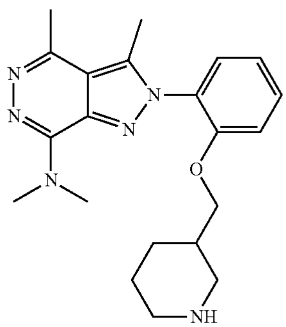 [SMILES: Cc1nnc(N(C)C)c2nn(-c3ccccc3OCC3CCCNC3)c(C)c12] | N,N,3,4-tetramethyl-2-(2-(piperidin-3-ylmethoxy)phenyl)-2H-pyrazolo[3,4-d]pyridazin-7-amine | 2.91 | 381.1 | A |
| 6 | 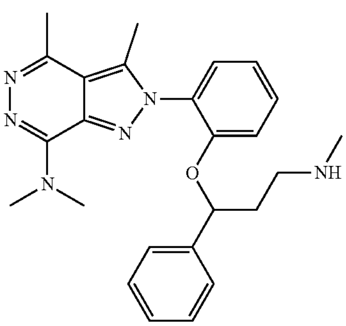 [SMILES: CNCCC(Oc1ccccc1-n1nc2c(N(C)C)nnc(C)c2c1C)c1ccccc1] | N,N,3,4-tetramethyl-2-(2-(3-(methylamino)-1-phenylpropoxy)phenyl)-2H-pyrazolo[3,4-d]pyridazin-7-amine | 3.43 | 431.2 | A |
| 7 | 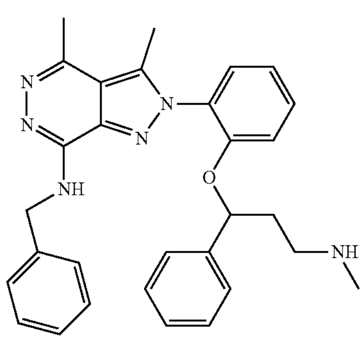 [SMILES: CNCCC(Oc1ccccc1-n1nc2c(NCc3ccccc3)nnc(C)c2c1C)c1ccccc1] | N-benzyl-3,4-dimethyl-2-(2-(3-(methylamino)-1-phenylpropoxy)phenyl)-2H-pyrazolo[3,4-d]pyridazin-7-amine | 3.65 | 493.2 | A |

-continued

| EX | Structure | Chemical name | Ret time (min) | MS (M + H) | HPLC Method |
|---|---|---|---|---|---|
| 8 | 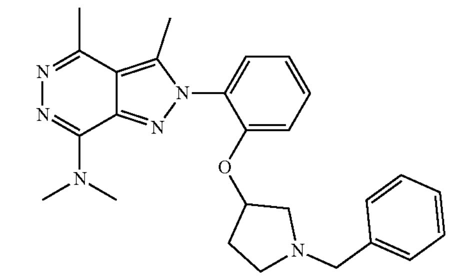 [SMILES: Cc1nnc(N(C)C)c2nn(-c3ccccc3OC3CCN(Cc4ccccc4)C3)c(C)c12] | 2-(2-((1-benzylpyrrolidin-3-yl)oxy)phenyl)-N,N,3,4-tetramethyl-2H-pyrazolo[3,4-d]pyridazin-7-amine | 4.13 | 443.2 | A |
| 9 | 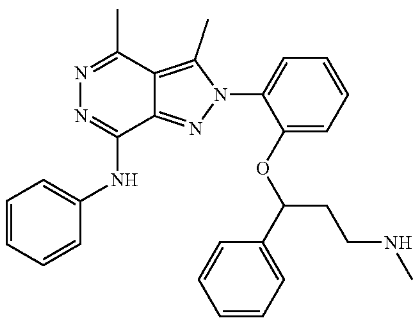 [SMILES: CNCCC(Oc1ccccc1-n1nc2c(Nc3ccccc3)nnc(C)c2c1C)c1ccccc1] | 3,4-dimethyl-2-(2-(3-(methylamino)-1-phenylpropoxy)phenyl)-N-phenyl-2H-pyrazolo[3,4-d]pyridazin-7-amine | 3.66 | 479.2 | A |
| 10 | 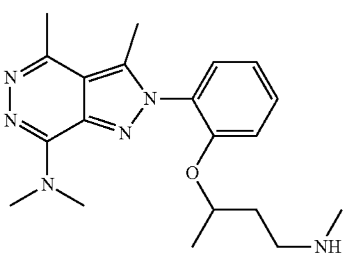 [SMILES: CNCCC(C)Oc1ccccc1-n1nc2c(N(C)C)nnc(C)c2c1C] | N,N,3,4-tetramethyl-2-(2-((4-(methylamino)butan-2-yl)oxy)phenyl)-2H-pyrazolo[3,4-d]pyridazin-7-amine | 2.87 | 369.2 | A |
| 11 | 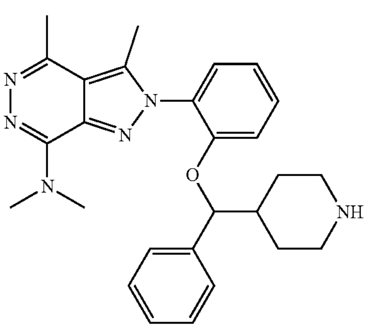 [SMILES: Cc1nnc(N(C)C)c2nn(-c3ccccc3OC(c3ccccc3)C3CCNCC3)c(C)c12] | N,N,3,4-tetramethyl-2-(2-(phenyl(piperidin-4-yl)methoxy)phenyl)-2H-pyrazolo[3,4-d]pyridazin-7-amine | 3.46 | 457.2 | A |
| 12 | 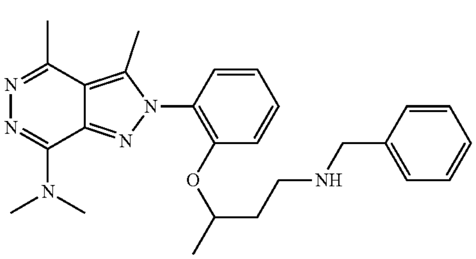 [SMILES: Cc1nnc(N(C)C)c2nn(-c3ccccc3OC(C)CCNCc3ccccc3)c(C)c12] | 2-(2-((4-(benzylamino)butan-2-yl)oxy)phenyl)-N,N,3,4-tetramethyl-2H-pyrazolo[3,4-d]pyridazin-7-amine | 3.84 | 445.2 | A |

-continued

| EX | Structure | Chemical name | Ret time (min) | MS (M + H) | HPLC Method |
|---|---|---|---|---|---|
| 13 | 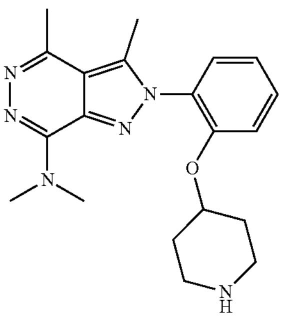 [SMILES: Cc1nnc(N(C)C)c2nn(-c3ccccc3OC3CCNCC3)c(C)c12] | N,N,3,4-tetramethyl-2-(2-(piperidin-4-yloxy)phenyl)-2H-pyrazolo[3,4-d]pyridazin-7-amine | 2.80 | 367.2 | A |
| 14 | 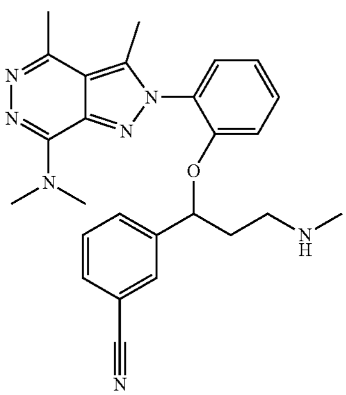 [SMILES: CNCCC(Oc1ccccc1-n1nc2c(N(C)C)nnc(C)c2c1C)c1cccc(C#N)c1] | 3-(1-(2-(7-(dimethylamino)-3,4-dimethyl-2H-pyrazolo[3,4-d]pyridazin-2-yl)phenoxy)-3-(methylamino)propyl)benzonitrile | 3.24 | 456.2 | A |
| 15 | 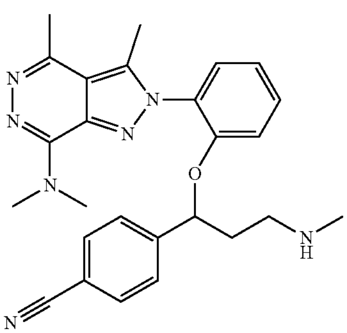 [SMILES: CNCCC(Oc1ccccc1-n1nc2c(N(C)C)nnc(C)c2c1C)c1ccc(C#N)cc1] | 4-(1-(2-(7-(dimethylamino)-3,4-dimethyl-2H-pyrazolo[3,4-d]pyridazin-2-yl)phenoxy)-3-(methylamino)propyl)benzonitrile | 3.26 | 456.2 | A |
| 16 | 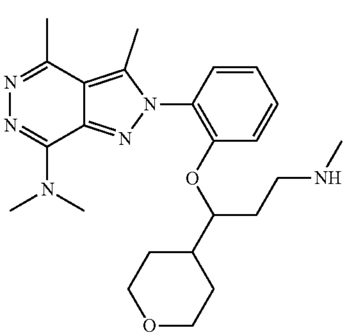 [SMILES: CNCCC(Oc1ccccc1-n1nc2c(N(C)C)nnc(C)c2c1C)C1CCOCC1] | N,N,3,4-tetramethyl-2-(2-(3-(methylamino)-1-(tetrahydro-2H-pyran-4-yl)propoxy)phenyl)-2H-pyrazolo[3,4-d]pyridazin-7-amine | 2.89 | 439.3 | A |

-continued

| EX | Structure | Chemical name | Ret time (min) | MS (M + H) | HPLC Method |
|---|---|---|---|---|---|
| 17 | 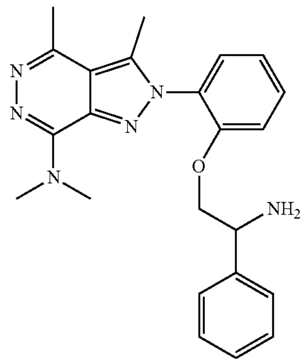 [SMILES: Cc1nnc(N(C)C)c2nn(-c3ccccc3OCC(N)c3ccccc3)c(C)c12] | 2-(2-(2-amino-2-phenylethoxy)phenyl)-N,N,3,4-tetramethyl-2H-pyrazolo[3,4-d]pyridazin-7-amine | 3.25 | 403.2 | A |
| 18 | 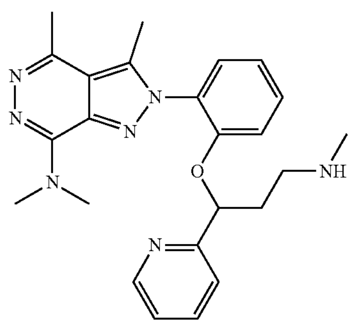 [SMILES: CNCCC(Oc1ccccc1-n1nc2c(N(C)C)nnc(C)c2c1C)c1ccccn1] | N,N,3,4-tetramethyl-2-(2-(3-(methylamino)-1-(pyridin-2-yl)propoxy)phenyl)-2H-pyrazolo[3,4-d]pyridazin-7-amine | 2.91 | 432.2 | A |
| 19 | 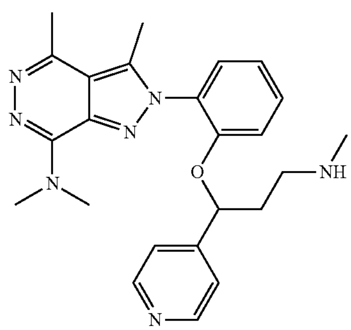 [SMILES: CNCCC(Oc1ccccc1-n1nc2c(N(C)C)nnc(C)c2c1C)c1ccncc1] | N,N,3,4-tetramethyl-2-(2-(3-(methylamino)-1-(pyridin-4-yl)propoxy)phenyl)-2H-pyrazolo[3,4-d]pyridazin-7-amine | 2.78 | 432.2 | A |
| 20 | 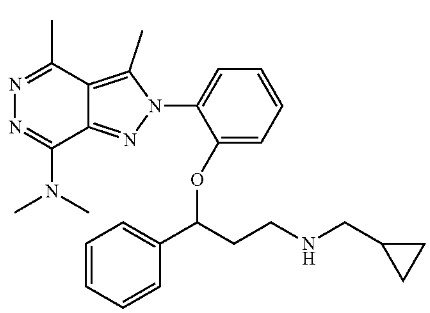 [SMILES: Cc1nnc(N(C)C)c2nn(-c3ccccc3OC(CCNCC3CC3)c3ccccc3)c(C)c12] | 2-(2-(3-((cyclopropylmethyl)amino)-1-phenylpropoxy)phenyl)-N,N,3,4-tetramethyl-2H-pyrazolo[3,4-d]pyridazin-7-amine | 3.76 | 471.3 | A |

-continued

| EX | Structure | Chemical name | Ret time (min) | MS (M + H) | HPLC Method |
|---|---|---|---|---|---|
| 21 | 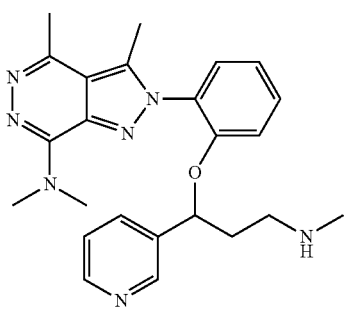 [SMILES: CNCCC(Oc1ccccc1-n1nc2c(N(C)C)nnc(C)c2c1C)c1cccnc1] | N,N,3,4-tetramethyl-2-(2-(3-(methylamino)-1-(pyridin-3-yl)propoxy)phenyl)-2H-pyrazolo[3,4-d]pyridazin-7-amine | 2.80 | 432.2 | A |
| 22 | 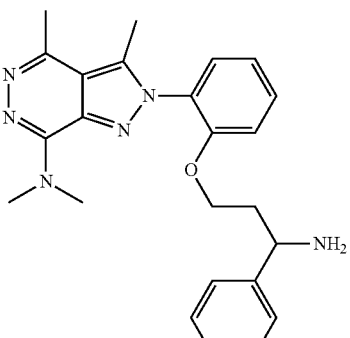 | 2-(2-(3-amino-3-phenylpropoxy)phenyl)-N,N,3,4-tetramethyl-2H-pyrazolo[3,4-d]pyridazin-7-amine | 3.53 | 417.2 | A |
| 23 | 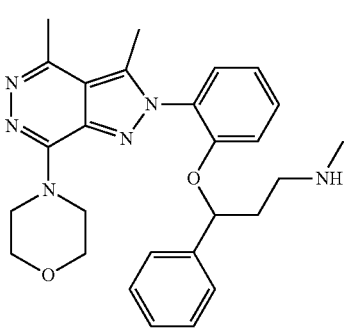 [SMILES: CNCCC(Oc1ccccc1-n1nc2c(N3CCOCC3)nnc(C)c2c1C)c1ccccc1] | 3-(2-(3,4-dimethyl-7-morpholino-2H-pyrazolo[3,4-d]pyridazin-2-yl)phenoxy)-N-methyl-3-phenylpropan-1-amine | 3.34 | 473.3 | A |
| 24 | 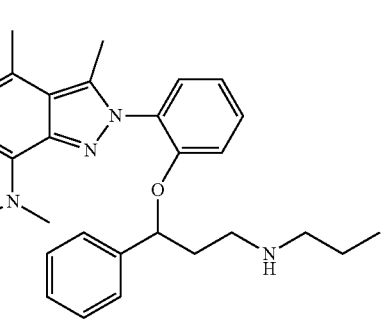 | N,N,3,4-tetramethyl-2-(2-(1-phenyl-3-(propylamino)propoxy)phenyl)-2H-pyrazolo[3,4-d]pyridazin-7-amine | 3.69 | 459.2 | A |

-continued

| EX | Structure | Chemical name | Ret time (min) | MS (M + H) | HPLC Method |
|---|---|---|---|---|---|
| 25 | 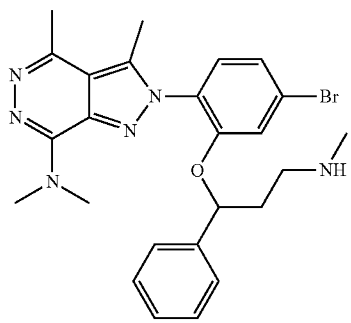 [SMILES: CNCCC(Oc1cc(Br)ccc1-n1nc2c(N(C)C)nnc(C)c2c1C)c1ccccc1] | 2-(4-bromo-2-(3-(methylamino)-1-phenylpropoxy)phenyl)-N,N,3,4-tetramethyl-2H-pyrazolo[3,4-d]pyridazin-7-amine | 3.85 | 509.1 | A |
| 26 | 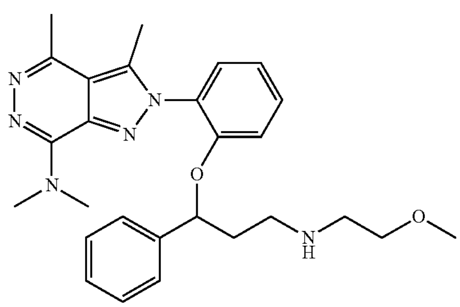 [SMILES: COCCNCCC(Oc1ccccc1-n1nc2c(N(C)C)nnc(C)c2c1C)c1ccccc1] | 2-(2-(3-((2-methoxyethyl)amino)-1-phenylpropoxy)phenyl)-N,N,3,4-tetramethyl-2H-pyrazolo[3,4-d]pyridazin-7-amine | 3.63 | 475.2 | A |
| 27 | 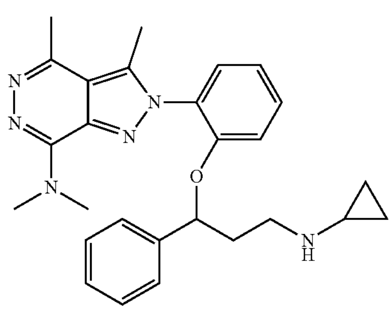 [SMILES: Cc1nnc(N(C)C)c2nn(-c3ccccc3OC(CCNC3CC3)c3ccccc3)c(C)c12] | 2-(2-(3-(cyclopropylamino)-1-phenylpropoxy)phenyl)-N,N,3,4-tetramethyl-2H-pyrazolo[3,4-d]pyridazin-7-amine | 4.00 | 457.2 | A |
| 28 | 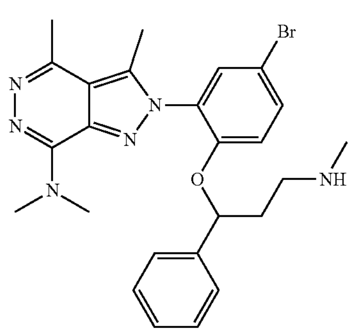 [SMILES: CNCCC(Oc1ccc(Br)cc1-n1nc2c(N(C)C)nnc(C)c2c1C)c1ccccc1] | 2-(5-bromo-2-(3-(methylamino)-1-phenylpropoxy)phenyl)-N,N,3,4-tetramethyl-2H-pyrazolo[3,4-d]pyridazin-7-amine | 3.83 | 509.1 | A |

-continued

| EX | Structure | Chemical name | Ret time (min) | MS (M + H) | HPLC Method |
|---|---|---|---|---|---|
| 29 | 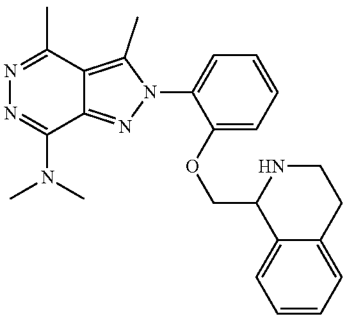 [SMILES: Cc1nnc(N(C)C)c2nn(-c3ccccc3OCC3NCCc4ccccc43)c(C)c12] | N,N,3,4-tetramethyl-2-(2-((1,2,3,4-tetrahydroisoquinolin-1-yl)methoxy)phenyl)-2H-pyrazolo[3,4-d]pyridazin-7-amine | 3.38 | 429.2 | A |
| 30 | 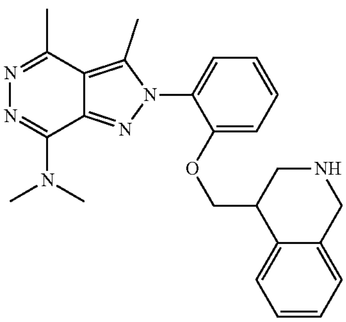 [SMILES: Cc1nnc(N(C)C)c2nn(-c3ccccc3OCC3CNCc4ccccc43)c(C)c12] | N,N,3,4-tetramethyl-2-(2-((1,2,3,4-tetrahydroisoquinolin-4-yl)methoxy)phenyl)-2H-pyrazolo[3,4-d]pyridazin-7-amine | 3.39 | 429.2 | A |
| 31 | 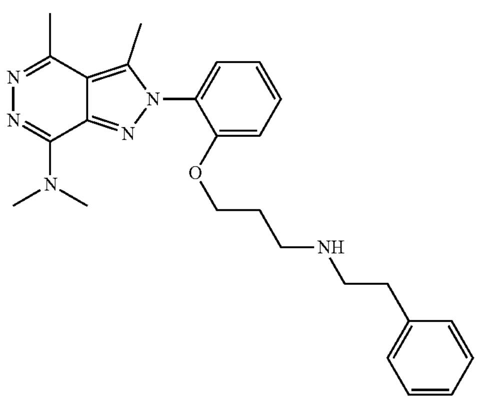 [SMILES: Cc1nnc(N(C)C)c2nn(-c3ccccc3OCCCNCCc3ccccc3)c(C)c12] | N,N,3,4-tetramethyl-2-(2-(3-(phenethylamino)propoxy)phenyl)-2H-pyrazolo[3,4-d]pyridazin-7-amine | 3.64 | 445.2 | A |
| 32 | 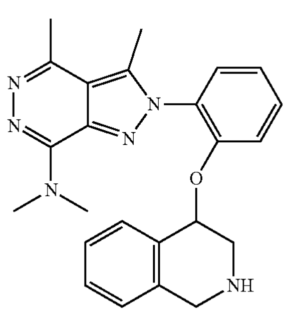 [SMILES: Cc1nnc(N(C)C)c2nn(-c3ccccc3OC3CNCc4ccccc43)c(C)c12] | N,N,3,4-tetramethyl-2-(2-((1,2,3,4-tetrahydroisoquinolin-4-yl)oxy)phenyl)-2H-pyrazolo[3,4-d]pyridazin-7-amine | 3.36 | 415.2 | A |

-continued

| EX | Structure | Chemical name | Ret time (min) | MS (M + H) | HPLC Method |
|---|---|---|---|---|---|
| 33 | 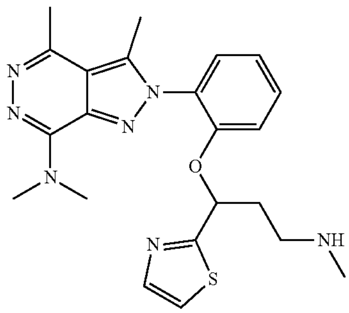 [SMILES: CNCCC(Oc1ccccc1-n1nc2c(N(C)C)nnc(C)c2c1C)c1nccs1] | N,N,3,4-tetramethyl-2-(2-(3-(methylamino)-1-(thiazol-2-yl)propoxy)phenyl)-2H-pyrazolo[3,4-d]pyridazin-7-amine | 2.91 | 438.2 | A |
| 34 | 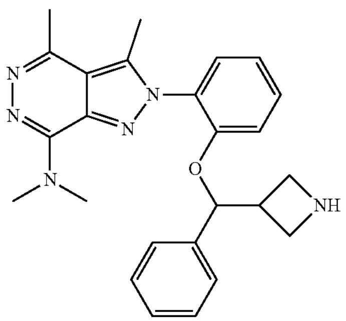 [SMILES: Cc1nnc(N(C)C)c2nn(-c3ccccc3OC(c3ccccc3)C3CNC3)c(C)c12] | 2-(2-(azetidin-3-yl(phenyl)methoxy)phenyl)-N,N,3,4-tetramethyl-2H-pyrazolo[3,4-d]pyridazin-7-amine | 3.14 | 429.2 | A |
| 35 | 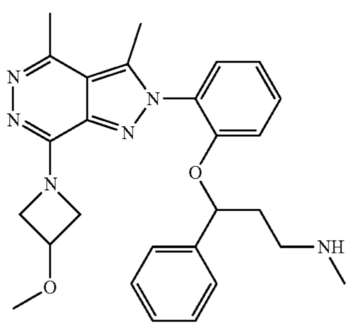 [SMILES: CNCCC(Oc1ccccc1-n1nc2c(N3CC(OC)C3)nnc(C)c2c1C)c1ccccc1] | 3-(2-(7-(3-methoxyazetidin-1-yl)-3,4-dimethyl-2H-pyrazolo[3,4-d]pyridazin-2-yl)phenoxy)-N-methyl-3-phenylpropan-1-amine | 3.29 | 473.2 | A |
| 36 | 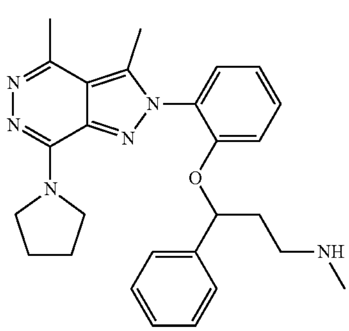 [SMILES: CNCCC(Oc1ccccc1-n1nc2c(N3CCCC3)nnc(C)c2c1C)c1ccccc1] | 3-(2-(3,4-dimethyl-7-(pyrrolidin-1-yl)-2H-pyrazolo[3,4-d]pyridazin-2-yl)phenoxy)-N-methyl-3-phenylpropan-1-amine | 3.54 | 457.2 | A |

-continued

| EX | Structure | Chemical name | Ret time (min) | MS (M + H) | HPLC Method |
|---|---|---|---|---|---|
| 37 | 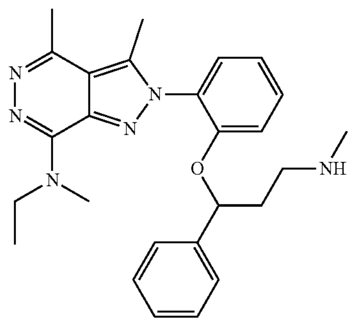 [SMILES: CCN(C)c1nnc(C)c2c(C)n(-c3ccccc3OC(CCNC)c3ccccc3)nc12] | N-ethyl-N,3,4-trimethyl-2-(2-(3-(methylamino)-1-phenylpropoxy)phenyl)-2H-pyrazolo[3,4-d]pyridazin-7-amine [2] | 3.58 | 445.2 | A |
| 38 | 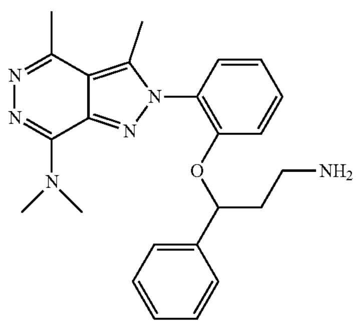 [SMILES: Cc1nnc(N(C)C)c2nn(-c3ccccc3OC(CCN)c3ccccc3)c(C)c12] | 2-(2-(3-amino-1-phenylpropoxy)phenyl)-N,N,3,4-tetramethyl-2H-pyrazolo[3,4-d]pyridazin-7-amine | 3.14 | 417.3 | A |
| 39 | 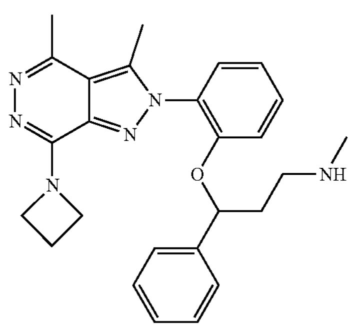 [SMILES: CNCCC(Oc1ccccc1-n1nc2c(N3CCC3)nnc(C)c2c1C)c1ccccc1] | 3-(2-(7-(azetidin-1-yl)-3,4-dimethyl-2H-pyrazolo[3,4-d]pyridazin-2-yl)phenoxy)-N-methyl-3-phenylpropan-1-amine | 3.15 | 443.2 | A |
| 40 | 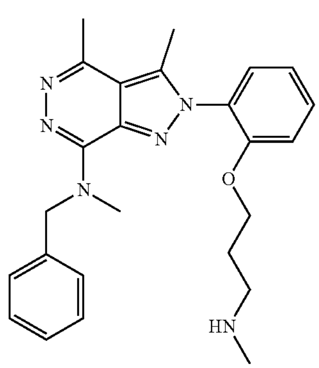 [SMILES: CNCCCOc1ccccc1-n1nc2c(N(C)Cc3ccccc3)nnc(C)c2c1C] | N-benzyl-N,3,4-trimethyl-2-(2-(3-(methylamino)propoxy)phenyl)-2H-pyrazolo[3,4-d]pyridazin-7-amine | 3.42 | 431.2 | A |

-continued

| EX | Structure | Chemical name | Ret time (min) | MS (M + H) | HPLC Method |
|---|---|---|---|---|---|
| 41 | 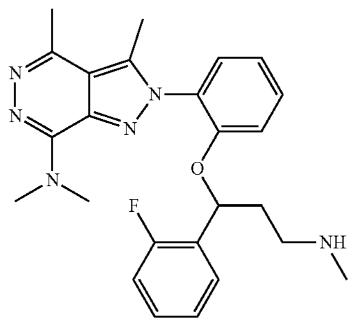 [SMILES: CNCCC(Oc1ccccc1-n1nc2c(N(C)C)nnc(C)c2c1C)c1ccccc1F] | 2-(2-(1-(2-fluorophenyl)-3-(methylamino)propoxy)phenyl)-N,N,3,4-tetramethyl-2H-pyrazolo[3,4-d]pyridazin-7-amine | 3.29 | 449.2 | A |
| 42 | 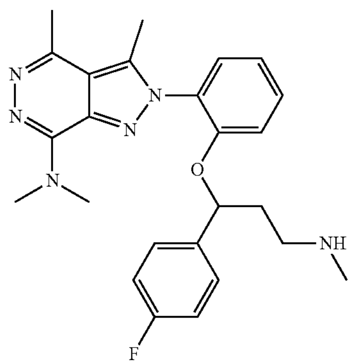 [SMILES: CNCCC(Oc1ccccc1-n1nc2c(N(C)C)nnc(C)c2c1C)c1ccc(F)cc1] | 2-(2-(1-(4-fluorophenyl)-3-(methylamino)propoxy)phenyl)-N,N,3,4-tetramethyl-2H-pyrazolo[3,4-d]pyridazin-7-amine | 3.35 | 449.2 | A |
| 43 | 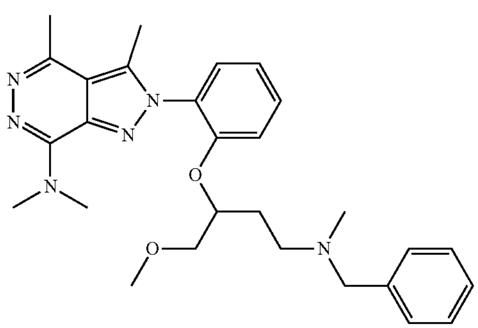 [SMILES: COCC(CCN(C)Cc1ccccc1)Oc1ccccc1-n1nc2c(N(C)C)nnc(C)c2c1C] | 2-(2-((4-(benzyl(methyl)amino)-1-methoxybutan-2-yl)oxy)phenyl)-N,N,3,4-tetramethyl-2H-pyrazolo[3,4-d]pyridazin-7-amine | 4.63 | 489.3 | A |
| 44 | 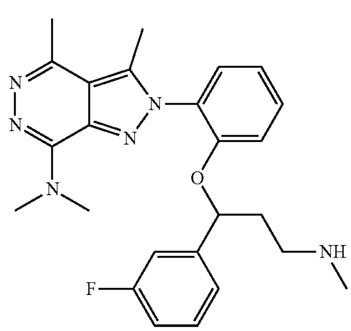 [SMILES: CNCCC(Oc1ccccc1-n1nc2c(N(C)C)nnc(C)c2c1C)c1cccc(F)c1] | 2-(2-(1-(3-fluorophenyl)-3-(methylamino)propoxy)phenyl)-N,N,3,4-tetramethyl-2H-pyrazolo[3,4-d]pyridazin-7-amine | 3.38 | 449.2 | A |

| EX | Structure | Chemical name | Ret time (min) | MS (M + H) | HPLC Method |
|---|---|---|---|---|---|
| 45 | 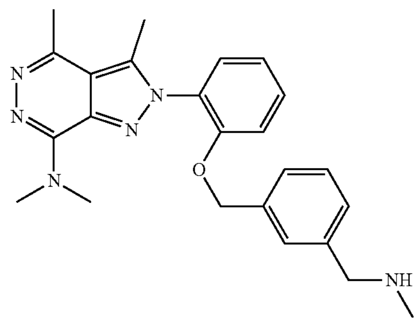 [SMILES: CNCc1cccc(COc2ccccc2-n2nc3c(N(C)C)nnc(C)c3c2C)c1] | N,N,3,4-tetramethyl-2-(2-((3-((methylamino)methyl)benzyl)oxy)phenyl)-2H-pyrazolo[3,4-d]pyridazin-7-amine | 3.19 | 417.2 | A |
| 46 | 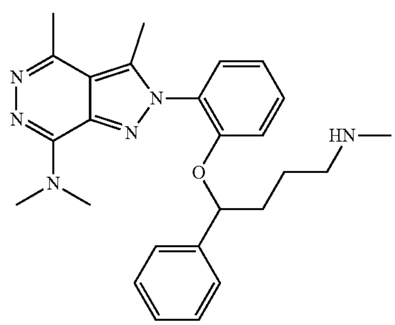 [SMILES: CNCCCC(Oc1ccccc1-n1nc2c(N(C)C)nnc(C)c2c1C)c1ccccc1] | N,N,3,4-tetramethyl-2-(2-(4-(methylamino)-1-phenylbutoxy)phenyl)-2H-pyrazolo[3,4-d]pyridazin-7-amine | 4.35 | 445.2 | B |
| 47 | 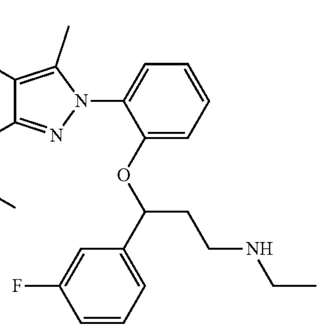 | 2-(2-(3-(ethylamino)-1-(3-fluorophenyl)propoxy)phenyl)-N,N,3,4-tetramethyl-2H-pyrazolo[3,4-d]pyridazin-7-amine | 3.74 | 463.3 | C |
| 48 | 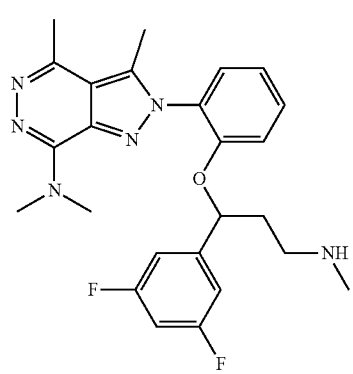 [SMILES: CNCCC(Oc1ccccc1-n1nc2c(N(C)C)nnc(C)c2c1C)c1cc(F)cc(F)c1] | 2-(2-(1-(3,5-difluorophenyl)-3-(methylamino)propoxy)phenyl)-N,N,3,4-tetramethyl-2H-pyrazolo[3,4-d]pyridazin-7-amine | 3.80 | 467.2 | C |

| EX | Structure | Chemical name | Ret time (min) | MS (M + H) | HPLC Method |
|---|---|---|---|---|---|
| 49 | 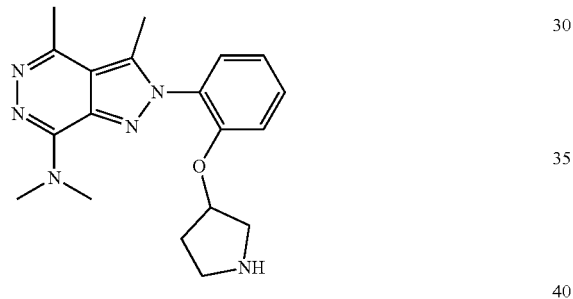 | N,N,3,4-tetramethyl-2-(2-((R)-((S)-morpholin-2-yl)(phenyl)methoxy)phenyl)-2H-pyrazolo[3,4-d]pyridazin-7-amine [3] | 3.69 | 459.2 | B |

[1] Step1 was skipped for commercial alkylating agents.
[2] Example 37 was prepared performing first demethylation ("Step3" in Example 1) followed by amine introduction ("Step2" in Example 1).
[3] Product was obtained as a pure diastereomer in racemic form (mixture with N,N,3,4-tetramethyl-2-(2-((S)-((R)-morpholin-2-yl)(phenyl)methoxy)phenyl)-2H-pyrazolo[3,4-d]pyridazin-7-amine)

Example 50

N,N,3,4-Tetramethyl-2-(2-(pyrrolidin-3-yloxy)phenyl)-2H-pyrazolo[3,4-d]pyridazin-7-amine A mixture of Example 8 (452 mg, 1 mmol) and Pd(OH)$_2$ (20% wt on carbon, 90 mg) in MeOH (16 mL) was stirred under 3 bars of H$_2$ for 48 h. The catalyst was filtered off, washing with MeOH, and the solvent was concentrated to dryness. The crude product was purified by flash chromatography, silica gel, gradient DCM to MeOH:DCM:NH$_3$ (1:4:0.15) to give the title compound (336 mg, 93% yield).
HPLC retention time (method A): 2.69 min; MS: 353.2 (M+H).
This method was used for the preparation of Example 51 using suitable starting materials:

| EX | Structure | Chemical name | Ret time (min) | MS (M + H) | HPLC Method |
|---|---|---|---|---|---|
| 51 | 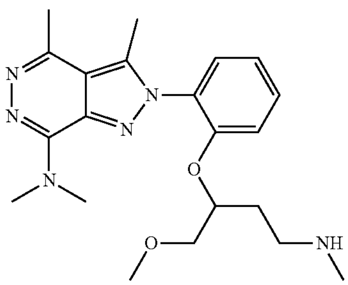 [SMILES: CNCCC(COC)Oc1ccccc1-n1nc2c(N(C)C)nnc(C)c2c1C] | 2-(2-((1-methoxy-4-(methylamino)butan-2-yl)oxy)phenyl)-N,N,3,4-tetramethyl-2H-pyrazolo[3,4-d]pyridazin-7-amine | 3.05 | 399.2 | A |

Example 52

2-(2-(3-(Dimethylamino)-1-phenylpropoxy)phenyl)-N,N,3,4-tetramethyl-2H-pyrazolo[3,4-d]pyridazin-7-amine

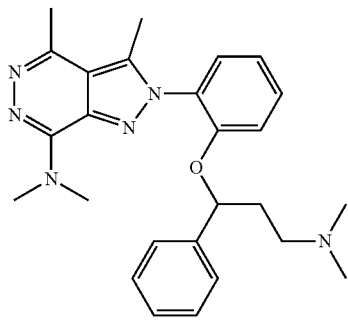 [SMILES: Cc1nnc(N(C)C)c2nn(-c3ccccc3OC(CCN(C)C)c3ccccc3)c(C)c12]

To a solution of Example 6 (15 mg, 0.034 mmol) in THF (3 mL), formaldehyde (37 wt % in water, 5.2 µL, 0.07 mmol) and acetic acid (4 µL, 0.07 mmol) were added. The reaction mixture was stirred at r.t. for 2.5 h and then sodium triacetoxyborohydride (18 mg, 0.08 mmol) was added. After stirring at r.t. overnight, water and EtOAc were added and the phases were separated. The aqueous layer was extracted with DCM. The combined organic phases were washed with brine, dried over MgSO$_4$ and concentrated under vacuum. The crude product was purified by flash chromatography, silica gel, gradient DCM to MeOH:DCM (1:4) to give the title compound (17 mg, quantitative yield).

HPLC retention time (method A): 3.88 min; MS: 445.2 (M+H).

This method was used for the preparation of examples 53-58 using suitable starting materials:

| EX | Structure | Chemical name | Ret time (min) | MS (M + H) | HPLC Method |
|----|-----------|---------------|----------------|------------|-------------|
| 53 | 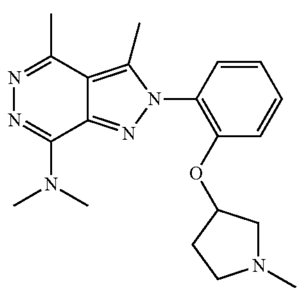 [SMILES: Cc1nnc(N(C)C)c2nn(-c3ccccc3OC3CCN(C)C3)c(C)c12] | N,N,3,4-tetramethyl-2-(2-((1-methylpyrrolidin-3-yl)oxy)phenyl)-2H-pyrazolo[3,4-d]pyridazin-7-amine | 3.10 | 367.2 | A |
| 54 | 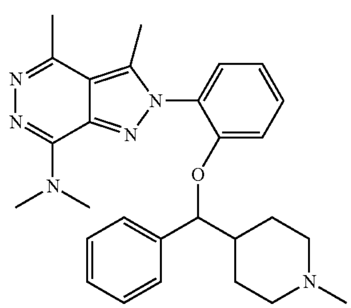 [SMILES: Cc1nnc(N(C)C)c2nn(-c3ccccc3OC(c3ccccc3)C3CCN(C)CC3)c(C)c12] | N,N,3,4-tetramethyl-2-(2-((1-methylpiperidin-4-yl)(phenyl)methoxy)phenyl)-2H-pyrazolo[3,4-d]pyridazin-7-amine | 3.71 | 471.3 | A |
| 55 | 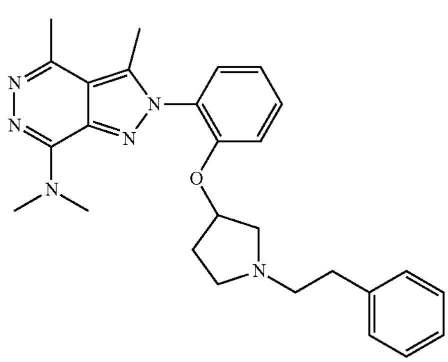 [SMILES: Cc1nnc(N(C)C)c2nn(-c3ccccc3OC3CCN(CCc4ccccc4)C3)c(C)c12] | N,N,3,4-tetramethyl-2-(2-((1-phenethylpyrrolidin-3-yl)oxy)phenyl)-2H-pyrazolo[3,4-d]pyridazin-7-amine | 4.29 | 457.2 | A |

| EX | Structure | Chemical name | Ret time (min) | MS (M+H) | HPLC Method |
|---|---|---|---|---|---|
| 56 | 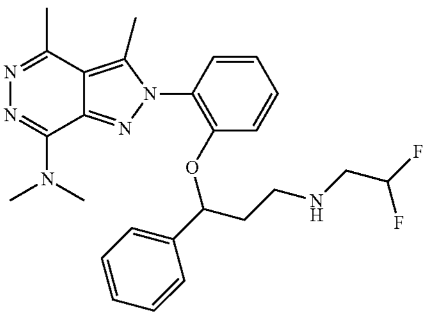 [SMILES: Cc1nnc(N(C)C)c2nn(-c3ccccc3OC(CCNCC(F)F)c3ccccc3)c(C)c12] | 2-(2-(3-((2,2-difluoroethyl)amino)-1-phenylpropoxy)phenyl)-N,N,3,4-tetramethyl-2H-pyrazolo[3,4-d]pyridazin-7-amine | 4.00 | 481.2 | B |
| 57 | 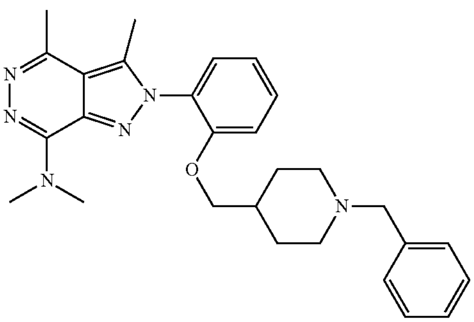 [SMILES: Cc1nnc(N(C)C)c2nn(-c3ccccc3OCC3CCN(Cc4ccccc4)CC3)c(C)c12] | 2-(2-((1-benzylpiperidin-4-yl)methoxy)phenyl)-N,N,3,4-tetramethyl-2H-pyrazolo[3,4-d]pyridazin-7-amine | 4.69 | 471.3 | C |
| 58 | 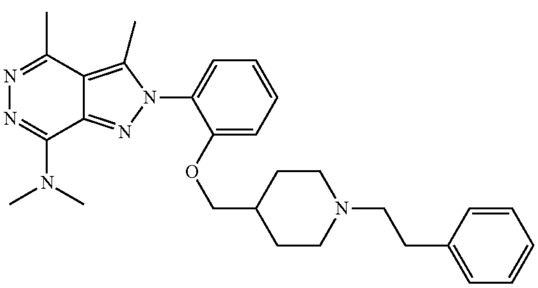 [SMILES: Cc1nnc(N(C)C)c2nn(-c3ccccc3OCC3CCN(CCc4ccccc4)CC3)c(C)c12] | N,N,3,4-tetramethyl-2-(2-((1-phenethylpiperidin-4-yl)methoxy)phenyl)-2H-pyrazolo[3,4-d]pyridazin-7-amine | 4.64 | 485.3 | C |

Example 59

2-((3,4-Dimethyl-2-(2-(3-(methylamino)-1-phenyl-propoxy)phenyl)-2H-pyrazolo[3,4-c]pyridazin-7-yl)(methyl)amino)ethanol

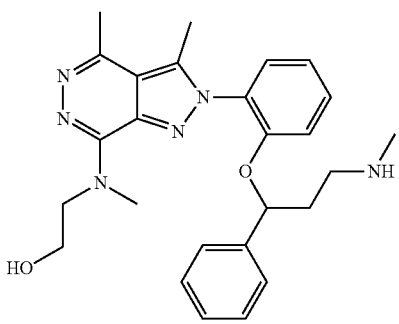

Step 1. tert-Butyl (3-(2-(7-chloro-3,4-dimethyl-2H-pyrazolo[3,4-d]pyridazin-2-yl)phenoxy)-3-phenylpropyl)(methyl)carbamate: A suspension of intermediate 4 (1.0 g, 3.6 mmol), K₂CO₃ (1.5 g, 10.9 mmol) and tert-butyl (3-chloro-3-phenylpropyl)(methyl)carbamate (prepared according to Step 1 of Example 1, using suitable starting materials) (1.3 g, 4.7 mmol) in DMF (10 mL) was heated in a sealed tube at 100° C. overnight. Water and EtOAc were added to the cooled reaction mixture and the phases were separated. The aqueous phase was extracted twice with EtOAc. The combined organic phases were washed with brine, dried over MgSO₄ and concentrated to dryness. The residue was purified by flash chromatography, silica gel, gradient DCM to MeOH:DCM (1:4) to give the title compound (1 g, 52% yield).

Step 2. tert-Butyl (3-(2-(7-((2-hydroxyethyl)(methyl)amino)-3,4-dimethyl-2H-pyrazolo[3,4-c]pyridazin-2-yl)phenoxy)-3-phenylpropyl)(methyl)carbamate: In a sealed tube, a mixture of the product obtained in step 1 (0.2 g, 0.38 mmol), TEA (0.106 mL, 0.77 mmol) and 2-(methylamino)ethanol (31 mg, 0.39 mmol) in IPA (2 mL) was heated at 120° C. overnight. Then, water was added, the pH was adjusted to 9 with 1 N NaOH and it was extracted with DCM. The combined organic phases were washed with brine, dried over MgSO₄ and concentrated to dryness. The crude product was purified by flash chromatography, silica gel, gradient DCM to MeOH:DCM (1:4) to give the title compound (64 mg, 30% yield).

Step 3. Title compound: Following the same procedure of Example 1 Step 5, and starting from the product obtained in Step 2, the title compound was obtained (17 mg, 33% yield).

HPLC retention time (method A): 3.06 min; MS: 461.2 (M+H).

This method was used for the preparation of examples 60-62 using suitable starting materials:

| EX | Structure | Chemical name | Ret time (min) | MS (M+H) | HPLC Method |
|---|---|---|---|---|---|
| 60 | 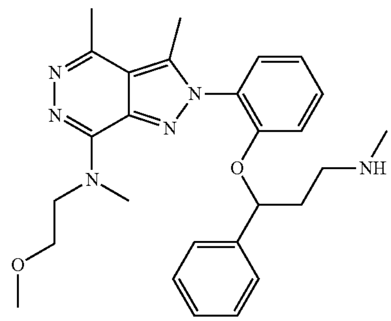 [SMILES: CNCCC(Oc1ccccc1-n1nc2c(N(C)CCOC)nnc(C)c2c1C)c1ccccc1] | N-(2-methoxyethyl)-N,3,4-trimethyl-2-(2-(3-(methylamino)-1-phenylpropoxy)phenyl)-2H-pyrazolo[3,4-d]pyridazin-7-amine | 3.33 | 475.3 | A |
| 61 | 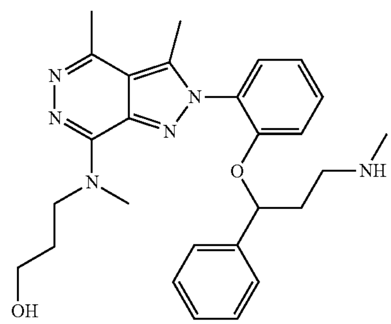 [SMILES: CNCCC(Oc1ccccc1-n1nc2c(N(C)CCCO)nnc(C)c2c1C)c1ccccc1] | 3-((3,4-dimethyl-2-(2-(3-(methylamino)-1-phenylpropoxy)phenyl)-2H-pyrazolo[3,4-d]pyridazin-7-yl)(methyl)amino)propan-1-ol | 3.15 | 475.2 | B |
| 62 | 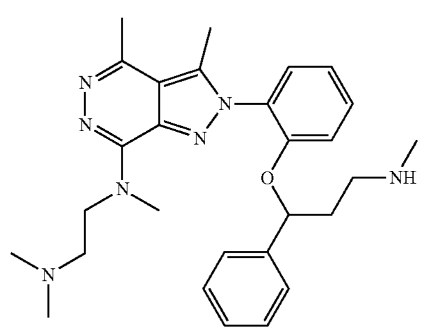 | N1-(3,4-dimethyl-2-(2-(3-(methylamino)-1-phenylpropoxy)phenyl)-2H-pyrazolo[3,4-d]pyridazin-7-yl)-N1,N2,N2-trimethylethane-1,2-diamine | 3.13 | 488.3 | B |

Example 63

2-(3,4-Dimethyl-2-(2-(3-(methylamino)-1-phenyl-propoxy)phenyl)-2H-pyrazolo[3,4-d]pyridazin-7-yl)acetonitrile

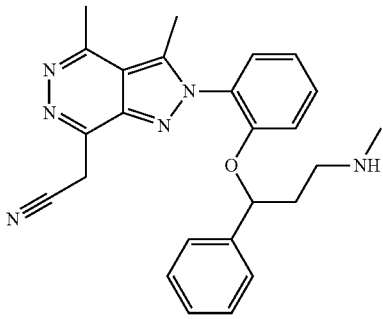

Step 1: tert-Butyl (3-(2-(7-(cyanomethyl)-3,4-dimethyl-2H-pyrazolo[3,4-d]pyridazin-2-yl)phenoxy)-3-phenylpropyl)(methyl)carbamate: To a solution of the product obtained in Step 1 of Example 59 (1.15 g, 2.22 mmol) in a mixture of anh. toluene (4.6 mL) and ACN (0.185 mL, 3.55 mmol) at 0° C., LiHMDS (1 M in THF, 7.1 mL, 7.1 mmol) was added dropwise. The reaction mixture was stirred at 0° C. for 1 h and then at r.t. overnight. NH₄Cl sat. solution was added and the mixture was extracted with EtOAc. The combined organic phases were dried over MgSO₄ and concentrated to dryness. The crude product was purified by flash chromatography, silica gel, gradient Cyclohexane/EtOAc 100:0 to Cyclohexane/EtOAc 0:100 to give the title compound (353 mg, 30% yield).

Step 2. Title compound: Following the same procedure of Example 1 Step 5, and starting from the product obtained in Step 1, the title compound was obtained (7.4 mg, 30% yield).

HPLC retention time (method A): 2.99 min; MS: 427.2 (M+H).

Example 64

3-(2-(3,4-Dimethyl-7-((5-methyl-1,2,4-oxadiazol-3-yl)methyl)-2H-pyrazolo[3,4-d]pyridazin-2-yl)phenoxy)-N-methyl-3-phenylpropan-1-amine

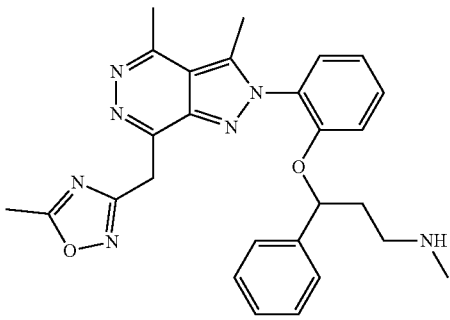

Step 1: tert-Butyl (3-(2-(7-(2-(hydroxyamino)-2-iminoethyl)-3,4-dimethyl-2H-pyrazolo[3,4-c]pyridazin-2-yl)phenoxy)-3-phenylpropyl)(methyl)carbamate: A solution of the product obtained in Step 1 of Example 63 (100 mg, 0.19 mmol), hydroxylamine hydrochloride (33 mg, 0.47 mmol) and Na₂CO₃ (50 mg, 0.47 mmol) in a mixture of EtOH (1 mL) and water (0.1 mL) was heated to reflux overnight. The solvent was concentrated and the residue was redissolved in DCM and water. The phases were separated and the aqueous phase was extracted with DCM. The combined organic phases were dried over MgSO₄ and concentrated to dryness to afford the title compound (95 mg, 90% yield).

Step 2. tert-Butyl (3-(2-(3,4-dimethyl-7-((5-methyl-1,2,4-oxadiazol-3-yl)methyl)-2H-pyrazolo[3,4-d]pyridazin-2-yl)phenoxy)-3-phenylpropyl)(methyl)carbamate: A solution of the product obtained in Step 1 (95 mg, 0.17 mmol) in acetic anhydride (0.9 mL, 9.5 mmol) was heated to reflux overnight. NaHCO₃ sat. solution and EtOAc were added, the aqueous phase was extracted with EtOAc and the combined organic phases were washed with water, brine, dried over MgSO₄ and concentrated. The crude was purified by flash chromatography, silica gel, gradient DCM to MeOH:DCM (1:4) to give the title compound (31 mg, 31% yield).

Step 3. Title compound: Following the same procedure of Example 1 Step 5, and starting from the product obtained in Step 2, the title compound was obtained (4.8 mg, 20% yield).

HPLC retention time (method A): 3.27 min; MS: 484.2 (M+H).

Example 65

N-Methyl-3-phenyl-3-(2-(1,4,5,7-tetramethyl-6H-pyrrolo[3,4-d]pyridazin-6-yl)phenoxy)propan-1-amine

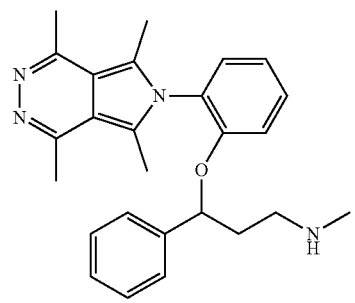 [SMILES: CNCCC(Oc1ccccc1-n1c(C)c2c(C)nnc(C)c2c1C)c1ccccc1]

Step 1. 1-(2-Methoxyphenyl)-2,5-dimethyl-1H-pyrrole: In a sealed tube, a mixture of 2-methoxyaniline (2.1 g, 17.05 mmol), hexane-2,5-dione (2 mL, 17.05 mmol) and AcOH (0.18 mL) in toluene (128 mL) was heated to reflux for 5 days. The solvent was evaporated to afford the title compound as a crude product (3.5 g, quant yield).

Step 2. 1,1'-(1-(2-Methoxyphenyl)-2,5-dimethyl-1H-pyrrole-3,4-diyl)diethanone: To a solution of the product obtained in Step 1 (0.3 g, 1.5 mmol) in toluene (4.5 mL), cooled to 0° C., a solution of SnCl₄ (0.17 mL, 1.5 mmol) in DCM (1.5 mL) was added dropwise followed by acetyl chloride (0.21 mL, 2.9 mmol). The reaction mixture was heated at 50° C. overnight. 1 N NaOH was added and it was extracted with EtOAc. The combined organic phases were washed with brine, dried over MgSO₄ and concentrated to dryness to afford the title compound (0.332 g, 78% yield).

Step 3. 6-(2-Methoxyphenyl)-1,4,5,7-tetramethyl-6H-pyrrolo[3,4-d]pyridazine: A solution of the product obtained in Step 2 (332 mg, 1.16 mmol), hydrazine (50-60% wt in water, 0.108 mL, 1.7 mmol) and a few drops of acetic acid in EtOH (4 mL) was stirred at r.t. overnight. The reaction mixture was poured onto crushed ice and it was extracted with DCM. The combined organic phases were dried over $MgSO_4$ and concentrated. The crude product was purified by flash chromatography, silica gel, gradient DCM to MeOH:DCM (1:4) to give the title compound (91 mg, 28% yield).

Step 4. 2-(1,4,5,7-Tetramethyl-6H-pyrrolo[3,4-d]pyridazin-6-yl)phenol: $BBr_3$ (1 M solution in DCM, 4.8 mL, 4.8 mmol) was added dropwise to a solution of the product obtained in Step 3 (91 mg, 0.323 mmol) in DCM (1.5 mL), cooled at −78° C., and the mixture was stirred at r.t overnight. Ice and 1 N NaOH were added to the reaction mixture to adjust the pH to 9. The suspension was filtered and the solid was dried under vacuum to obtain the title compound (63 mg, 73% yield)

Step 5. tert-Butyl methyl(3-phenyl-3-(2-(1,4,5,7-tetramethyl-6H-pyrrolo[3,4-d]pyridazin-6-yl)phenoxy)propyl)carbamate: Following the alkylation procedure described in Step 4 of Example 1, starting from the product obtained in Step 4 (63 mg, 0.235 mmol) and tert-butyl (3-chloro-3-phenylpropyl)(methyl)carbamate (73 mg, 0.259 mmol, prepared according to the procedure described in Step 1 of Example 1, using the corresponding starting material), the title compound was obtained (28 mg, 23% yield) after purification by flash chromatography, silica gel, gradient DCM to MeOH:DCM (1:4).

Step 6. Title compound: Following the same procedure of Example 1 Step 5, and starting from the product obtained in Step 5, the title compound was obtained (17 mg, 77% yield).

Example 66

3-(2-(3,4-Dimethyl-2H-pyrazolo[3,4-d]pyridazin-2-yl)phenoxy)-N-methyl-3-phenylpropan-1-amine

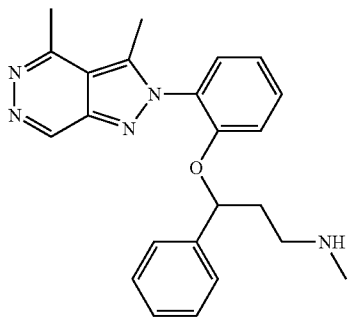 [SMILES: CNCCC(Oc1ccccc1-n1nc2cnnc(C)c2c1C)c1ccccc1]

Step 1. 2-(2-Methoxyphenyl)-3,4-dimethyl-2H-pyrazolo[3,4-c]pyridazine: A mixture of Intermediate 1 (200 mg, 0.96 mmol), TEA (0.145 mL, 1 mmol) and palladium (10% wt on carbon, 20 mg) in EtOAc (2 mL), was stirred under 1 bar of $H_2$ overnight. The catalyst was filtered off and fresh catalyst (20 mg) was added. The mixture was stirred under 1 bar of $H_2$ overnight. The catalyst was filtered off, the solid washed with EtOAc, and the filtrate was concentrated to dryness to give the title compound (273 mg, overweight, quantitative yield assumed) as a crude product that was used without purification.

Step 2. 2-(3,4-Dimethyl-2H-pyrazolo[3,4-d]pyridazin-2-yl)phenol. Following the experimental procedure described in Step 3 of Example 1, starting from the product obtained in Step 1 (273 mg, 64 wt %, 3.4 mmol), the title compound was obtained (104 mg, 63% yield).

Step 3. tert-Butyl (3-(2-(3,4-dimethyl-2H-pyrazolo[3,4-]pyridazin-2-yl)phenoxy)-3-phenylpropyl)(methyl)carbamate: Following the experimental procedure described in Step 4 of Example 1, starting from the product obtained in step 2 (104 mg, 0.43 mmol) and tert-butyl (3-chloro-3-phenylpropyl)(methyl)carbamate (prepared according to Step 1 of Example 1, using suitable starting materials) (1.3 g, 4.7 mmol), the title compound was obtained (156 mg, 65% yield).

Step 4. Title compound: Following the experimental procedure described in Step 5 of Example 1 starting from the product obtained in Step 3 (156 mg, 0.32 mmol), the title compound was obtained (93 mg, 76% yield).

HPLC retention time (method A): 3.06 min; MS: 388.2 (M+H).

Example 67

N,N,3,4-Tetramethyl-2-(2-(2-(methylamino)-1-phenylethoxy)phenyl)-2H-pyrazolo[3,4-d]pyridazin-7-amine

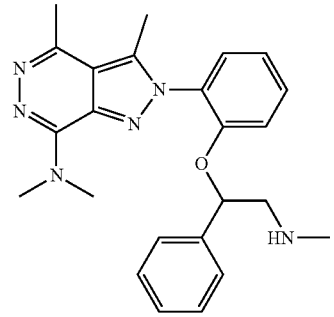

Step 1. Methyl 2-(2-(7-(dimethylamino)-3,4-dimethyl-2H-pyrazolo[3,4-d]pyridazin-2-yl)phenoxy)-2-phenylacetate: Following the experimental procedure described in Step 4 of Example 1, starting from the product obtained in Step 3 of Example 1 (250 mg, 0.88 mmol) and methyl 2-chloro-2-phenylacetate (117 mg, 0.63 mmol), the title compound was obtained (98 mg, 43% yield).

Step 2. 2-(2-(7-(Dimethylamino)-3,4-dimethyl-2H-pyrazolo[3,4-d]pyridazin-2-yl)phenoxy)-N-methyl-2-phenylacetamide: In a sealed tube, the product obtained in Step 1 (98 mg, 0.23 mmol) and methylamine (33 wt % in EtOH, 0.56 mL, 4.54 mmol) were heated at 90° C. overnight. The solvent was concentrated to obtain the title compound as a crude product (114 mg, overweight, quantitative yield assumed) which was used without further purification.

Step 3. Title compound: To a solution of the product obtained in Step 2 (114 mg, 85 wt %, 0.23 mmol) in anh THF (0.8 mL), under a $N_2$ atmosphere, borane dimethylsulfide complex (136 μL, 1.4 mmol) was added dropwise. The reaction mixture was heated at 55° C. overnight. Then, MeOH was added and the volatiles were removed under vacuum. The residue was redissolved in MeOH and $N^1,N^2$-dimethylethane-1,2-diamine (0.122 mL, 1.13 mmol) was added. The mixture was heated to reflux overnight. The solvent was concentrated and the crude product thus obtained was purified by flash chromatography, silica gel, gradient DCM to MeOH:DCM:NH$_3$ (1:4:0.15) to give the title compound (8.5 mg, 9% yield). HPLC retention time (method A): 3.50 min; MS: 417.2 (M+H).

Example 68

N,3,4-Trimethyl-2-(2-(3-(methylamino)-1-phenyl-propoxy)phenyl)-2H-pyrazolo[3,4-d]pyridazin-7-amine

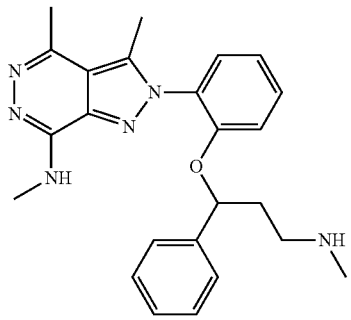 [SMILES: CNCCC(Oc1ccccc1-n1nc2c(NC)nnc(C)c2c1C)c1ccccc1]

Step 1. N-Benzyl-2-(2-methoxyphenyl)-N,3,4-trimethyl-2H-pyrazolo[3,4-d]pyridazin-7-amine: Following the experimental procedure described for the preparation of Step 2 of Example 1, starting from Intermediate 1 and N-benzylmethylamine, the title compound was obtained (453 mg, 70% yield).

Step 2. 2-(3,4-Dimethyl-7-(methylamino)-2H-pyrazolo[3,4-d]pyridazin-2-yl)phenol: To a solution of the product obtained in Step 1 (453 mg, 1.2 mmol) in DCM (7 mL), cooled at −78° C., BBr$_3$ (1 M solution in DCM, 6.2 mL, 6.2 mmol) was added dropwise. The reaction was allowed to reach −30° C. and stirred at that temperature until consumption of stating material. Then, crushed ice and 6 N NaOH were added to adjust the pH to 9. The volatiles were removed under vacuum and the precipitated solids were collected by filtration, washed with water and dried under vacuum to obtain the title compound (294 mg, 91% yield).

Step 3. tert-Butyl (3-(2-(3,4-dimethyl-7-(methylamino)-2H-pyrazolo[3,4-d]pyridazin-2-yl)phenoxy)-3-phenylpropyl)(methyl)carbamate: Following the procedure described for the preparation of Step 4 of Example 1 (100 mg, 0.37 mmol), starting from the product obtained in Step 2 and tert-butyl (3-chloro-3-phenylpropyl)(methyl)carbamate (prepared according to Step 1 of Example 1, using suitable starting materials), the title compound was obtained (177 mg, 70% yield).

Step 4. Title compound: Following the same procedure of Example 1 Step 5 starting from the product obtained in Step 3, the title compound was obtained (35 mg, 62% yield) HPLC retention time (method A): 3.06 min; MS: 417.2 (M+H).

The demethylation, alkylation and deprotection procedures described in Steps 2 to 4 of Example 68 were used in the preparation of Examples 69-71, using suitable starting materials:

| EX | Structure | Chemical name | Ret time (min) | MS (M + H) | HPLC Method |
|---|---|---|---|---|---|
| 69 | 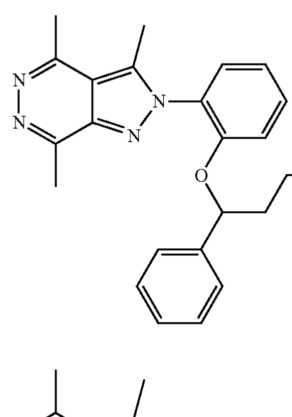 | N-methyl-3-phenyl-3-(2-(3,4,7-trimethyl-2H-pyrazolo[3,4-d]pyridazin-2-yl)phenoxy)propan-1-amine | 3.00 | 402.2 | A |
| 70 | 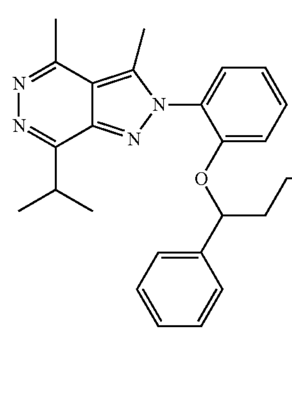 | 3-(2-(7-isopropyl-3,4-dimethyl-2H-pyrazolo[3,4-d]pyridazin-2-yl)phenoxy)-N-methyl-3-phenylpropan-1-amine | 3.42 | 430.2 | A |

| EX | Structure | Chemical name | Ret time (min) | MS (M+H) | HPLC Method |
|---|---|---|---|---|---|
| 71 | 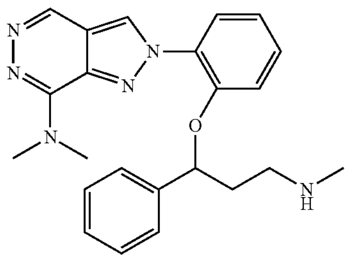 [SMILES: CNCCC(Oc1ccccc1-n1cc2cnnc(N(C)C)c2n1)c1ccccc1] | N,N-dimethyl-2-(2-(3-(methylamino)-1-phenylpropoxy)phenyl)-2H-pyrazolo[3,4-d]pyridazin-7-amine | 3.45 | 403.2 | B |

Example 72

N,N,3,4-Tetramethyl-2-(2-((2-((methylamino)methyl)benzyl)oxy)phenyl)-2H-pyrazolo[3,4-d]pyridazin-7-amine

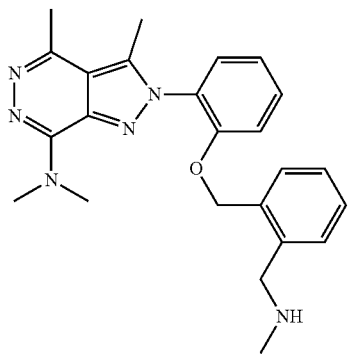 [SMILES: CNCc1ccccc1COc1ccccc1-n1nc2c(N(C)C)nnc(C)c2c1C]

Step 1. (2-((2-(7-(Dimethylamino)-3,4-dimethyl-2H-pyrazolo[3,4-d]pyridazin-2-yl)phenoxy)methyl)phenyl)methanol: In a sealed tube, a mixture of the product obtained in Step 3 of Example 1 (200 mg, 0.7 mmol), $K_2CO_3$ (292 mg, 2.1 mmol) and (3-(bromomethyl)phenyl)methanol (185 mg, 0.92 mmol) in DMF (2 mL) was heated at 100° C. overnight. EtOAc and water were added, the phases were separated and the aqueous layer was extracted with EtOAc. The combined organic phases were washed with brine, dried over $MgSO_4$ and concentrated to dryness. The crude product was purified by flash chromatography, silica gel, gradient DCM to MeOH:DCM (1:4) to give the title compound (133 mg, 47% yield).

Step 2. 2-((2-(7-(Dimethylamino)-3,4-dimethyl-2H-pyrazolo[3,4-d]pyridazin-2-yl)phenoxy)methyl)benzaldehyde: To a solution of the product obtained in Step 1 (133 mg, 0.33 mmol) in DCM, Dess-Martin periodinane (167 mg, 0.39 mmol) was added and the reaction mixture was stirred at r.t. for 2 h. DCM was added and the organic phase was washed with 1 M NaOH and brine, dried over $MgSO_4$ and concentrated to dryness to afford the title compound (107 mg, 81% yield) which was used in the next step without further purification.

Step 3. Title compound: To a solution of the product obtained in Step 2 (107 mg, 0.26 mmol) and a few drops of acetic acid in 1,2-dichloroethane (1.5 mL), sodium triacetoxyborohydride (90 mg, 0.43 mmol) was added and the reaction mixture was stirred at r.t. overnight. DCM was added and the organic phase was washed with 1 M NaOH and brine, dried over $MgSO_4$ and concentrated to dryness. The crude product was purified by flash chromatography, silica gel, gradient DCM to MeOH:DCM (1:4) to give the title compound (17 mg, 15% yield).

HPLC retention time (method A): 3.21 min; MS: 417.2 (M+H).

Example 73

2-(2-(3-((2-Fluoroethyl)amino)-1-phenylpropoxy)phenyl)-N,N,3,4-tetramethyl-2H-pyrazolo[3,4-d]pyridazin-7-amine

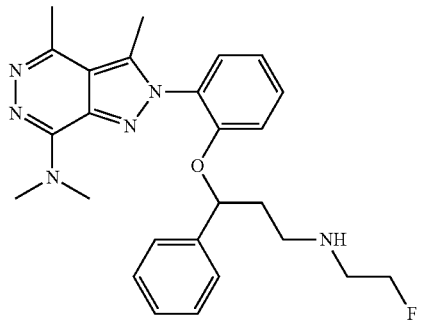 [SMILES: Cc1nnc(N(C)C)c2nn(-c3ccccc3OC(CCNCCF)c3ccccc3)c(C)c12]

Step 1. tert-Butyl (3-(2-(7-(dimethylamino)-3,4-dimethyl-2H-pyrazolo[3,4-d]pyridazin-2-yl)phenoxy)-3-phenylpropyl)(2-fluoroethyl)carbamate: To a solution of Boc-protected Example 38 (0.2 g, 0.38 mmol) in DMF (2 mL), cooled at 0° C., NaH (60 wt % in mineral oil, 31 mg, 0.77 mmol) was added and the reaction mixture was stirred at 0° C. for 30 min and then 1-fluoro-2-iodoethane (32 µL, 0.38 mmol) was added. The reaction mixture was stirred at r.t overnight. It was cooled at 0° C., water and brine were added and it was extracted with DCM. The combined organic phases were dried over $MgSO_4$ and concentrated to dryness. The crude product was purified by flash chromatography, silica gel, gradient DCM to MeOH: DCM (1:4) to give the title compound (19 mg, 10% yield)

Step 2. Title compound: Following the same procedure of Example 1 Step 5 starting from the product obtained in Step 1, the title compound was obtained (4 mg, 26% yield).

HPLC retention time (method B): 3.92 min; MS: 463.2 (M+H).

Example 74

2-(2-((1-(Benzyl(methyl)amino)-3-phenylpropan-2-yl)oxy)phenyl)-N,N,3,4-tetramethyl-2H-pyrazolo[3,4-d]pyridazin-7-amine

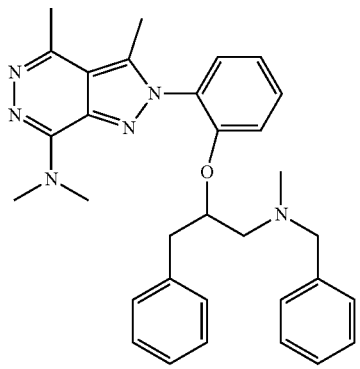 [SMILES: Cc1nnc(N(C)C)c2nn(-c3ccccc3OC(Cc3ccccc3)CN(C)Cc3ccccc3)c(C)c12]

Step 1. N-Benzyl-N-methyl-2-(2-nitrophenoxy)-3-phenylpropan-1-amine: To a solution of 1-(benzyl(methyl)amino)-3-phenylpropan-2-ol (0.4 g, 1.58 mmol) in DMA (4 mL), NaH (60 wt % in mineral oil, 0.19 mg, 4.7 mmol) was added and the reaction mixture was stirred at r.t for 30 min. Then, 1-fluoro-2-nitrobenzene (0.17 mL, 1.58 mmol) was added and the reaction mixture was heated at 50° C. for 3 h. Water was added and it was extracted with EtOAc. The combined organic phases were washed with brine, dried over MgSO$_4$ and concentrated. The crude product was purified by flash chromatography, silica gel, gradient Cyclohexane/EtOAc 100:0 to Cyclohexane/EtOAc 0:100 to give the title compound (0.5 g, 84% yield).

Step 2. 2-((1-(Benzyl(methyl)amino)-3-phenylpropan-2-yl)oxy)aniline: To a solution of the product obtained in Step 1 (0.5 g, 1.33 mmol) in MeOH (5 mL), SnCl$_2$ (1 g, 5.3 mmol) was added. The mixture was heated to reflux for 3 h. Then, it was poured into water and pH was adjusted to 9 with Na$_2$CO$_3$, sat. solution. It was extracted with DCM and the combined organic phases were washed with water and brine, dried over MgSO$_4$ and concentrated to dryness to afford the title compound (368 mg, 80% yield).

Step 3. (Z)-Ethyl 2-(2-(2-((1-(benzyl(methyl)amino)-3-phenylpropan-2-yl)oxy)phenyl)hydrazono)-2-chloroacetate: Following the experimental procedure described in Step 1 of Intermediate 1, starting from the compound obtained in Step 2 (368 mg, 1.06 mmol) the title compound was obtained (336 mg, 66% yield).

Step 4. Ethyl 4-acetyl-1-(2-((1-(benzyl(methyl)amino)-3-phenylpropan-2-yl)oxy)phenyl)-5-methyl-1H-pyrazole-3-carboxylate: Following the experimental procedure described in Step 2 of Intermediate 1, starting from the product obtained in Step 3, the title compound was obtained (239 mg, 65% yield).

Step 5. 2-(2-((1-(Benzyl(methyl)amino)-3-phenylpropan-2-yl)oxy)phenyl)-3,4-dimethyl-2H-pyrazolo[3,4-d]pyridazin-7(6H)-one: Following the experimental procedure described in Step 3 of Intermediate 1, starting from the product obtained in Step 4 (337 mg, 0.64 mmol) the title compound was obtained (151 mg, 48% yield).

Step 6. N-Benzyl-2-(2-(7-chloro-3,4-dimethyl-2H-pyrazolo[3,4-d]pyridazin-2-yl)phenoxy)-N-methyl-3-phenylpropan-1-amine: Following the procedure described in Step 4 of Intermediate 1, starting from the product obtained in Step 5 (151 mg, 0.3 mmol), the title compound was obtained (203 mg, overweight, quant yield assumed).

Step 7. Title compound: Following the procedure described in Step 2 of Example 1, starting from the product obtained in Step 6 (203 mg, 77 wt %, 0.3 mmol), the title compound was obtained after purification by flash chromatography, silica gel, gradient DCM to MeOH:DCM (1:4) (103 mg, 64% yield).

HPLC retention time (method A): 5.33 min; MS: 521.3 (M+H).

This method was used for the preparation of Example 75 using suitable starting materials:

| EX | Structure | Chemical name | Ret time (min) | MS (M+H) | HPLC Method |
|---|---|---|---|---|---|
| 75 | 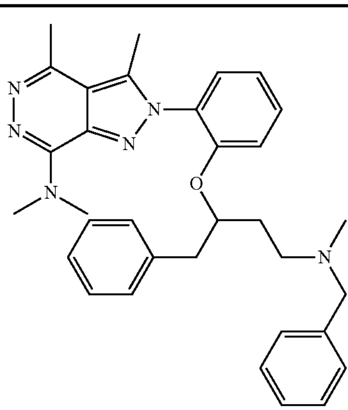 | 2-(2-((4-(benzyl(methyl)amino)-1-phenylbutan-2-yl)oxy)phenyl)-N,N,3,4-tetramethyl-2H-pyrazolo[3,4-d]pyridazin-7-amine | 5.22 | 535.3 | A |

Example 76

N,N,3,4-Tetramethyl-2-(2-((1-(methylamino)-3-phenylpropan-2-yl)oxy)phenyl)-2H-pyrazolo[3,4-d]pyridazin-7-amine

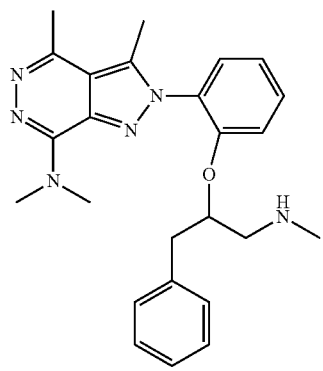 [SMILES: CNCC(Cc1ccccc1)Oc1ccccc1-n1nc2c(N(C)C)nnc(C)c2c1C]

A mixture of Example 74 (103 mg, 0.39 mmol), Pd(OH)$_2$ (20% wt on carbon, 21 mg) and acetic acid (22 µL, 0.39 mmol) in MeOH (3 mL) was stirred under 3 bars of H$_2$ overnight. The catalyst was filtered off and the solvent was concentrated to dryness. The crude product was purified by flash chromatography, silica gel, gradient DCM to MeOH:DCM (1:4) to give the title compound (69 mg, 81% yield).

HPLC retention time (method A): 3.67 min; MS: 431.2 (M+H).

This method was used for the preparation of Example 77 from Example 75:

Example 78

N,N,3,4-Tetramethyl-2-(2-(3-(methylamino)-1-(thiophen-2-yl)propoxy)phenyl)-2H-pyrazolo[3,4-d]pyridazin-7-amine

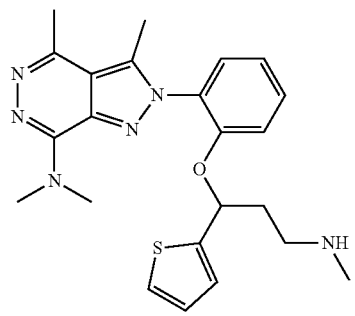 [SMILES: CNCCC(Oc1ccccc1-n1nc2c(N(C)C)nnc(C)c2c1C)c1cccs1]

Step 1. 2-(1,3-dichloropropyl)thiophene: TEA (1.43 mL, 10.3 mmol) and methanesulfonyl chloride (0.62 mL, 8.0 mmol) were slowly added to a solution of 3-chloro-1-(thiophen-2-yl)propan-1-ol (1.01 g, 5.72 mmol) in DCM (34 mL), previously cooled at 0-5° C. and the mixture was stirred at this temperature overnight. Sat. NaHCO$_3$ was added and the phases were separated. The aqueous phase was back extracted twice with DCM. The combined organic phases were washed with brine, dried over MgSO$_4$ and concentrated to dryness to afford the title compound (1.16 g, quant yield) as a crude product that was used without further purification.

Step 2. 2-(2-(3-Chloro-1-(thiophen-2-yl)propoxy)phenyl)-N,N,3,4-tetramethyl-2H-pyrazolo[3,4-d]pyridazin-7-amine: The product was prepared following the alkylation procedure described in Step 4 of Example 1, starting from the product obtained in Step 3 of Example 1 (0.25 g, 0.88 mmol) and the alkylating agent obtained in Step 1 (0.207 g, 1.06 mmol). After purification by flash chromatography (silica gel, gradient DCM to MeOH:DCM (1:4)), the title compound was obtained (32 mg, 8% yield).

Step 3. Title compound: In a sealed tube, a mixture of the product obtained in Step 2 (32 mg, 0.072 mmol) and methylamine (40 wt % in water, 5 mL) was heated at 50°

| EX | Structure | Chemical name | Ret time (min) | MS (M + H) | HPLC Method |
|---|---|---|---|---|---|
| 77 | 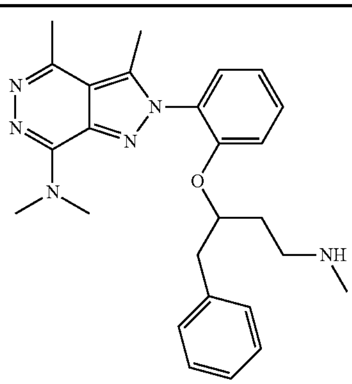 | N,N,3,4-tetramethyl-2-(2-((4-(methylamino)-1-phenylbutan-2-yl)oxy)phenyl)-2H-pyrazolo[3,4-d]pyridazin-7-amine | 3.44 | 445.2 | A |

C. overnight. The solvent was concentrated and the crude product was purified by flash chromatography, $C_{18}$, gradient $NH_4HCO_3$ pH 8 to ACN to give the title compound (1.3 mg, 4% yield).

HPLC retention time (method A): 3.28 min; MS: 437.2 (M+H).

Example 79

3-(1-(2-(7-(Dimethylamino)-3,4-dimethyl-2H-pyrazolo[3,4-d]pyridazin-2-yl)phenoxy)-3-(methylamino)propyl)phenol

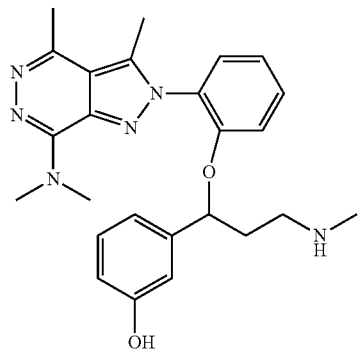 [SMILES: CNCCC(Oc1ccccc1-n1nc2c(N(C)C)nnc(C)c2c1C)c1cccc(O)c1]

Step 1. tert-Butyl (3-(2-(7-(dimethylamino)-3,4-dimethyl-2H-pyrazolo[3,4-d]pyridazin-2-yl)phenoxy)-3-(3-iodophenyl)propyl)(methyl)carbamate: Prepared following the procedure described in Steps 1-4 of Example 1, using suitable starting materials.

Step 2. tert-Butyl (3-(2-(7-(dimethylamino)-3,4-dimethyl-2H-pyrazolo[3,4-d]pyridazin-2-yl)phenoxy)-3-(3-hydroxyphenyl)propyl)(methyl)carbamate: In a sealed tube, a mixture of the product obtained in Step 1 (50 mg, 0.076 mmol), tetrabutylammonium hydroxide (1 mL, 0.23 mmol), quinolinol (2.2 mg, 0.015 mmol) and CuI (1.5 mg, 0.0076 mmol) in anh DMSO (0.1 mL) was heated at 130° C. overnight. A solution of 0.5 M HCl was added and it was extracted with EtOAc. The combined organic phases were dried over $MgSO_4$ and concentrated. The crude product was purified by flash chromatography, silica gel, gradient DCM to MeOH:DCM (1:4) to give the title compound (19 mg, 46% yield).

Step 3. Title compound: A solution of the product obtained in Step 2 (19 mg, 0.035 mmol) and HCl (1.25M in EtOH, 0.56 mL, 0.7 mmol) was stirred at r.t until full conversion. The solvent was concentrated, and the crude product was purified by eluting through an SCX cartridge and then by flash chromatography, silica gel, gradient DCM to MeOH:DCM:$NH_3$ (1:4:0.15) to give the title compound (8 mg, 53% yield).

HPLC retention time (method A): 2.93 min; MS: 447.2 (M+H).

Example 80

1-(4-(7-(Dimethylamino)-3,4-dimethyl-2H-pyrazolo[3,4-d]pyridazin-2-yl)-3-(3-(methylamino)-1-phenylpropoxy)phenyl)pyrrolidin-2-one

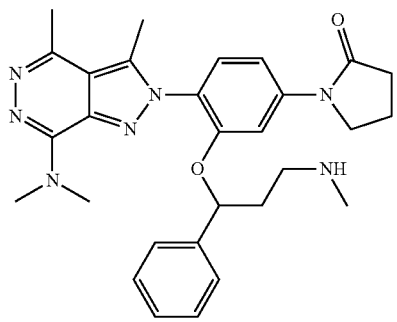 [SMILES: CNCCC(Oc1cc(N2CCCC2=O)ccc1-n1nc2c(N(C)C)nnc(C)c2c1C)c1ccccc1]

Step 1. tert-Butyl (3-(2-(7-(dimethylamino)-3,4-dimethyl-2H-pyrazolo[3,4-d]pyridazin-2-yl)-5-(2-oxopyrrolidin-1-yl)phenoxy)-3-phenylpropyl)(methyl) carbamate: Pyrrolidin-2-one (25 mg, 0.29 mmol), $Cs_2CO_3$ (112 mg, 0.34 mmol), $Pd_2(dba)_3$ (2.2 mg, 2.4·10$^{-3}$ mmol) and XantPhos (4.2 mg, 7.4·10$^{-3}$ mmol) were added, under argon, to a solution of Boc-protected Example 25 (150 mg, 0.25 mmol) in dioxane (1 mL). The mixture was heated at 100° C. overnight under argon. Then, it was cooled and the reaction mixture was filtered through a pad of Celite, washing with EtOAc. The filtrate was evaporated to dryness and the crude product was purified by flash chromatography, silica gel, gradient DCM to MeOH:DCM (1:4) to give the title compound (143 mg, 95% yield).

Step 2. Title compound: Using the same procedure of Example 1 Step 5 starting from the product obtained in Step 1 the title compound was obtained (58 mg, 48% yield).

HPLC retention time (method A): 3.16 min; MS: 514.3 (M+H).

This method was used for the preparation of examples 81-84 using suitable starting materials:

| Ex | Structure | Chemical name | Ret time (min) | MS (M + H) | HPLC Method |
|---|---|---|---|---|---|
| 81 | 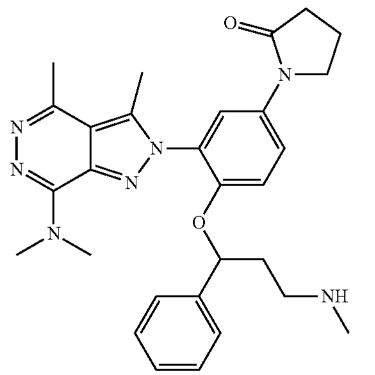 [SMILES: CNCCC(Oc1ccc(N2CCCC2=O)cc1-n1nc2c(N(C)C)nnc(C)c2c1C)c1ccccc1] | 1-(3-(7-(dimethylamino)-3,4-dimethyl-2H-pyrazolo[3,4-d]pyridazin-2-yl)-4-(3-(methylamino)-1-phenylpropoxy)phenyl)pyrrolidin-2-one | 3.07 | 514.3 | A |
| 82 | 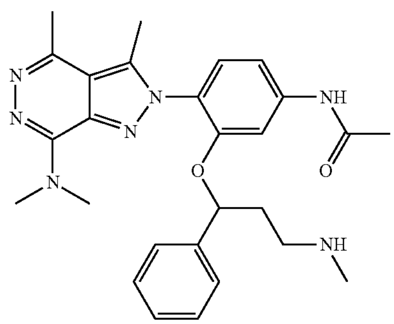 [SMILES: CNCCC(Oc1cc(NC(C)=O)ccc1-n1nc2c(N(C)C)nnc(C)c2c1C)c1ccccc1] | N-(4-(7-(dimethylamino)-3,4-dimethyl-2H-pyrazolo[3,4-d]pyridazin-2-yl)-3-(3-(methylamino)-1-phenylpropoxy)phenyl)acetamide | 2.84 | 488.3 | A |
| 83 | 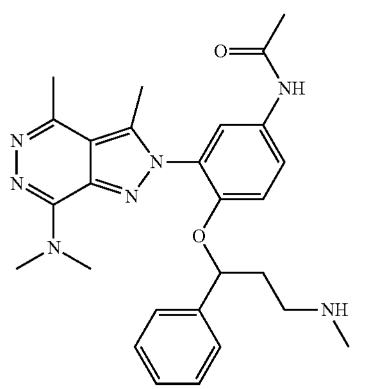 [SMILES: CNCCC(Oc1ccc(NC(C)=O)cc1-n1nc2c(N(C)C)nnc(C)c2c1C)c1ccccc1] | N-(3-(7-(dimethylamino)-3,4-dimethyl-2H-pyrazolo[3,4-d]pyridazin-2-yl)-4-(3-(methylamino)-1-phenylpropoxy)phenyl)acetamide | 2.74 | 488.3 | A |
| 84 | 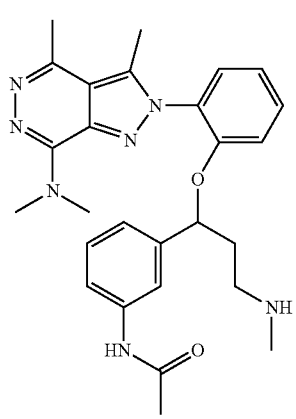 [SMILES: CNCCC(Oc1ccccc1-n1nc2c(N(C)C)nnc(C)c2c1C)c1cccc(NC(C)=O)c1] | N-(3-(1-(2-(7-(dimethylamino)-3,4-dimethyl-2H-pyrazolo[3,4-d]pyridazin-2-yl)phenoxy)-3-(methylamino)propyl)phenyl)acetamide | 2.88 | 488.3 | A |

Example 85

4-(7-(Dimethylamino)-3,4-dimethyl-2H-pyrazolo[3,4-c]pyridazin-2-yl)-3-(3-(methylamino)-1-phenyl-propoxy)benzonitrile

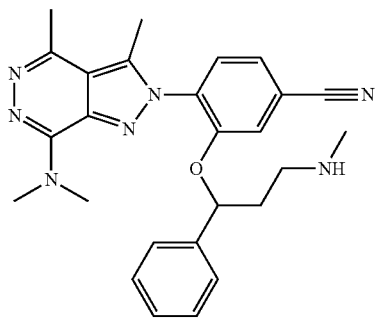 [SMILES: CNCCC(Oc1cc(C#N)ccc1-n1nc2c(N(C)C)nnc(C)c2c1C)c1ccccc1]

Step 1. tert-Butyl (3-(5-cyano-2-(7-(dimethylamino)-3,4-dimethyl-2H-pyrazolo[3,4-d]pyridazin-2-yl)phenoxy)-3-phenylpropyl)(methyl)carbamate: To a solution of Boc-protected Example 25 (0.5 g, 0.82 mmol) in a mixture of DMF (1 mL) and H$_2$O (1 µL), 1,1'-bis(diphenylphosphino)ferrocene (2.6 mg, 4.8·10$^{-3}$ mmol), Pd$_2$(dba)$_3$ (2 mg, 1.6·10$^{-3}$ mmol), Zn(CN)$_2$ (52 mg, 0.44 mmol) and Zn (4.2 mg, 0.066 mmol) were added under argon. The mixture was stirred at 100° C. overnight. Then, the suspension was filtered through a pad of Celite, washing with EtOAc. The filtrate was concentrated to dryness and the crude product was purified by flash chromatography, silica gel, gradient DCM to MeOH:DCM (1:4) to give the title compound (265 mg, 58% yield).

Step 2. Title compound: Using the same procedure of Example 1 Step 5 starting from the product obtained in Step 1 the title compound was obtained (24 mg, 63% yield).

HPLC retention time (method A): 3.33 min; MS: 456.2 (M+H).

This method was used for the preparation of example 86 using suitable starting materials:

Example 87

2-(4-Ethoxy-2-(3-(methylamino)-1-phenylpropoxy)phenyl)-N,N,3,4-tetramethyl-2H-pyrazolo[3,4-d]pyridazin-7-amine

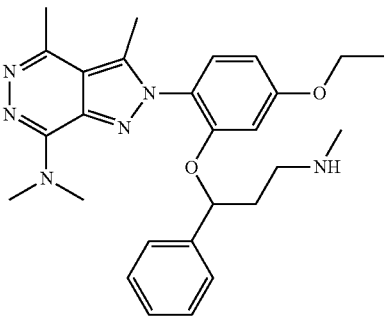 [SMILES: CCOc1ccc(-n2nc3c(N(C)C)nnc(C)c3c2C)c(OC(CCNC)c2ccccc2)c1]

Step 1. tert-Butyl (3-(2-(7-(dimethylamino)-3,4-dimethyl-2H-pyrazolo[3,4-d]pyridazin-2-yl)-5-ethoxyphenoxy)-3-phenylpropyl)(methyl)carbamate: In a sealed tube, a suspension of Boc-protected Example 25 (150 mg, 0.246 mmol), CuI (47 mg, 0.246 mmol), phenanthroline (44 mg, 0.246 mmol) and Cs$_2$CO$_3$ (104 mg, 0.0.32 mmol) in EtOH (1.5 mL) was heated at 130° C. until full conversion. The solvent was concentrated to dryness and the crude product was purified by flash chromatography, silica gel, gradient DCM to MeOH:DCM (1:4) to give the title compound (122 mg, 86% yield).

Step 2. Title compound: Using the same procedure of Example 1 Step 5 starting from the product obtained in Step 1 the title compound was obtained (52 mg, 52% yield).

HPLC retention time (method A): 3.59 min; MS: 475.2 (M+H).

This method was used for the preparation of examples 88-90 using suitable starting materials:

| EX | Structure | Chemical name | Ret time (min) | MS (M + H) | HPLC Method |
|---|---|---|---|---|---|
| 86 | 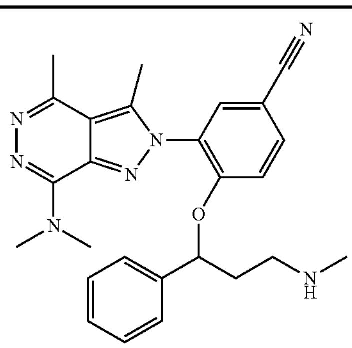 | 3-(7-(dimethylamino)-3,4-dimethyl-2H-pyrazolo[3,4-d]pyridazin-2-yl)-4-(3-(methylamino)-1-phenylpropoxy)benzonitrile | 3.22 | 456.2 | A |

| EX | Structure | Chemical name | Ret time (min) | MS (M + H) | HPLC Method |
|---|---|---|---|---|---|
| 88 | 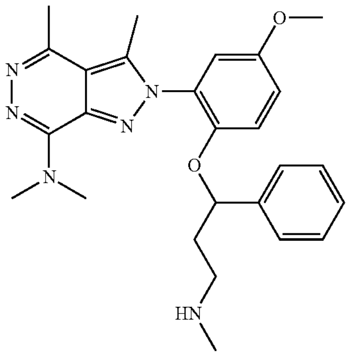 [SMILES: CNCCC(Oc1ccc(OC)cc1-n1nc2c(N(C)C)nnc(C)c2c1C)c1ccccc1] | 2-(5-methoxy-2-(3-(methylamino)-1-phenylpropoxy)phenyl)-N,N,3,4-tetramethyl-2H-pyrazolo[3,4-d]pyridazin-7-amine [(1)] | 3.48 | 461.2 | A |
| 89 | 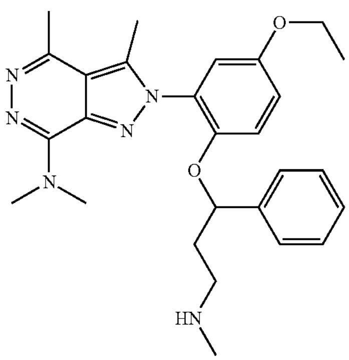 [SMILES: CCOc1ccc(OC(CCNC)c2ccccc2)c(-n2nc3c(N(C)C)nnc(C)c3c2C)c1] | 2-(5-ethoxy-2-(3-(methylamino)-1-phenylpropoxy)phenyl)-N,N,3,4-tetramethyl-2H-pyrazolo[3,4-d]pyridazin-7-amine | 3.76 | 475.3 | A |
| 90 | 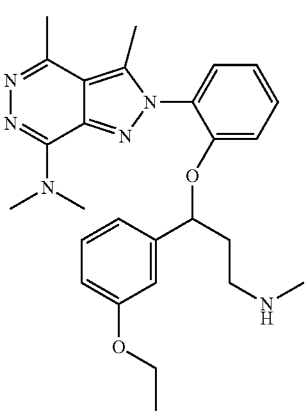 [SMILES: CCOc1cccc(C(CCNC)Oc2ccccc2-n2nc3c(N(C)C)nnc(C)c3c2C)c1] | 2-(2-(1-(3-ethoxyphenyl)-3-(methylamino)propoxy)phenyl)-N,N,3,4-tetramethyl-2H-pyrazolo[3,4-d]pyridazin-7-amine | 3.56 | 475.2 | A |

[(1)] MeOH was used as solvent.

Example 91

3-(1-(2-(7-(Dimethylamino)-3,4-dimethyl-2H-pyrazolo[3,4-d]pyridazin-2-yl)phenoxy)-3-(methylamino)propyl)benzamide

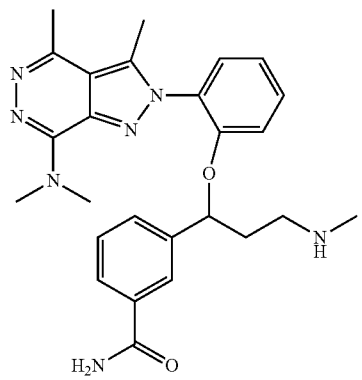 [SMILES: CNCCC(Oc1ccccc1-n1nc2c(N(C)C)nnc(C)c2c1C)c1cccc(C(N)=O)c1]

To a solution of Example 14 (60 mg, 0.06 mmol) in tert-butanol (0.9 mL), potassium hydroxide (74 mg, 0.074 mmol) was added and the mixture was heated at 80° C. overnight. Then, it was concentrated to dryness. The residue was redissolved in water and EtOAc, the phases were separated and the aqueous phase was extracted with EtOAc. The combined organic phases were washed with of NaHCO$_3$ sat. solution, dried over MgSO$_4$ and concentrated to dryness. The crude product was purified by eluting through an SCX cartridge to afford the title compound (12 mg, 19% yield).

HPLC retention time (method A): 2.79 min; MS: 474.2 (M+H).

This method was used for the preparation of examples 92-94 using suitable starting materials:

| EX | Structure | Chemical name | Ret time (min) | MS (M + H) | HPLC Method |
|---|---|---|---|---|---|
| 92 | 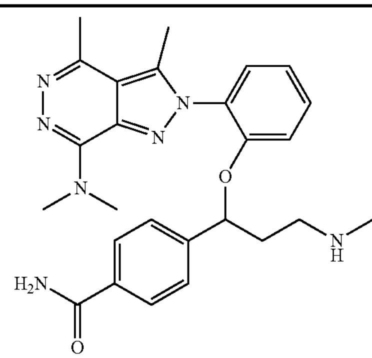 | 4-(1-(2-(7-(dimethylamino)-3,4-dimethyl-2H-pyrazolo[3,4-d]pyridazin-2-yl)phenoxy)-3-(methylamino)propyl)benzamide | 2.74 | 474.2 | A |
| 93 | 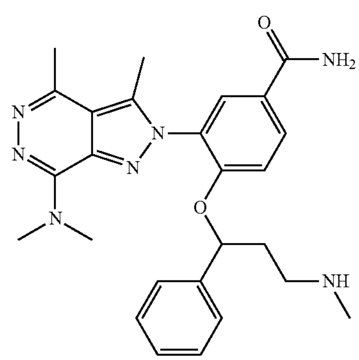 [SMILES: CNCCC(Oc1ccc(C(N)=O)cc1-n1nc2c(N(C)C)nnc(C)c2c1C)c1ccccc1] | 3-(7-(dimethylamino)-3,4-dimethyl-2H-pyrazolo[3,4-d]pyridazin-2-yl)-4-(3-(methylamino)-1-phenylpropoxy)benzamide | 2.54 | 474.2 | A |
| 94 | 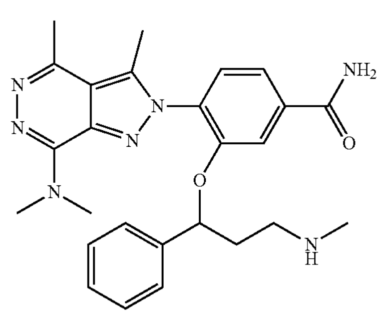 [SMILES: CNCCC(Oc1cc(C(N)=O)ccc1-n1nc2c(N(C)C)nnc(C)c2c1C)c1ccccc1] | 4-(7-(dimethylamino)-3,4-dimethyl-2H-pyrazolo[3,4-d]pyridazin-2-yl)-3-(3-(methylamino)-1-phenylpropoxy)benzamide | 2.52 | 474.2 | A |

Example 95

3-(1-(2-(7-(Dimethylamino)-3,4-dimethyl-2H-pyrazolo[3,4-d]pyridazin-2-yl)phenoxy)-3-(methylamino)propyl)benzamide

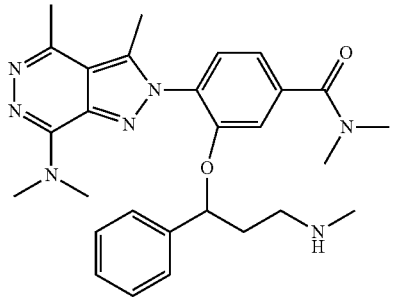 [SMILES: CNCCC(Oc1cc(C(=O)N(C)C)ccc1-n1nc2c(N(C)C)nnc(C)c2c1C)c1ccccc1]

Step 1. 3-(3-((tert-Butoxycarbonyl)(methyl)amino)-1-phenylpropoxy)-4-(7-(dimethylamino)-3,4-dimethyl-2H-pyrazolo[3,4-d]pyridazin-2-yl)benzoic acid: A solution of Boc-protected Example 85 (50 mg, 0.09 mmol) in a mixture of MeOH (0.5 mL) and 8 M NaOH (0.05 mL, 0.36 mmol) was heated at 65° C. overnight. The pH of the solution was adjusted to 4 and the solids formed were filtered and dried under vacuum to give the title compound (28 mg, 55% yield).

Step 2. tert-Butyl (3-(2-(7-(dimethylamino)-3,4-dimethyl-2H-pyrazolo[3,4-d]pyridazin-2-yl)-5-(dimethylcarbamoyl)phenoxy)-3-phenylpropyl)(methyl) carbamate: To a solution of the product obtained in Step 1 (28 mg, 0.05 mmol) in DMF (0.4 mL), dimethylamine hydrochloride (4 mg, 0.05 mmol), HATU (20 mg, 0.053 mmol) and DIPEA (25 µL, 0.14 mmol) were added. The reaction was stirred at r.t overnight. Then, NaHCO₃ sat. solution and EtOAc were added, the phases were separated and the aqueous phase was extracted with EtOAc. The combined organic phases were washed with brine, dried over MgSO₄ and concentrated to dryness. The crude product was purified by flash chromatography, silica gel, gradient DCM to MeOH:DCM (1:4) to give the title compound (20 mg, 69% yield).

Step 3. Title compound: Using the same procedure of Example 1 Step 5 starting from the product obtained in Step 2 the title compound was obtained (8 mg, 50% yield).

HPLC retention time (method A): 2.92 min; MS: 502.3 (M+H).

Example 96

3-(7-(Dimethylamino)-3,4-dimethyl-2H-pyrazolo[3,4-d]pyridazin-2-yl)-N,N-dimethyl-4-(3-(methylamino)-1-phenylpropoxy)benzamide

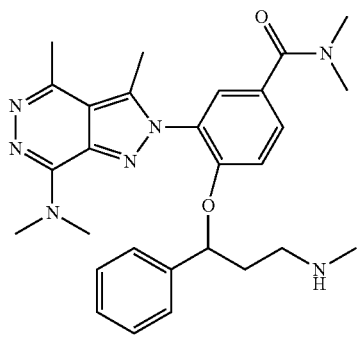 [SMILES: CNCCC(Oc1ccc(C(=O)N(C)C)cc1-n1nc2c(N(C)C)nnc(C)c2c1C)c1ccccc1]

Step 1. tert-Butyl (3-(2-(7-(dimethylamino)-3,4-dimethyl-2H-pyrazolo[3,4-d]pyridazin-2-yl)-4-(dimethylcarbamoyl)phenoxy)-3-phenylpropyl)(methyl)carbamate: To a solution of Boc-protected Example 93 (110 mg, 0.19 mmol) in DMF (2.2 mL), cooled at 0° C., NaH (60 wt % in mineral oil, 23 mg, 0.57 mmol) was added. The reaction was stirred at r.t. for 1 h and then MeI (36 µL, 0.57 mmol) was added. After stirring at r.t. overnight, H₂O was added and the mixture was extracted with DCM. The combined organic phases were washed with H₂O and brine, dried over MgSO₄ and concentrated to dryness. The crude product was purified by flash chromatography, silica gel, gradient DCM to MeOH:DCM (1:4) to give the title compound (13 mg, 11% yield).

Step 3. Title compound: A solution of the product obtained in Step 2 (13 mg, 0.021 mmol) and HCl (1.25M in EtOH, 0.7 mL, 0.54 mmol) was stirred at r.t. until full conversion. The solvent was concentrated, and the crude product was purified by eluting through an SCX cartridge to afford the title compound (9 mg, 78% yield).

HPLC retention time (method A): 2.87 min; MS: 502.2 (M+H).

Example 97

3-(7-(Dimethylamino)-3,4-dimethyl-2H-pyrazolo[3,4-d]pyridazin-2-yl)-4-(3-(methylamino)-1-phenylpropoxy)phenol

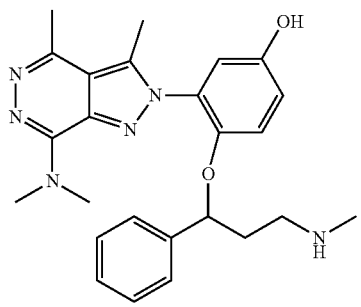 [SMILES: CNCCC(Oc1ccc(O)cc1-n1nc2c(N(C)C)nnc(C)c2c1C)c1ccccc1]

Step 1. tert-Butyl (3-(2-(7-(dimethylamino)-3,4-dimethyl-2H-pyrazolo[3,4-d]pyridazin-2-yl)-4-(4,4,5,5-tetramethyl-1,3,2-dioxaborolan-2-yl)phenoxy)-3-phenylpropyl)(methyl)carbamate: To a solution of Boc-protected Example 28 (150 mg, 0.24 mmol) in anh DMSO (4.5 mL), bis(pinacolato)diboron (68 mg, 0.27 mmol), [1,1'-bis(diphenylphosphino)ferrocene]dichloropalladium(II) (9 mg, 0.012 mmol) and potassium acetate (72 mg, 0.74 mmol) were added. The solution was heated at 80° C. overnight under argon. Brine and EtOAc were added, the phases were separated and the aqueous phase was extracted with EtOAc. The combined organic phases were dried over $MgSO_4$ and concentrated to dryness to afford the title compound (243 mg as a mixture of boronic ester and the corresponding boronic acid; overweight, quantitative yield assumed).

Step 2. tert-Butyl (3-(2-(7-(dimethylamino)-3,4-dimethyl-2H-pyrazolo[3,4-d]pyridazin-2-yl)-4-hydroxyphenoxy)-3-phenylpropyl)(methyl)carbamate: To a solution of the product obtained in Step 1 (243 mg, 66 wt %, 245 mmol) in acetone (0.8 mL), a solution of oxone (150 mg, 0.245 mmol) in water (0.8 mL) was added. The reaction mixture was stirred at r.t. overnight. Then, the solvent was removed under vacuum, and the resulting aqueous phase was basified with 1 M NaOH to pH 9 and extracted with EtOAc. The combined organic phases were washed with brine, dried over $MgSO_4$ and concentrated to dryness. The crude product was purified by flash chromatography, silica gel, gradient DCM to MeOH:DCM (1:4) to give the title compound (25 mg, 18% yield).

Step 3. Title compound: A mixture of the product obtained in Step 2 (25 mg, 0.045 mmol) and HCl (1.25 M in EtOH, 0.72 mL, 0.98 mmol) was stirred at r.t. until full conversion. The solvent was concentrated, and the crude product was purified by eluting though an SCX cartridge to afford the title compound (13 mg, 59% yield).

HPLC retention time (method A): 2.71 min; MS: 447.2 (M+H).

This method was used for the preparation of Example 98 using suitable starting materials:

Examples 99 and 100

(S)-N,N,3,4-Tetramethyl-2-(2-(3-(methylamino)-1-phenylpropoxy)phenyl)-2H-pyrazolo[3,4-d]pyridazin-7-amine and (R)-N,N,3,4-tetramethyl-2-(2-(3-(methylamino)-1-phenylpropoxy)phenyl)-2H-pyrazolo[3,4-d]pyridazin-7-amine

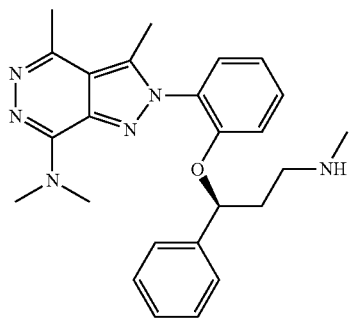

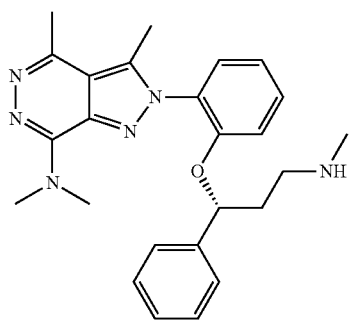

Starting from Example 6, a chiral preparative HPLC separation (column: Chiralpak AD-H; temperature: ambient; flow: 12 mL/min; eluent: n-Heptane/(EtOH+0.33% DEA) 85/15 v/v was carried out to give the title compounds.

| EX | Structure | Chemical name | Ret time (min) | MS (M+H) | HPLC Method |
|---|---|---|---|---|---|
| 98 | 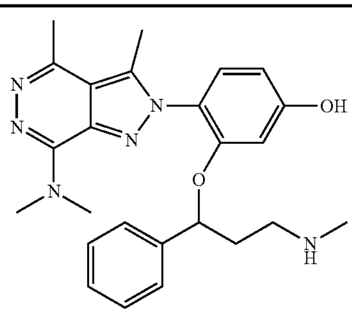 | 4-(7-(dimethylamino)-3,4-dimethyl-2H-pyrazolo[3,4-d]pyridazin-2-yl)-3-(3-(methylamino)-1-phenylpropoxy)phenol | 2.88 | 447.2 | A |

Examples 101 and 102

(R)-2-(2-(3-(Ethylamino)-1-phenylpropoxy)phenyl)-N,N,3,4-tetramethyl-2H-pyrazolo[3,4-d]pyridazin-7-amine and (S)-2-(2-(3-(ethylamino)-1-phenylpropoxy)phenyl)-N,N,3,4-tetramethyl-2H-pyrazolo[3,4-d]pyridazin-7-amine

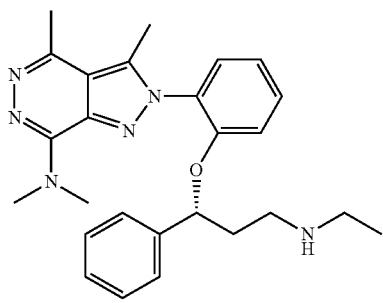

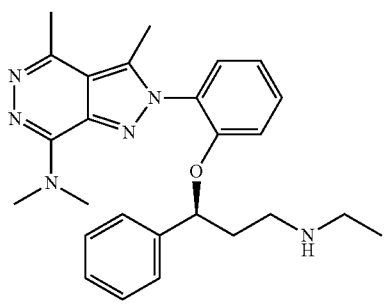

Starting from Example 1, a chiral preparative HPLC separation (column: Chiralpak IC; temperature: ambient; flow: 11 mL/min; eluent: n-Heptane/(EtOH+0.33% DEA) 85/15 v/v) was carried out to give the title compounds.

Examples 103 and 104

(S)-2-(2-(1-(3-Fluorophenyl)-3-(methylamino)propoxy)phenyl)-N,N,3,4-tetramethyl-2H-pyrazolo[3,4-d]pyridazin-7-amine and (R)-2-(2-(1-(3-fluorophenyl)-3-(methylamino)propoxy)phenyl)-N,N,3,4-tetramethyl-2H-pyrazolo[3,4-d]pyridazin-7-amine

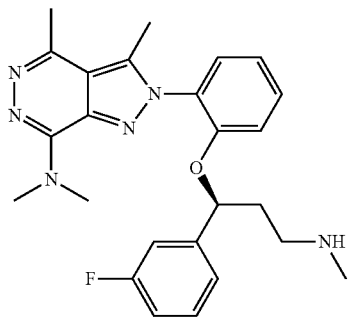

-continued

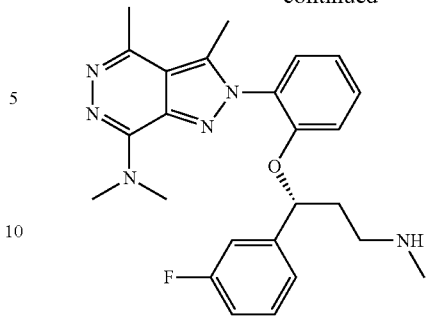

Starting from Example 44, a chiral preparative HPLC separation (column: Chiralpak AD-H; temperature: ambient; flow: 10 mL/min; eluent: n-Heptane/(EtOH+0.33% DEA) 85/15 v/v) was carried out to give the title compounds.

Table of Examples with Binding to the μ-Opioid Receptor and the $\alpha_2\delta$-1 Subunit of the Voltage-Gated Calcium Channel:

Biological Activity

Pharmacological Study

Human $\alpha_2\delta$-1 Subunit of $Ca_v2.2$ Calcium Channel Assay

Human $\alpha_2\delta$-1 enriched membranes (2.5 μg) were incubated with 15 nM of radiolabeled [3H]-Gabapentin in assay buffer containing Hepes-KOH 10 mM, pH 7.4. NSB (non specific binding) was measured by adding 10 μM pregabalin. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 hour and 30 μl of scintillation cocktail were added to each well before radioactivity reading. Readings were performed in a Trilux 1450 Microbeta radioactive counter (Perkin Elmer), i.e. Human $\alpha_2\delta$-1 enriched membranes (2.5 μg) were incubated with 15 nM of radiolabeled [3H]-Gabapentin in assay buffer containing Hepes-KOH 10 mM, pH 7.4. NSB (non specific binding) was measured by adding 10 μM pregabalin. The binding of the test compound was measured at five different concentrations. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 hour and 30 μl of scintillation cocktail were added to each well before radioactivity reading. Readings were performed in a Trilux 1450 Microbeta radioactive counter (Perkin Elmer).

Human μ-Opioid Receptor Radioligand Assay

To investigate binding properties of test compounds to human μ-opioid receptor, transfected CHO-K1 cell membranes and [3H]-DAMGO (Perkin Elmer, ES-542-C), as the radioligand, were used. The assay was carried out with 20 μg of membrane suspension, 1 nM of [3H]-DAMGO in either absence or presence of either buffer or 10 μM Naloxone for total and non-specific binding, respectively. Binding buffer contained Tris-HCl 50 mM, MgCl$_2$ 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail, preferably, transfected CHO-K1 cell membranes (20 μg) were incubated with 1 nM of [$^3$H]-DAMGO in assay buffer containing Tris-HCl 50 mM, MgCl2 5 mM at pH 7.4. NBS (non-specific binding) was measured by adding 10 μM Naloxone. The binding of the test compound was measured at five different concentrations. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\alpha_2\delta$ subunit of voltage-gated calcium channels and the μ-opioid receptor it is a very preferred embodiment in which the compounds are selected which act as dual ligands of the $\alpha_2\delta$ subunit of voltage-gated calcium channels and the μ-opioid receptor and especially compounds which have a binding expressed as $K_i$ responding to the following scales:

$K_i(p)$ is preferably <1000 nM, more preferably <500 nM, even more preferably <100 nM.

$K_i(\alpha_2\delta\text{-}1)$ is preferably <10000 nM, more preferably <5000 nM, or even more preferably <500 nM.

The following scale has been adopted for representing the binding to μ-opioid receptor expressed as $K_i$:

+$K_i(\mu)$>=500 nM
++100 nM<=$K_i(\mu)$<500 nM
+++$K_i(\mu)$<100 nM

The following scale has been adopted for representing the binding to the $\alpha_2\delta$-1 subunit of voltage-gated calcium channels expressed as $K_i$:

+$K_i(\alpha_2\delta\text{-}1)$>=5000 nM
++500 nM<=$K_i(\alpha_2\delta\text{-}1)$<5000 nM
+++$K_i(\alpha_2\delta\text{-}1)$<500 nM All compounds prepared in the present application exhibit binding to the $\alpha_2\delta$-1 subunit of voltage-gated calcium channels and the μ-opioid receptor, in particular the following binding results are shown:

| EXAMPLE | Binding μ | Binding $\alpha_2\delta$-1 |
|---|---|---|
| 1 | ++ | ++ |
| 2 | + | + |
| 3 | + | + |
| 4 | + | ++ |
| 5 | + | ++ |
| 6 | ++ | ++ |
| 7 | + | ++ |
| 8 | + | ++ |
| 9 | ++ | + |
| 10 | + | ++ |
| 11 | + | ++ |
| 12 | + | ++ |
| 13 | + | + |
| 14 | + | ++ |
| 15 | + | ++ |
| 16 | + | + |
| 17 | + | ++ |
| 18 | + | ++ |
| 19 | + | ++ |
| 20 | ++ | ++ |
| 21 | + | ++ |
| 22 | + | ++ |
| 23 | + | ++ |
| 24 | ++ | ++ |
| 25 | + | ++ |
| 26 | + | ++ |
| 27 | ++ | ++ |
| 28 | + | ++ |
| 29 | + | ++ |
| 30 | + | + |
| 31 | + | ++ |
| 32 | + | ++ |
| 33 | + | ++ |
| 34 | + | ++ |
| 35 | + | ++ |
| 36 | + | ++ |
| 37 | ++ | ++ |
| 38 | + | ++ |
| 39 | + | ++ |
| 40 | + | ++ |
| 41 | + | ++ |
| 42 | + | +++ |
| 43 | + | ++ |
| 44 | ++ | +++ |
| 45 | + | ++ |
| 46 | + | ++ |
| 47 | ++ | +++ |
| 48 | + | ++ |
| 49 | + | ++ |
| 50 | + | + |
| 51 | + | + |
| 52 | ++ | ++ |
| 53 | + | + |
| 54 | + | + |
| 55 | ++ | ++ |
| 56 | ++ | ++ |
| 57 | + | + |
| 58 | +++ | + |
| 59 | + | ++ |
| 60 | + | ++ |
| 61 | + | ++ |
| 62 | + | ++ |
| 63 | + | + |
| 64 | + | + |
| 65 | ++ | ++ |
| 66 | + | + |
| 67 | + | ++ |
| 68 | + | ++ |
| 69 | + | + |
| 70 | + | + |
| 71 | + | ++ |
| 72 | + | ++ |
| 73 | +++ | ++ |
| 74 | + | + |
| 75 | + | + |
| 76 | + | ++ |
| 77 | + | ++ |
| 78 | ++ | ++ |
| 79 | ++ | ++ |
| 80 | + | ++ |
| 81 | + | + |
| 82 | + | ++ |
| 83 | + | ++ |
| 84 | + | ++ |
| 85 | + | + |
| 86 | + | + |
| 87 | + | +++ |
| 88 | + | ++ |
| 89 | + | ++ |
| 90 | + | ++ |
| 91 | + | ++ |
| 92 | + | ++ |
| 93 | + | + |
| 94 | + | + |
| 95 | + | ++ |
| 96 | + | + |
| 97 | + | ++ |
| 98 | + | ++ |
| 99 | ++ | ++ |

-continued

| EXAMPLE | Binding μ | Binding $\alpha_2\delta$-1 |
|---|---|---|
| 100 | + | ++ |
| 101 | ++ | ++ |
| 102 | + | ++ |
| 103 | + | +++ |
| 104 | ++ | ++ |

The invention claimed is:
1. A compound of general formula (I):

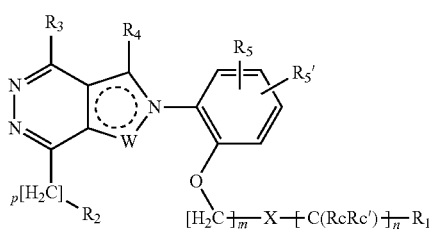

wherein
m is 0, 1, 2, 3 or 4;
n is 0, 1, 2, 3 or 4;
p is 0, 1, 2, 3 or 4;
W is nitrogen or —C($R_{4'}$)—;
X is selected from the group consisting of a bond, substituted or unsubstituted aryl and —C$R_x R_{x'}$—;
  $R_x$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
  $R_{x'}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_1$ is selected from the group consisting of —$NR_6 R_{6'}$ and substituted or unsubstituted N-containing-heterocyclyl;
  wherein $R_6$ and $R_{6'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
$R_2$ is selected from the group consisting of hydrogen, —$NR_7 R_{7'}$, —CN, —$CHR_7 R_{7'}$ and substituted or unsubstituted heterocyclyl;
  wherein $R_7$ and $R_{7'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl and substituted or unsubstituted alkyheterocyclyl;
$R_3$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_4$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_{4'}$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_5$ and $R_{5'}$ are independently selected from the group consisting of hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —$OR_8$, —$NO_2$, —$NR_8 R_{8'}$, —$NR_8 C(O)R_{8'}$, —$NR_8 S(O)_2 R_{8'}$, —$S(O)_2 NR_8 R_{8'}$, —$NR_8 C(O)NR_{8'} R_{8''}$, —$SR_8$, —$S(O)R_8$, $S(O)_2 R_8$, —CN, haloalkyl, haloalkoxy, —$C(O)OR_8$, —$C(O)NR_8 R_{8'}$, —$OCH_2 CH_2 OR_8$, —$NR_8 S(O)_2 NR_{8'} R_{8''}$ and $C(CH_3)_2 OR_8$;
  wherein $R_8$, $R_{8'}$ and $R_{8''}$ are independently selected from the group consisting of hydrogen, unsubstituted $C_{1-6}$ alkyl, unsubstituted $C_{2-6}$ alkenyl and unsubstituted $C_{2-6}$ alkynyl;
$R_c$ and $R_{c'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
alternatively, $R_c$ and $R_{c'}$, together with the carbon atom to which they are attached, form a substituted or unsubstituted cycloalkyl;
optionally as a stereoisomer, including enantiomers and diastereomers, a racemate or as a mixture of at least two stereoisomers, including enantiomers and/or diastereomers, in any mixing ratio, or a corresponding salt thereof, or a corresponding solvate thereof.

2. The compound according to claim 1, wherein the compound of Formula (I) is a compound of Formula (I')

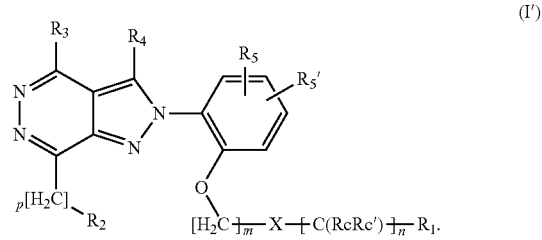

3. The compound according to claim 1, wherein the compound of Formula (I) is a compound of Formula ($I^{2'}$)

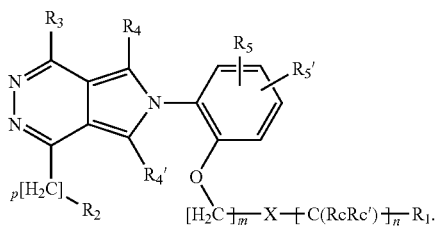

(I2')

4. The compound according to claim 1, wherein R₁ is selected from the group consisting of —NR₆R₆' and substituted or unsubstituted N-containing-heterocyclyl;
   wherein R₆ and R₆' are independently selected from the group consisting of hydrogen, substituted or unsubstituted C₁₋₆ alkyl, substituted or unsubstituted alkylaryl, substituted or unsubstituted cycloalkyl and substituted or unsubstituted alkylcycloalkyl.

5. The compound according to claim 1, wherein R₁ is —NR₆R₆', wherein R₆ and R₆' are independently selected from the group consisting of hydrogen, substituted or unsubstituted C₁₋₆ alkyl, substituted or unsubstituted alkylaryl, substituted or unsubstituted cycloalkyl and substituted or unsubstituted alkylcycloalkyl;
   or R₁ is substituted or unsubstituted N-containing-heterocyclyl selected from the group consisting of:

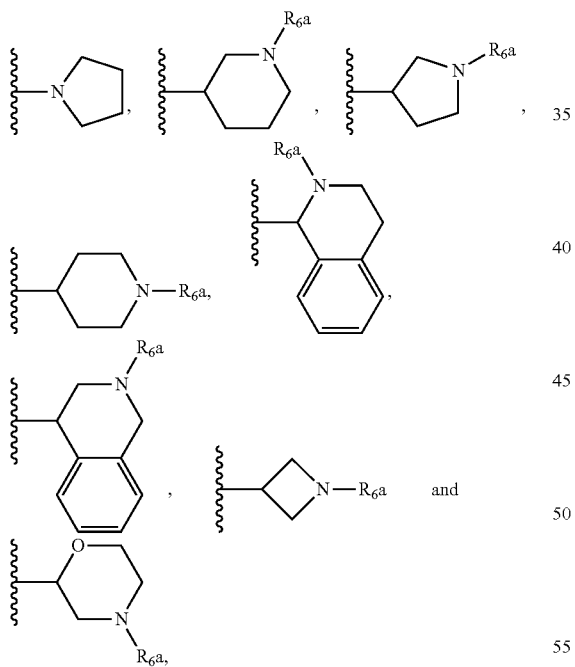

wherein R₆ₐ is selected from the group consisting of hydrogen, substituted or unsubstituted C₁₋₆ alkyl and substituted or unsubstituted alkylaryl.

6. The compound according to claim 1, wherein X is selected from the group consisting of a bond, substituted or unsubstituted aryl and —CRₓRₓ'—, wherein
   Rₓ' is selected from the group consisting of hydrogen, substituted or unsubstituted C₁₋₆ alkyl, substituted or unsubstituted C₂₋₆ alkenyl and substituted or unsubstituted C₂₋₆ alkynyl;
   Rₓ is selected from the group consisting of substituted or unsubstituted C₁₋₆ alkyl, substituted or unsubstituted C₂₋₆ alkenyl, substituted or unsubstituted C₂₋₆ alkynyl,

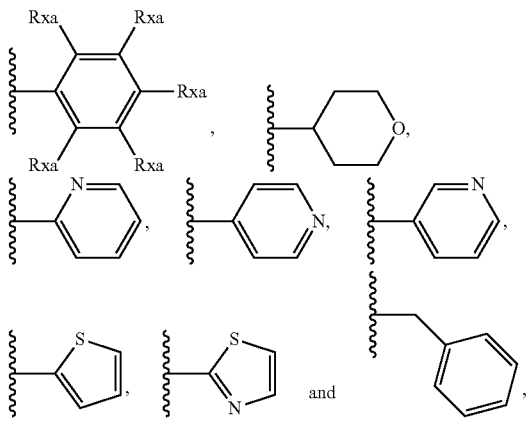

wherein each Rₓₐ independently represents hydrogen, halogen, —OR₁₀, —NR₁₀C(O)R₁₀', —CN or —C(O)NR₁₀R₁₀',
   wherein R₁₀, R₁₀' and R₁₀'' are independently selected from the group consisting of hydrogen and unsubstituted C₁₋₆ alkyl.

7. The compound according to claim 1, wherein R₂ is selected from the group consisting of hydrogen, —NR₇R₇', —CN, —CHR₇R₇' and substituted or unsubstituted heterocyclyl,
   wherein R₇ and R₇' are independently selected from the group consisting of hydrogen, substituted or unsubstituted C₁₋₆ alkyl, substituted or unsubstituted aryl and substituted or unsubstituted alkylaryl.

8. The compound according to claim 1, wherein R₂ is selected from hydrogen, —NR₇R₇', —CN, —CHR₇R₇' and heterocyclyl selected from:

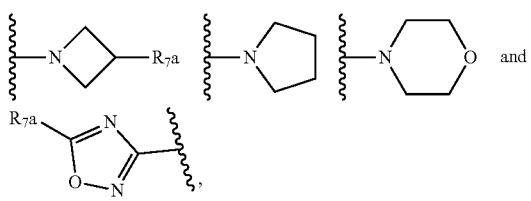

wherein R₇ₐ is selected from the group consisting of hydrogen, substituted or unsubstituted alkoxy and substituted or unsubstituted C₁₋₆ alkyl.

9. The compound according to claim 1, wherein R₅ and R₅' are independently selected from the group consisting of hydrogen, halogen, substituted or unsubstituted C₁₋₆ alkyl, substituted or unsubstituted C₂₋₆ alkenyl, substituted or unsubstituted C₂₋₆ alkynyl, substituted or unsubstituted aryl, substituted or unsubstituted alkylaryl, substituted or unsubstituted cycloalkyl, substituted or unsubstituted alkylcycloalkyl, substituted or unsubstituted heterocyclyl, substituted or unsubstituted alkyheterocyclyl, —OR₈, —NO₂, —NR₈R₈', —NR₈C(O)R₈', —NR₈S(O)₂R₈', —S(O)₂NR₈R₈', —NR₈C(O)NR₈'R₈''', —SR₈, —S(O)R₈, S(O)₂R₈, —CN, haloalkyl, haloalkoxy, —C(O)OR₈, —C(O)NR₈R₈', —OCH₂CH₂OR₈, —NR₈S(O)₂NR₈'R₈''' and C(CH₃)₂OR₈, wherein R₈, R₈', and R₈''R₈, R₈', and R₈'' are independently selected from the group consisting of hydrogen and unsubstituted C₁₋₆ alkyl.

10. The compound according to claim 1, wherein R₅ and R₅, are independently selected from the group consisting of hydrogen, halogen, substituted or unsubstituted heterocyclyl, —OR₈, — —NR₈C(O)R₈'', —CN and —C(O)NR₈R₈''.

11. The compound according to claim 10, wherein R₈, R₈' and R₈'', are independently selected from hydrogen and unsubstituted C₁₋₆ alkyl.

12. The compound according to claim 1, which is selected from the group consisting of:
- 2-(2-(3-(Ethylamino)-1-phenylpropoxy)phenyl)-N,N,3,4-tetramethyl-2H-pyrazolo[3,4-d]pyridazin-7-amine,
- N,N,3,4-tetramethyl-2-(2-(2-(pyrrolidin-1-yl)ethoxy) phenyl)-2H-pyrazolo[3,4-d]pyridazin-7-amine,
- N,N,3,4-tetramethyl-2-(2-(piperidin-4-ylmethoxy)phenyl)-2H-pyrazolo[3,4-d]pyridazin-7-amine,
- N,N,3,4-tetramethyl-2-(2-(3-(methylamino)propoxy)phenyl)-2H-pyrazolo[3,4-d]pyridazin-7-amine,
- N,N, 3,4-tetramethyl-2-(2-(piperidin-3-ylmethoxy)phenyl)-2H-pyrazolo[3,4-d]pyridazin-7-amine,
- N,N,3,4-tetramethyl-2-(2-(3-(methylamino)-1-phenylpropoxy)phenyl)-2H-pyrazolo[3,4-d]pyridazin-7-amine,
- N-benzyl-3,4-dimethyl-2-(2-(3-(methylamino)-1-phenylpropoxy)phenyl)-2H-pyrazolo[3,4-d]pyridazin-7-amine,
- 2-(2-((1-benzylpyrrolidin-3-yl)oxy)phenyl)-N,N,3,4-tetramethyl-2H-pyrazolo[3,4-d]pyridazin-7-amine,
- 3,4-dimethyl-2-(2-(3-(methylamino)-1-phenylpropoxy) phenyl)-N-phenyl-2H-pyrazolo[3,4-d]pyridazin-7-amine,
- N,N,3,4-tetramethyl-2-(2-((4-(methylamino)butan-2-yl)oxy)phenyl)-2H-pyrazolo[3,4-d]pyridazin-7-amine,
- N,N,3,4-tetramethyl-2-(2-(phenyl(piperidin-4-yl)methoxy)phenyl)-2H-pyrazolo[3,4-d]pyridazin-7-amin,e
- 2-(2-((4-(benzylamino)butan-2-yl)oxy)phenyl)-N,N,3,4-tetramethyl-2H-pyrazolo[3,4-]pyridazin-7-amine,
- N,N,3,4-tetramethyl-2-(2-(piperidin-4-yloxy)phenyl)-2H-pyrazolo[3,4-d]pyridazin-7-amine,
- 3-(1-(2-(7-(dimethylamino)-3,4-dimethyl-2H-pyrazolo[3,4-d]pyridazin-2-yl)phenoxy)-3-(methylamino)propyl)benzonitrile,
- 4-(1-(2-(7-(dimethylamino)-3,4-dimethyl-2H-pyrazolo[3,4-d]pyridazin-2-yl)phenoxy)-3-(methylamino)propyl)benzonitrile,
- N,N,3,4-tetramethyl-2-(2-(3-(methylamino)-1-(tetrahydro-2H-pyran-4-yl)propoxy)phenyl)-2H-pyrazolo[3,4-d]pyridazin-7-amine,
- 2-(2-(2-amino-2-phenylethoxy)phenyl)-N,N,3,4-tetramethyl-2H-pyrazolo[3,4-d]pyridazin-7-amine,
- N,N,3,4-tetramethyl-2-(2-(3-(methylamino)-1-(pyridin-2-yl)propoxy)phenyl)-2H-pyrazolo[3,4-d]pyridazin-7-amine,
- N,N,3,4-tetramethyl-2-(2-(3-(methylamino)-1-(pyridin-4-yl)propoxy)phenyl)-2H-pyrazolo[3,4-d]pyridazin-7-amine,
- 2-(2-(3-((cyclopropylmethyl)amino)-1-phenylpropoxy) phenyl)-N,N,3,4-tetramethyl-2H-pyrazolo[3,4-d]pyridazin-7-amine,
- N,N,3,4-tetramethyl-2-(2-(3-(methylamino)-1-(pyridin-3-yl)propoxy)phenyl)-2H-pyrazolo[3,4-d]pyridazin-7-amine,
- 2-(2-(3-amino-3-phenylpropoxy)phenyl)-N,N,3,4-tetramethyl-2H-pyrazolo[3,4-d]pyridazin-7-amine,
- 3-(2-(3,4-dimethyl-7-morpholino-2H-pyrazolo[3,4-d]pyridazin-2-yl)phenoxy)-N-methyl-3-phenylpropan-1-amine,
- N,N,3,4-tetramethyl-2-(2-(1-phenyl-3-(propylamino) propoxy)phenyl)-2H-pyrazolo[3,4-d]pyridazin-7-amine,
- 2-(4-bromo-2-(3-(methylamino)-1-phenylpropoxy)phenyl)-N,N,3,4-tetramethyl-2H-pyrazolo[3,4-d]pyridazin-7-amine,
- 2-(2-(3-((2-methoxyethyl)amino)-1-phenylpropoxy)phenyl)-N,N,3,4-tetramethyl-2H-pyrazolo[3,4-d]pyridazin-7-amine,
- 2-(2-(3-(cyclopropylamino)-1-phenylpropoxy)phenyl)-N,N,3,4-tetramethyl-2H-pyrazolo[3,4-d]pyridazin-7-amine,
- 2-(5-bromo-2-(3-(methylamino)-1-phenylpropoxy)phenyl)-N,N,3,4-tetramethyl-2H-pyrazolo[3,4-d]pyridazin-7-amine,
- N,N,3,4-tetramethyl-2-(2-((1,2,3,4-tetrahydroisoquinolin-1-yl)methoxy)phenyl)-2H-pyrazolo[3,4-d]pyridazin-7-amine,
- N,N,3,4-tetramethyl-2-(2-((1,2,3,4-tetrahydroisoquinolin-4-yl)methoxy)phenyl)-2H-pyrazolo[3,4-d]pyridazin-7-amine,
- N,N,3,4-tetramethyl-2-(2-(3-(phenethylamino)propoxy) phenyl)-2H-pyrazolo[3,4-d]pyridazin-7-amine,
- N,N,3,4-tetramethyl-2-(2-((1,2,3,4-tetrahydroisoquinolin-4-yl)oxy)phenyl)-2H-pyrazolo[3,4-d]pyridazin-7-amine,
- N,N,3,4-tetramethyl-2-(2-(3-(methylamino)-1-(thiazol-2-yl)propoxy)phenyl)-2H-pyrazolo[3,4-d]pyridazin-7-amine,
- 2-(2-(azetidin-3-yl(phenyl)methoxy)phenyl)-N,N,3,4-tetramethyl-2H-pyrazolo[3,4-d]pyridazin-7-amine,
- 3-(2-(7-(3-methoxyazetidin-1-yl)-3,4-dimethyl-2H-pyrazolo[3,4-d]pyridazin-2-yl)phenoxy)-N-methyl-3-phenylpropan-1-amine,
- 3-(2-(3,4-dimethyl-7-(pyrrolidin-1-yl)-2H-pyrazolo[3,4-d]pyridazin-2-yl)phenoxy)-N-methyl-3-phenylpropan-1-amine,
- N-ethyl-N,3,4-trimethyl-2-(2-(3-(methylamino)-1-phenylpropoxy)phenyl)-2H-pyrazolo[3,4-d]pyridazin-7-amine,
- 2-(2-(3-amino-1-phenylpropoxy)phenyl)-N,N,3,4-tetramethyl-2H-pyrazolo[3,4-d]pyridazin-7-amine,
- 3-(2-(7-(azetidin-1-yl)-3,4-dimethyl-2H-pyrazolo[3,4-d]pyridazin-2-yl)phenoxy)-N-methyl-3-phenylpropan-1-amine,
- N-benzyl-N,3,4-trimethyl-2-(2-(3-(methylamino) propoxy)phenyl)-2H-pyrazolo[3,4-d]pyridazin-7-amine,
- 2-(2-(1-(2-fluorophenyl)-3-(methylamino)propoxy)phenyl)-N,N,3,4-tetramethyl-2H-pyrazolo[3,4-d]pyridazin-7-amine,
- 2-(2-(1-(4-fluorophenyl)-3-(methylamino)propoxy)phenyl)-N,N,3,4-tetramethyl-2H-pyrazolo[3,4-d]pyridazin-7-amine,
- 2-(2-((4-(benzyl(methyl)amino)-1-methoxybutan-2-yl)oxy)phenyl)-N,N,3,4-tetramethyl-2H-pyrazolo[3,4-d]pyridazin-7-amine,
- 2-(2-(1-(3-fluorophenyl)-3-(methylamino)propoxy)phenyl)-N,N,3,4-tetramethyl-2H-pyrazolo[3,4-d]pyridazin-7-amine,
- N,N,3,4-tetramethyl-2-(2-((3-((methylamino) methyl)benzyl)oxy)phenyl)-2H-pyrazolo[3,4-d]pyridazin-7-amine, N,N,3,4-tetramethyl-2-(2-(4-(methylamino)-1-phenylbutoxy)phenyl)-2H-pyrazolo[3,4-d]pyridazin-7-amine,
2-(2-(3-(ethylamino)-1-(3-fluorophenyl)propoxy)phenyl)-N,N,3,4-tetramethyl-2H-pyrazolo[3,4-d]pyridazin-7-amine,
2-(2-(1-(3,5-difluorophenyl)-3-(methylamino)propoxy)phenyl)-N,N,3,4-tetramethyl-2H-pyrazolo[3,4-d]pyridazin-7-amine,
N,N,3,4-tetramethyl-2-(2-((R)—((S)-morpholin-2-yl)(phenyl)methoxy)phenyl)-2H-pyrazolo[3,4-c]pyridazin-7-amine,
N, N,3,4-Tetramethyl-2-(2-(pyrrolidin-3-yloxy)phenyl)-2H-pyrazolo[3,4-d]pyridazin-7-amine,
2-(2-((1-methoxy-4-(methylamino)butan-2-yl)oxy)phenyl)-N,N,3,4-tetramethyl-2H-pyrazolo[3,4-d]pyridazin-7-amine,
2-(2-(3-(Dimethylamino)-1-phenylpropoxy)phenyl)-N,N,3,4-tetramethyl-2H-pyrazolo[3,4-d]pyridazin-7-amine,
N,N,3,4-tetramethyl-2-(2-((1-methylpyrrolidin-3-yl)oxy)phenyl)-2H-pyrazolo[3,4-d]pyridazin-7-amine,
N,N,3,4-tetramethyl-2-(2-((1-methylpiperidin-4-yl)(phenyl)methoxy)phenyl)-2H-pyrazolo[3,4-d]pyridazin-7-amine,
N,N,3,4-tetramethyl-2-(2-((1-phenethylpyrrolidin-3-yl)oxy)phenyl)-2H-pyrazolo[3,4-d]pyridazin-7-amine,
2-(2-(3-((2,2-difluoroethyl)amino)-1-phenylpropoxy)phenyl)-N,N,3,4-tetramethyl-2H-pyrazolo[3,4-]pyridazin-7-amine,
2-(2-((1-benzylpiperidin-4-yl)methoxy)phenyl)-N,N,3,4-tetramethyl-2H-pyrazolo[3,4-d]pyridazin-7-amine,
N,N,3,4-tetramethyl-2-(2-((1-phenethylpiperidin-4-yl)methoxy)phenyl)-2H-pyrazolo[3,4-d]pyridazin-7-amine,
2-(((3,4-Dimethyl-2-(2-(3-(methylamino)-1-phenylpropoxy)phenyl)-2H-pyrazolo[3,4-d]pyridazin-7-yl)(methyl)amino)ethanol,
N-(2-methoxyethyl)-N,3,4-trimethyl-2-(2-(3-(methylamino)-1-phenylpropoxy)phenyl)-2H-pyrazolo[3,4-d]pyridazin-7-amine,
3-((3,4-dimethyl-2-(2-(3-(methylamino)-1-phenylpropoxy)phenyl)-2H-pyrazolo[3,4-d]pyridazin-7-yl)(methy)amino)propan-1-ol,
N1-(3,4-dimethyl-2-(2-(3-(methylamino)-1-phenylpropoxy)phenyl)-2H-pyrazolo[3,4-d]pyridazin-7-yl)-N1,N2,N2-trimethylethane-1,2-diamine,
2-(3,4-Dimethyl-2-(2-(3-(methylamino)-1-phenylpropoxy)phenyl)-2H-pyrazolo[3,4-d]pyridazin-7-yl)acetonitrile,
3-(2-(3,4-Dimethyl-7-((5-methyl-1,2,4-oxadiazol-3-yl)methyl)-2H-pyrazolo[3,4-d]pyridazin-2-yl)phenoxy)-N-methyl-3-phenylpropan-1-amine,
N-Methyl-3-phenyl-3-(2-(1,4,5,7-tetramethyl-6H-pyrrolo[3,4-d]pyridazin-6-yl)phenoxy)propan-1-amine,
3-(2-(3,4-Dimethyl-2H-pyrazolo[3,4-d]pyridazin-2-yl)phenoxy)-N-methyl-3-phenylpropan-1-amine,
N,N,3,4-Tetramethyl-2-(2-(2-(methylamino)-1-phenylethoxy)phenyl)-2H-pyrazolo[3,4-d]pyridazin-7-amine,
N,3,4-Trimethyl-2-(2-(3-(methylamino)-1-phenylpropoxy)phenyl)-2H-pyrazolo[3,4-d]pyridazin-7-amine,
N-methyl-3-phenyl-3-(2-(3,4,7-trimethyl-2H-pyrazolo[3,4-d]pyridazin-2-yl)phenoxy)propan-1-amine,
3-(2-(7-isopropyl-3,4-dimethyl-2H-pyrazolo[3,4-d]pyridazin-2-yl)phenoxy)-N-methyl-3-phenylpropan-1-amine,
N,N-dimethyl-2-(2-(3-(methylamino)-1-phenylpropoxy)phenyl)-2H-pyrazolo[3,4-d]pyridazin-7-amine,
N,N,3,4-Tetramethyl-2-(2-((2-((methylamino)methyl)benzyl)oxy)phenyl)-2H-pyrazolo[3,4-d]pyridazin-7-amine,
2-(2-(3-((2-Fluoroethyl)amino)-1-phenylpropoxy)phenyl)-N,N,3,4-tetramethyl-2H-pyrazolo[3,4-d]pyridazin-7-amine,
2-(2-((1-(Benzyl(methyl)amino)-3-phenylpropan-2-yl)oxy)phenyl)-N,N,3,4-tetramethyl-2H-pyrazolo[3,4-d]pyridazin-7-amine,
2-(2-((4-(benzyl(methyl)amino)-1-phenylbutan-2-yl)oxy)phenyl)-N,N,3,4-tetramethyl-2H-pyrazolo[3,4-d]pyridazin-7-amine,
N,N,3,4-Tetramethyl-2-(2-((1-(methylamino)-3-phenylpropan-2-yl)oxy)phenyl)-2H-pyrazolo[3,4-d]pyridazin-7-amine,
N,N,3,4-tetramethyl-2-(2-((4-(methylamino)-1-phenylbutan-2-yl)oxy)phenyl)-2H-pyrazolo[3,4-d]pyridazin-7-amine,
N,N,3,4-Tetramethyl-2-(2-(3-(methylamino)-1-(thiophen-2-yl)propoxy)phenyl)-2H-pyrazolo[3,4-d]pyridazin-7-amine,
3-(1-(2-(7-(Dimethylamino)-3,4-dimethyl-2H-pyrazolo[3,4-d]pyridazin-2-yl)phenoxy)-3-(methylamino)propyl)phenol,
1-(4-(7-(Dimethylamino)-3,4-dimethyl-2H-pyrazolo[3,4-d]pyridazin-2-yl)-3-(3-(methylamino)-1-phenylpropoxy)phenyl)pyrrolidin-2-one,
1-(3-(7-(dimethylamino)-3,4-dimethyl-2H-pyrazolo[3,4-d]pyridazin-2-yl)-4-(3-(methylamino)-1-phenylpropoxy)phenyl)pyrrolidin-2-one,
N-(4-(7-(dimethylamino)-3,4-dimethyl-2H-pyrazolo[3,4-d]pyridazin-2-yl)-3-(3-(methylamino)-1-phenylpropoxy)phenyl)acetamide,
N-(3-(7-(dimethylamino)-3,4-dimethyl-2H-pyrazolo[3,4-d]pyridazin-2-yl)-4-(3-(methylamino)-1-phenylpropoxy)phenyl)acetamide,
N-(3-(1-(2-(7-(dimethylamino)-3,4-dimethyl-2H-pyrazolo[3,4-d]pyridazin-2-yl)phenoxy)-3-(methylamino)propyl)phenyl)acetamide,
4-(7-(Dimethylamino)-3,4-dimethyl-2H-pyrazolo[3,4-d]pyridazin-2-yl)-3-(3-(methylamino)-1-phenylpropoxy)benzonitrile,
3-(7-(dimethylamino)-3,4-dimethyl-2H-pyrazolo[3,4-d]pyridazin-2-yl)-4-(3-(methylamino)-1-phenylpropoxy)benzonitrile,
2-(4-Ethoxy-2-(3-(methylamino)-1-phenylpropoxy)phenyl)-N,N,3,4-tetramethyl-2H-pyrazolo[3,4-d]pyridazin-7-amine,
2-(5-methoxy-2-(3-(methylamino)-1-phenylpropoxy)phenyl)-N,N,3,4-tetramethyl-2H-pyrazolo[3,4-d]pyridazin-7-amine,
2-(5-ethoxy-2-(3-(methylamino)-1-phenylpropoxy)phenyl)-N,N,3,4-tetramethyl-2H-pyrazolo[3,4-d]pyridazin-7-amine,
2-(2-(1-(3-ethoxyphenyl)-3-(methylamino)propoxy)phenyl)-N,N,3,4-tetramethyl-2H-pyrazolo[3,4-d]pyridazin-7-amine,
3-(1-(2-(7-(Dimethylamino)-3,4-dimethyl-2H-pyrazolo[3,4-d]pyridazin-2-yl)phenoxy)-3-(methylamino)propyl)benzamide,
4-(1-(2-(7-(dimethylamino)-3,4-dimethyl-2H-pyrazolo[3,4-d]pyridazin-2-yl)phenoxy)-3-(methylamino)propyl)benzamide, 3-(7-(dimethylamino)-3,4-dimethyl-2H-pyrazolo[3,4-d]
   pyridazin-2-yl)-4-(3-(methylamino)-1-phenylpropoxy)
   benzamide,
4-(7-(dimethylamino)-3,4-dimethyl-2H-pyrazolo[3,4-d]
   pyridazin-2-yl)-3-(3-(methylamino)-1-phenylpropoxy)
   benzamide,
3-(1-(2-(7-(Dimethylamino)-3,4-dimethyl-2H-pyrazolo
   [3,4-d]pyridazin-2-yl)phenoxy)-3-(methylamino)pro-
   pyl)benzamide,
3-(7-(Dimethylamino)-3,4-dimethyl-2H-pyrazolo[3,4-d]
   pyridazin-2-yl)-N,N-dimethyl-4-(3-(methylamino)-1-
   phenylpropoxy)benzamide,
3-(7-(Dimethylamino)-3,4-dimethyl-2H-pyrazolo[3,4-d]
   pyridazin-2-yl)-4-(3-(methylamino)-1-phenylpropoxy)
   phenol,
4-(7-(dimethylamino)-3,4-dimethyl-2H-pyrazolo[3,4-d]
   pyridazin-2-yl)-3-(3-(methylamino)-1-phenylpropoxy)
   phenol,
(S)—N,N,3,4-Tetramethyl-2-(2-(3-(methylamino)-1-phe-
   nylpropoxy)phenyl)-2H-pyrazolo[3,4-d]pyridazin-7-
   amine,
(R)—N,N,3,4-tetramethyl-2-(2-(3-(methylamino)-1-phe-
   nylpropoxy)phenyl)-2H-pyrazolo[3,4-d]pyridazin-7-
   amine,
(R)-2-(2-(3-(Ethylamino)-1-phenylpropoxy)phenyl)-N,
   N,3,4-tetramethyl-2H-pyrazolo[3,4-d]pyridazin-7-
   amine,
(S)-2-(2-(3-(ethylamino)-1-phenylpropoxy)phenyl)-N,N,
   3,4-tetramethyl-2H-pyrazolo[3,4-d]pyridazin-7-amine,
(S)-2-(2-(1-(3-Fluorophenyl)-3-(methylamino)propoxy)
   phenyl)-N,N,3,4-tetramethyl-2H-pyrazolo[3,4-d]
   pyridazin-7-amine and
(R)-2-(2-(1-(3-fluorophenyl)-3-(methylamino)propoxy)
   phenyl)-N,N,3,4-tetramethyl-2H-pyrazolo[3,4-d]
   pyridazin-7-amine.

13. A process for the preparation of the compound of formula (I) according to claim 1

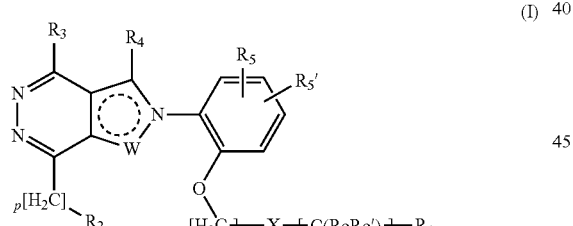
(I)

wherein
a) when the group $[CH_2]_pR_2$ is attached to the core structure through a carbon atom, said process comprises treating a compound of formula III

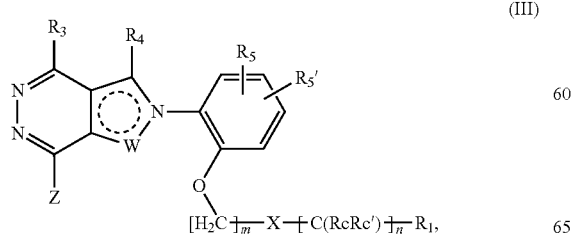
(III)

wherein Z represents a halogen, including chloro, or triflate with a suitable organometallic reagent of formula IVa,

IVa wherein V represents a suitable organometallic reagent, including a boron or zinc reagent;

or b) when the group $[CH_2]_pR_2$ is attached to the core structure through a nitrogen atom, said process comprises treating a compound of formula III

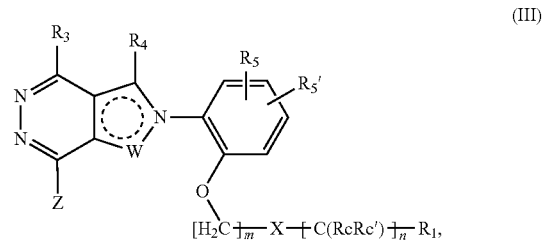
(III)

wherein Z represents a halogen, including chloro, or triflate with an amine of formula IVb

IVb;

OR c) said process comprises treating a compound of formula VH

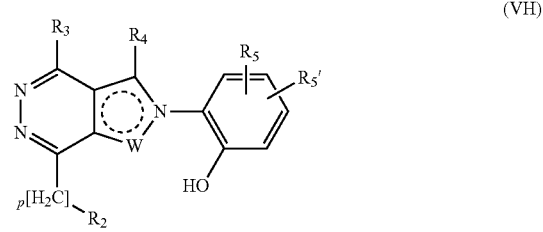
(VH)

with a compound of formula VI

VI wherein Y represents a leaving group, including halogen, mesylate, tosylate, nosylate or triflate, or OH.

14. A process for the preparation of the compound according of formula (I) according to claim 1, employing a compound of Formula II, IIP, III, IIIP, IIIH, IVa, IVb, VP, VH, VI, VII, VIIP, VIII, IX, IXP, X, XI, XIP, IIa, IIaP, XII, XIII, XIIIP, XIVa, XIVb, XV, XVP, Ib, VbP or VbH II
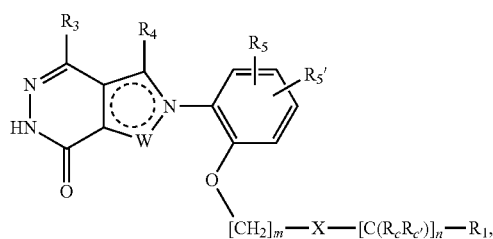
IIP
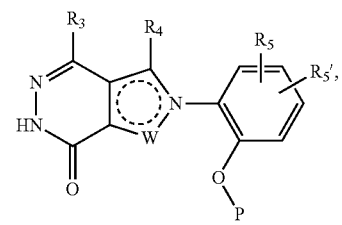
III
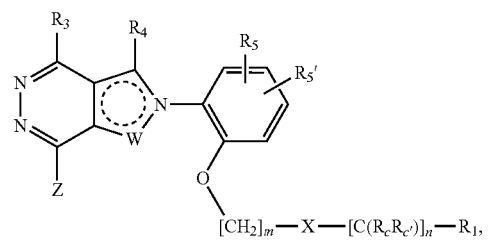
IIIP
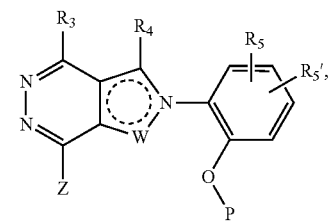
IIIH
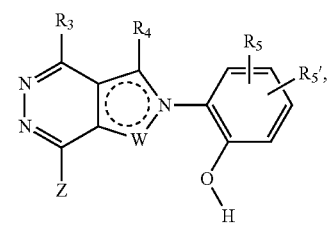
IVa
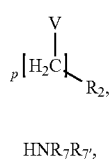
IVb
HNR$_7$R$_{7'}$,
VP
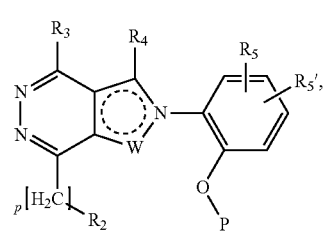
VH
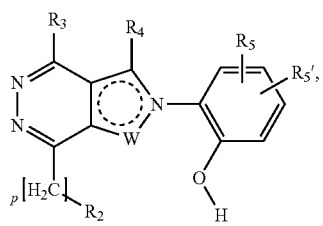
VI
VII
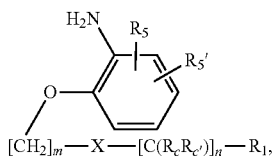
VIIP
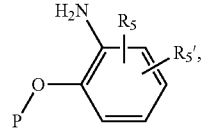
VIII
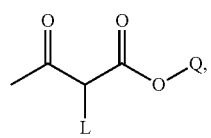
IX
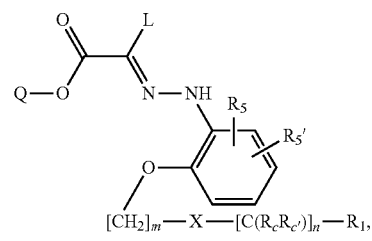
IXP
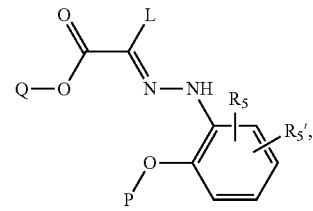
X
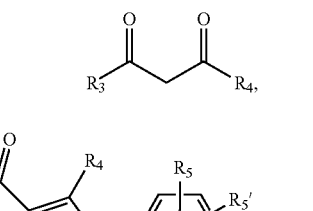
XI
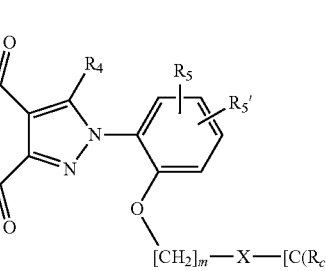

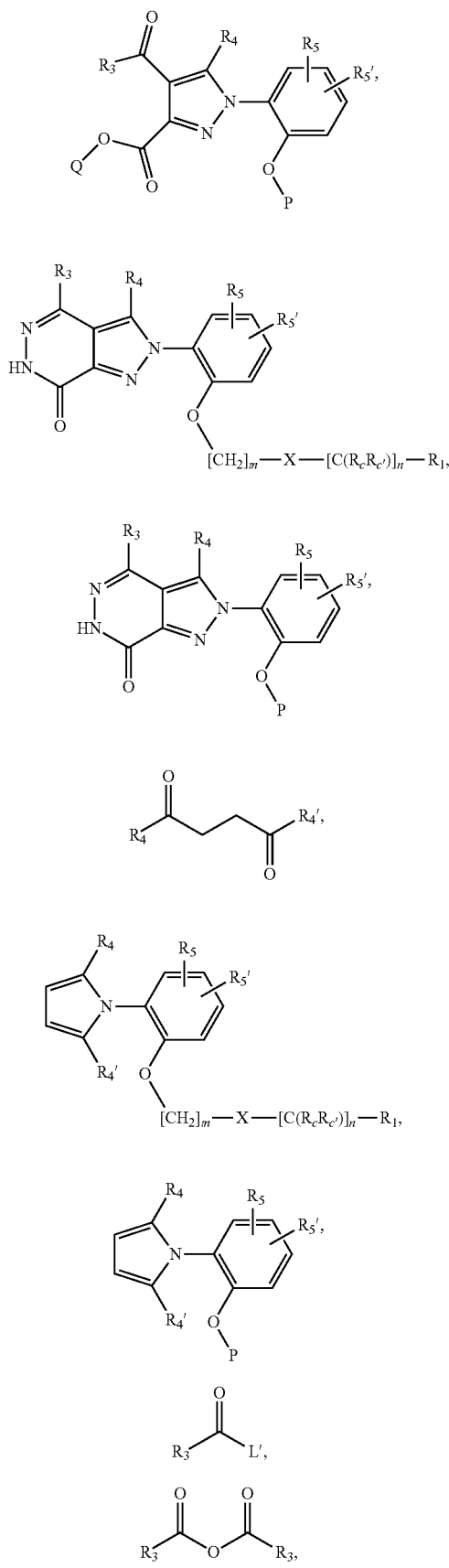
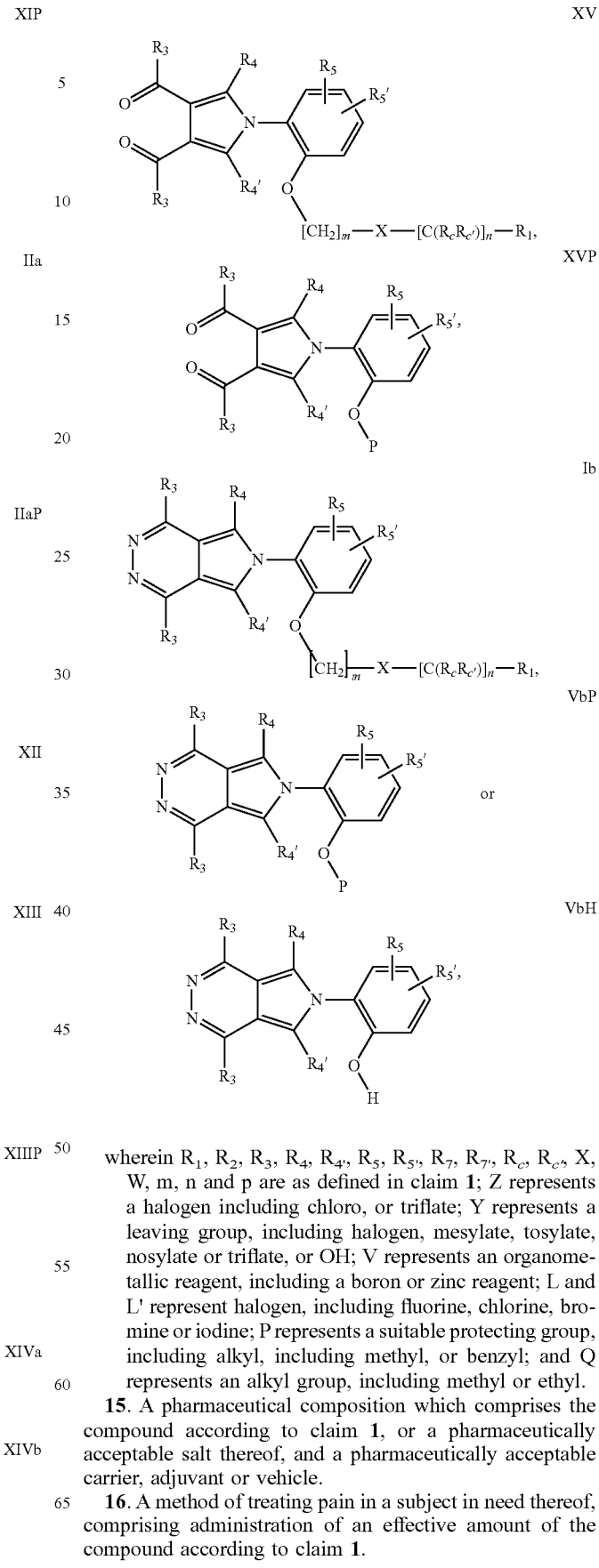

wherein $R_1$, $R_2$, $R_3$, $R_4$, $R_{4'}$, $R_5$, $R_{5'}$, $R_7$, $R_{7'}$, $R_c$, $R_{c'}$, X, W, m, n and p are as defined in claim 1; Z represents a halogen including chloro, or triflate; Y represents a leaving group, including halogen, mesylate, tosylate, nosylate or triflate, or OH; V represents an organometallic reagent, including a boron or zinc reagent; L and L' represent halogen, including fluorine, chlorine, bromine or iodine; P represents a suitable protecting group, including alkyl, including methyl, or benzyl; and Q represents an alkyl group, including methyl or ethyl.

15. A pharmaceutical composition which comprises the compound according to claim 1, or a pharmaceutically acceptable salt thereof, and a pharmaceutically acceptable carrier, adjuvant or vehicle.

16. A method of treating pain in a subject in need thereof, comprising administration of an effective amount of the compound according to claim 1.

17. The method according to claim 16, wherein the pain is selected from the group consisting of medium to severe pain, visceral pain, chronic pain, cancer pain, migraine, inflammatory pain, acute pain or neuropathic pain, allodynia and hyperalgesia.

* * * * *